United States Patent
Brack-Werner et al.

(10) Patent No.: US 10,421,749 B2
(45) Date of Patent: Sep. 24, 2019

(54) PYRONE DERIVATIVES FOR USE AS ANTIVIRAL AGENTS

(71) Applicants: HELMHOLTZ ZENTRUM MÜNCHEN-DEUTSCHES FORSCHUNGSZENTRUM FÜR GESUNDHEIT UND UMWELT (GMBH), Neuherberg (DE); LEIBNIZINSTITUT FÜR NATURSTOFF-FORSCHUNG UND INFEKTIONSBIOLOGIE E. V.—HANS-KNÖLL-INSTITUT, Jena (DE)

(72) Inventors: Ruth Brack-Werner, Munich (DE); Markus Helfer, Munich (DE); Manfred Rösner, Eppstein/Ts (DE); Martha Schneider, Feldkirchen-Westerham (DE); Ulrike Protzer, Munich (DE); Christian Hertweck, Leipzig (DE); Martina Werneburg, Berlin (DE)

(73) Assignees: HELMHOLTZ ZENTRUM MÜNCHEN-DEUTSCHES FORSCHUNGSZENTRUM FÜR GESUNDHEIT UND UMWELT (GMBH), Neuherberg (DE); LEIBNIZINSTITUT FÜR NATURSTOFF-FORSCHUNG UND INFEKTIONSBIOLOGIE E. V. -HANS-KNÖLL-INSTITUT, Jena (DE)

( * ) Notice: Subject to any disclaimer, the term of this patent is extended or adjusted under 35 U.S.C. 154(b) by 0 days.

(21) Appl. No.: 15/565,585

(22) PCT Filed: Apr. 7, 2016

(86) PCT No.: PCT/EP2016/057598
§ 371 (c)(1),
(2) Date: Oct. 10, 2017

(87) PCT Pub. No.: WO2016/162405
PCT Pub. Date: Oct. 13, 2016

(65) Prior Publication Data
US 2018/0118725 A1     May 3, 2018

(30) Foreign Application Priority Data

Apr. 10, 2015   (EP) .................... 15163128

(51) Int. Cl.
C07D 407/04    (2006.01)
A61K 31/351    (2006.01)
C07D 309/32    (2006.01)
A61K 45/06     (2006.01)
A61P 31/22     (2006.01)
A61P 31/20     (2006.01)
A61P 31/14     (2006.01)
A61P 31/18     (2006.01)
A61P 31/16     (2006.01)
A61K 9/00      (2006.01)

(52) U.S. Cl.
CPC .......... C07D 407/04 (2013.01); A61K 9/0053 (2013.01); A61K 31/351 (2013.01); A61K 45/06 (2013.01); A61P 31/14 (2018.01); A61P 31/16 (2018.01); A61P 31/18 (2018.01); A61P 31/20 (2018.01); A61P 31/22 (2018.01); C07D 309/32 (2013.01)

(58) Field of Classification Search
None
See application file for complete search history.

(56) References Cited

FOREIGN PATENT DOCUMENTS

DE    4121468 A1 *  1/1993  ............. A61K 31/35
EP    2 108 650 A1   10/2009

OTHER PUBLICATIONS

Weickmann et al., DE 4121468 A1 (Jan. 14, 1993) Google machine translation obtained Jan. 20, 2019.*

(Continued)

*Primary Examiner* — Brian J Davis

(57) ABSTRACT

The present invention relates to compounds and compositions for use in methods of treating and/or preventing conditions, disorders or diseases that are mediated or caused by a virus.

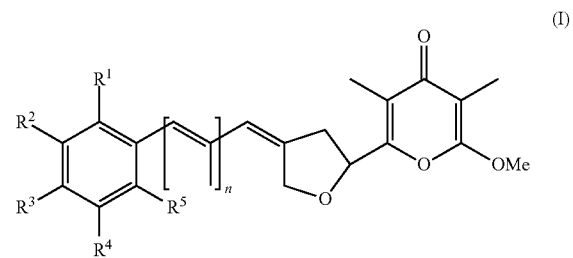

(I)

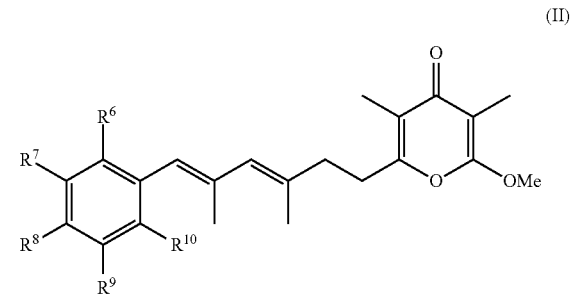

(II)

16 Claims, 12 Drawing Sheets

(56) References Cited

OTHER PUBLICATIONS

Choi et al., "Cloning and heterologous expression of the spectinabilin biosynthetic gene cluster from *Streptomyces spectabilis*," Molecular Biosystems 6: 336-338, 2010.
European Patent Office, International Search Report for PCT/EP2016/057598, dated Jul. 1, 2016, seven pages.
Ishibashi et al., "Total Synthesis of (+)-Isoaureothin. Determination of the absolute igurations of Aureothin, Isoaureothin and Spectinabilin," Tetrahedron Letters 33(4): 521-524, 1992.
Werneburg et al., "Chemoenzymatic total synthesis of the antiproliferative polyketide (+)-(R)-Aureothin," ChemBioChem 9: 2064-2066, 2008.

* cited by examiner

A)

B)

$EC_{50} = 614{,}7$ pM

C)

D)

E)

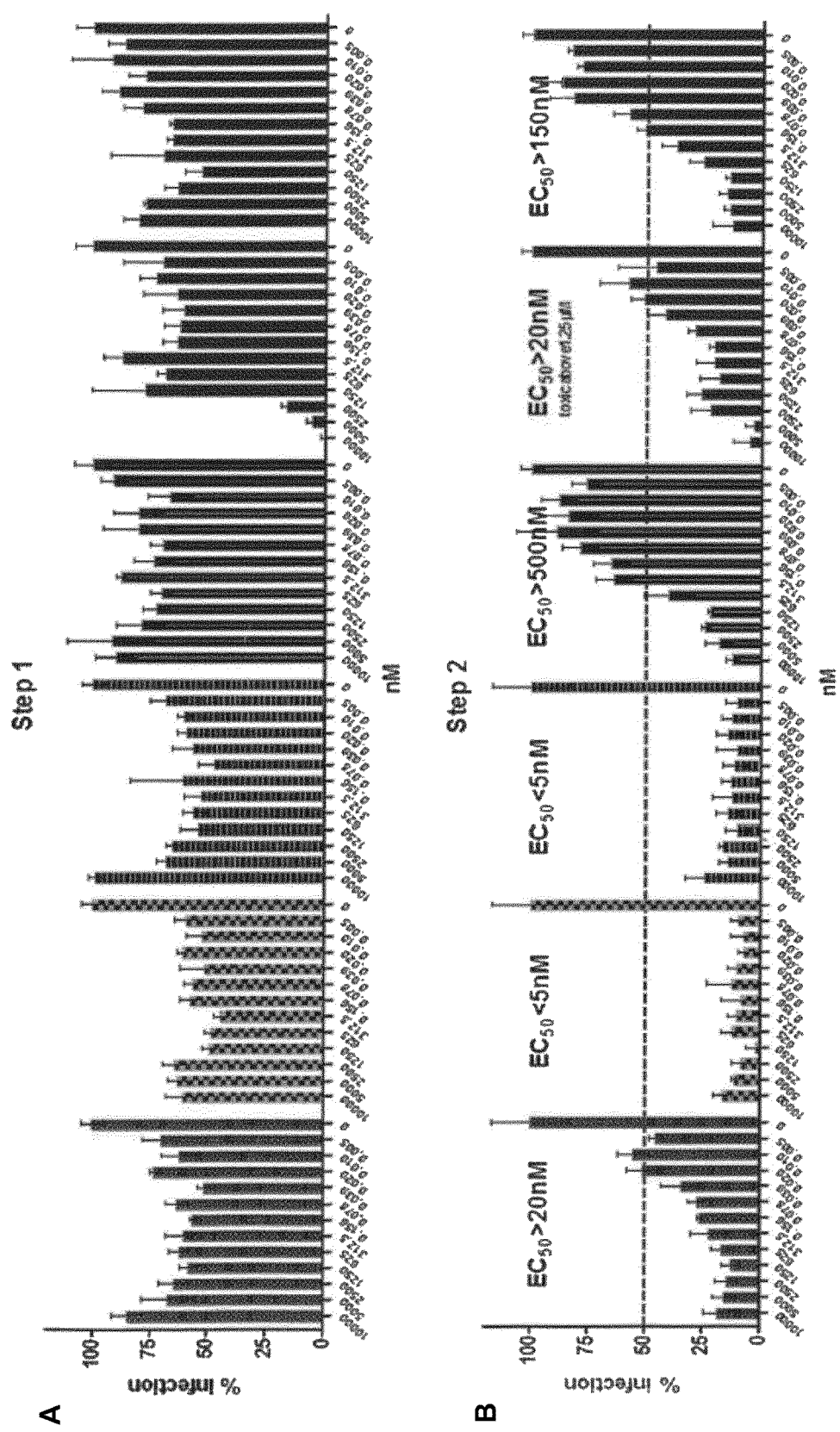

concentrations in nM each compound from left to right:
250
125
62,5
31,25
15,625
7,813
3,906
1,953
0,977
0,488
0,244
0,122
0,000

PYRONE DERIVATIVES FOR USE AS ANTIVIRAL AGENTS

CROSS-REFERENCES TO RELATED APPLICATIONS

This application is a U.S. national phase application of International PCT Patent Application No. PCT/EP2016/057598, which was filed on Apr. 7, 2016, which claims priority to European Patent Application No. 15163128.0, filed Apr. 10, 2015. These applications are incorporated herein by reference in their entireties.

TECHNICAL FIELD OF THE INVENTION

The present invention relates to the use of compounds in methods of treating and/or preventing conditions, disorders or diseases that are mediated or caused by a virus. In particular, the compounds described herein are useful in the treatment and/or prevention of conditions, disorders or diseases that are mediated or caused by an animal pathogenic virus which uses cellular mechanisms in the human or animal host for its replication and/or for its transcription.

BACKGROUND

Due to the implementation of highly active antiretroviral therapy (HAART) it is possible to considerably reduce virus propagation in HIV-infected individuals resulting in a substantially extension of life expectancies. However, HAART still has various drawbacks, including the emergence of resistant virus strains, severe side effects of drugs, suboptimal penetration of the central nervous system, failure to completely suppress viremia, and the requirement for lifelong treatment. Furthermore, HAART is very cost intensive and, thus, out of reach for most HIV-infected individuals, in particular those in developing countries. Achieving widespread antiviral treatment is a major goal for the prevention of virus-induced diseases in infected individuals and also has the potential to reduce virus transmission, which is particularly important in view of the fact that effective prevention strategies like protective HIV vaccines have not yet been developed. Thus, there is a need for the development of novel antiviral drugs and their implementation into affordable and efficient therapies.

SUMMARY OF THE INVENTION

In a first aspect, the present invention provides a compound selected from the group consisting of a pyrone derivative having the general formula (I) or (II)

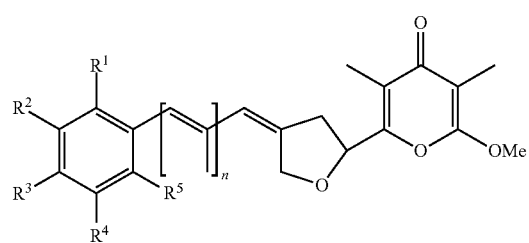

(I)

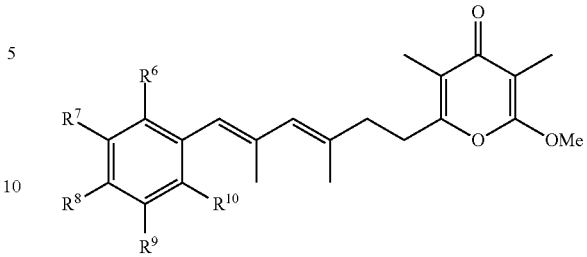

(II)

and hydrates, solvates, salts, complexes, racemic mixtures, diastereomers, enantiomers, and tautomers thereof and isotopically enriched forms of any of the foregoing, wherein $R^1$ to $R^{10}$ and n are as specified in claim 1, for use in a method of treating and/or preventing a condition, disorder or disease that is mediated or caused by an animal pathogenic virus which uses cellular mechanisms in the animal host for its replication and/or for its transcription.

In a further aspect, the present invention provides a pharmaceutical composition for use in a method of treating and/or preventing a condition, disorder or disease that is mediated or caused by an animal pathogenic virus which uses cellular mechanisms in the animal host for its replication and/or for its transcription, said composition comprising a pyrone derivative as described herein, and one or more excipients, and optionally one or more additional active compounds.

In a further aspect, the present invention provides a method for treating and/or preventing a condition, disorder or disease that is mediated or caused by an animal pathogenic virus which uses cellular mechanisms in the animal host for its replication and/or for its transcription, said method comprising administering a therapeutically effective amount of a pyrone derivative as described herein to an animal in need thereof.

Other features and advantages of the present invention will be apparent from the following detailed description and claims.

Figure 1:
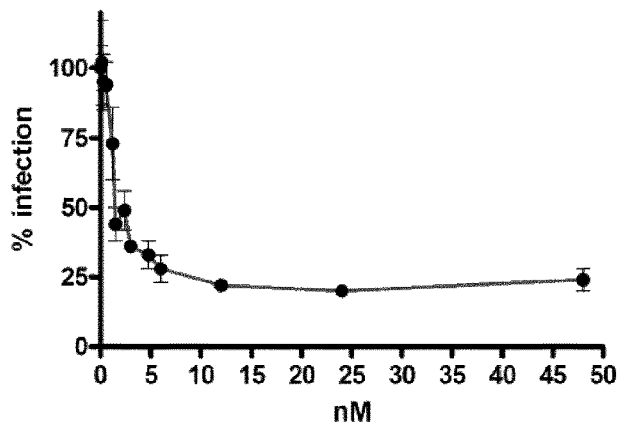
FIG. 1: Efficacy of Compound 1 in LC5-RIC Cells Infected with HIV
Figure 1:
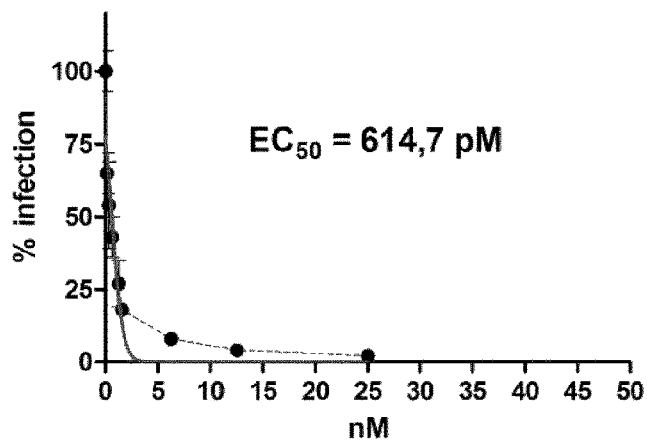
Figure 1:
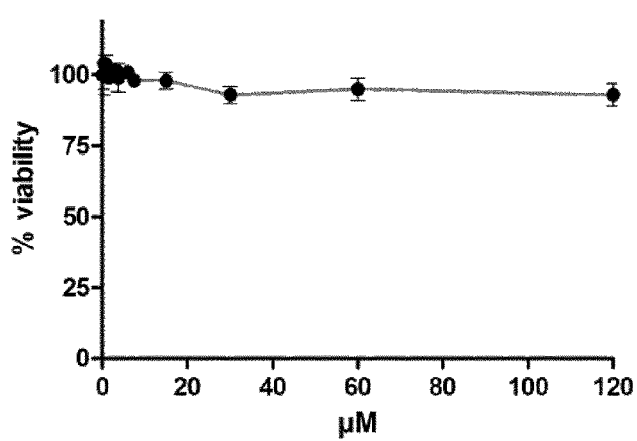
Figure 1:
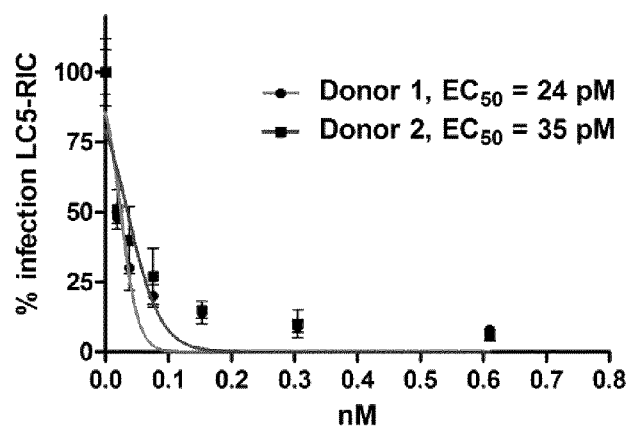
Figure 1:
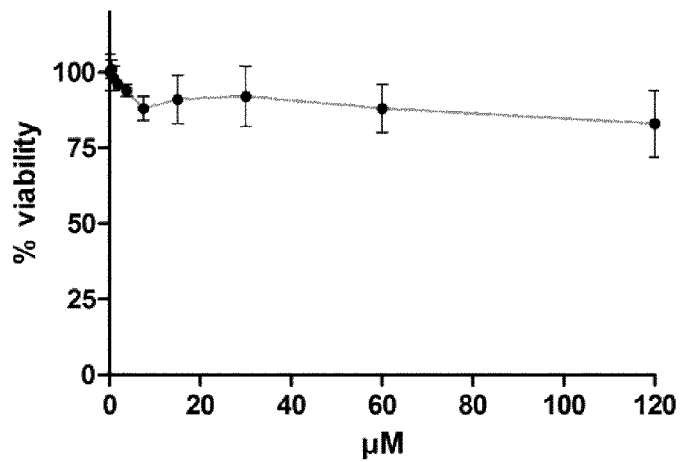

LC5-RIC cells were exposed to Compound 1 and HIV for 48 h and inhibitory effects of Compound 1 on HIV replication were evaluated in two steps. The first step (FIG. 1A) measured fluorescence signal intensities of the cells in the test cultures. For the second step, aliquots of supernatants of the test cultures were transferred to a new plate with LC5-RIC cells (FIGS. 1B and C) or PBMCs (FIG. 1D and E), and fluorescent signals were measured 72 h after transfer. Effects of Compound 1 on the viability of cells in test cultures were analyzed by MTT assay (FIGS. 1C and E).

Figure 2:
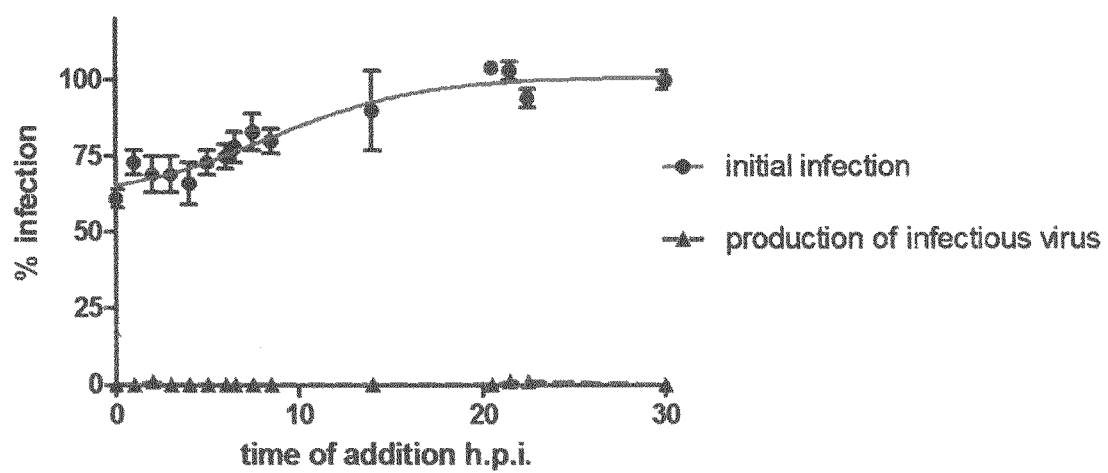

FIG. 2: Time-of-Addition Assay

HIV preparations were added to LC5-RIC cells at the time point 0. Compound 1 was added to the cultures at different time points after virus addition (i.e., p.i.). Plates were incubated for a total period of 48 h after virus addition, and cultures were assayed for HIV reporter expression (circles; step 1) or for amounts of infectious virus in culture supernatants (triangle; step 2). Fluorescent signal intensities of treated cultures were related to those of cultures infected without inhibitors (set at 100% infection).

Figure 3:
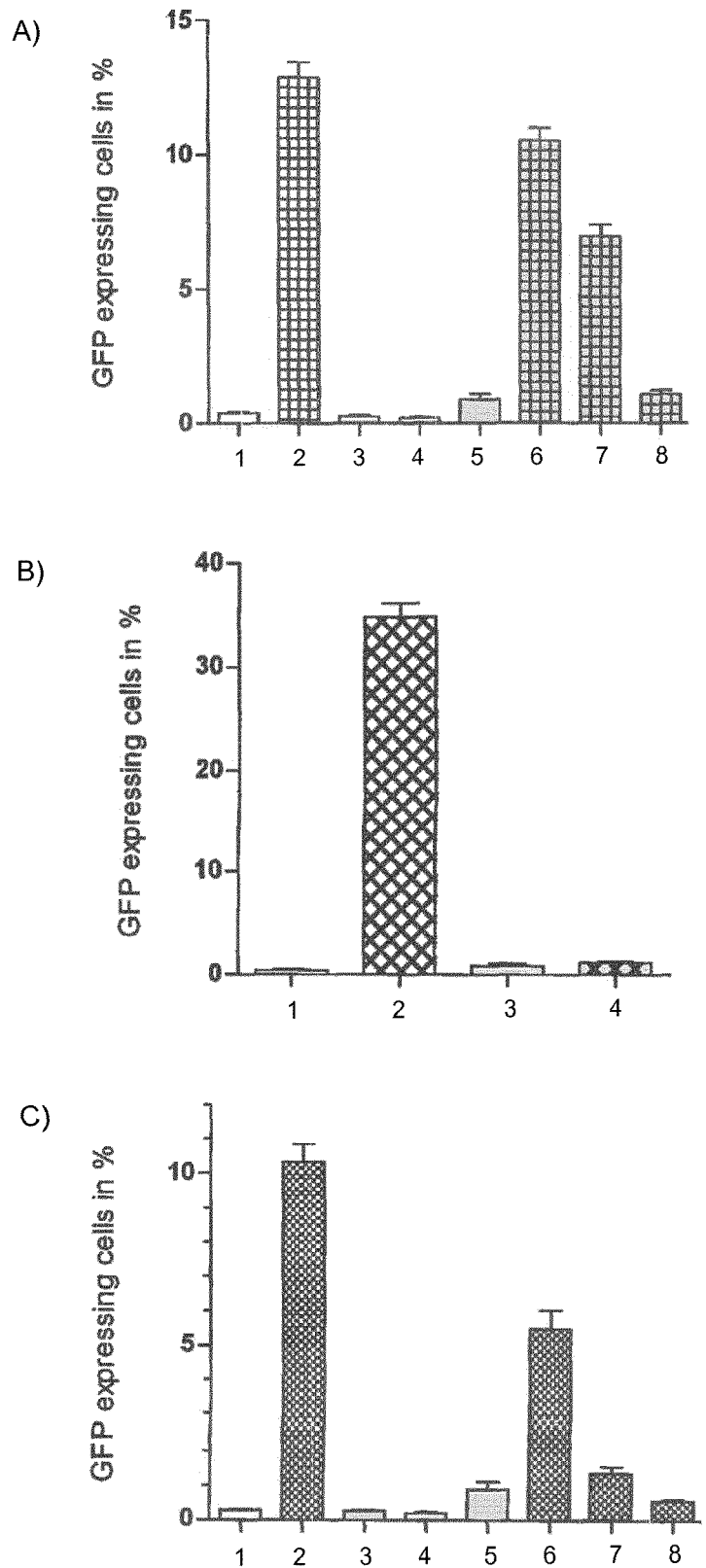

FIG. 3: Evaluation of Effects of Compound 1 on the Expression of HIV-1

The expression of HIV-1 in HNSCLatGFP1.1 cells (a human cell into the genome of which the genome of a HIV-1-gfp reporter virus has been stably integrated) is transcriptionally inactive, but can be induced by activators (such as TNF or SAHA) and measured using the GFP reported (FACS). A) Induction of expression of HIV-1 in HNSCLatGFP1.1 cells using TNF: 1: untreated (negative control); 2: TNF (positive control); 3: 0.5 nM Compound 1; 4: 5 nM Compound 1; 5: 50 nM Compound 1; 6: 0.5 nM Compound 1+TNF; 7: 5 nM Compound 1+TNF; 8: 50 nM Compound 1+TNF. B) Induction of expression of HIV-1 in HNSCLatGFP1.1 cells using TNF+SAHA: 1: mock; 2: TNF+SAHA; 3: 50 nM Compound 1; 4: TNF+SAHA+50 nM Compound 1. C) Induction of expression of HIV-1 in HNSCLatGFP1.1 cells using SAHA: 1: untreated (negative control); 2: SAHA (positive control); 3: 0.5 nM Compound 1; 4: 5 nM Compound 1; 5: 50 nM Compound 1; 6: 0.5 nM Compound 1+SAHA; 7: 5 nM Compound 1+SAHA; 8: 50 nM Compound 1+SAHA.

Figure 4:
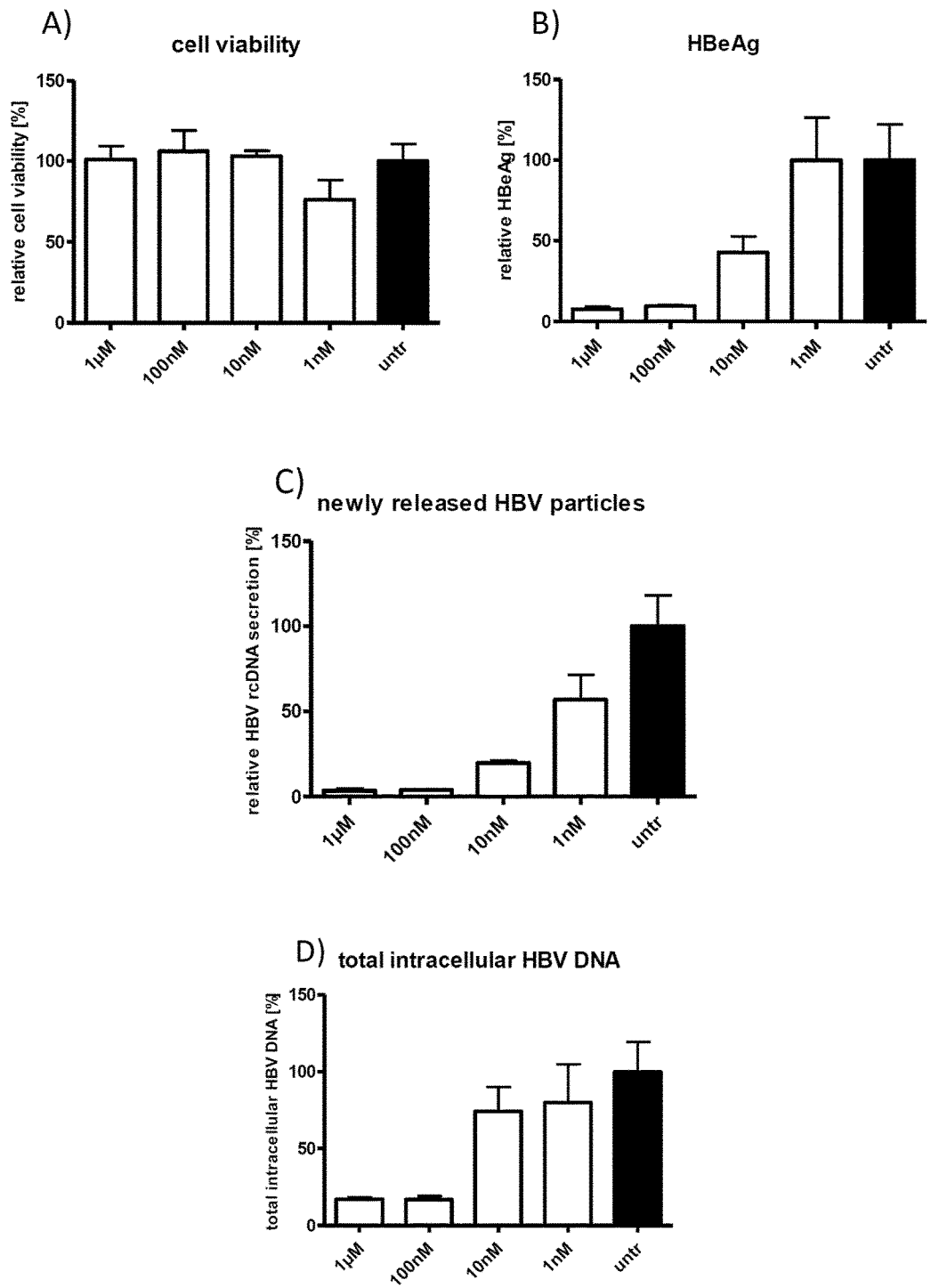

FIG. 4: Antiviral Effect of Compound 1 on HBV Replication in HepG2.2.15 Cells

Antiviral effect of Compound 1 on HBV replication. A) After a three days treatment of HepG2.2.15 cells with Compound 1 in a concentration range from 1 μM to 1 nM, the cell viability was unchanged compared to untreated control cells. B) to D) In contrast to this, all measured viral replication markers like HBeAg, newly released viral particles and intracellular HBV DNA were strongly reduced in a dose dependent fashion (n=3).

Figure 5:
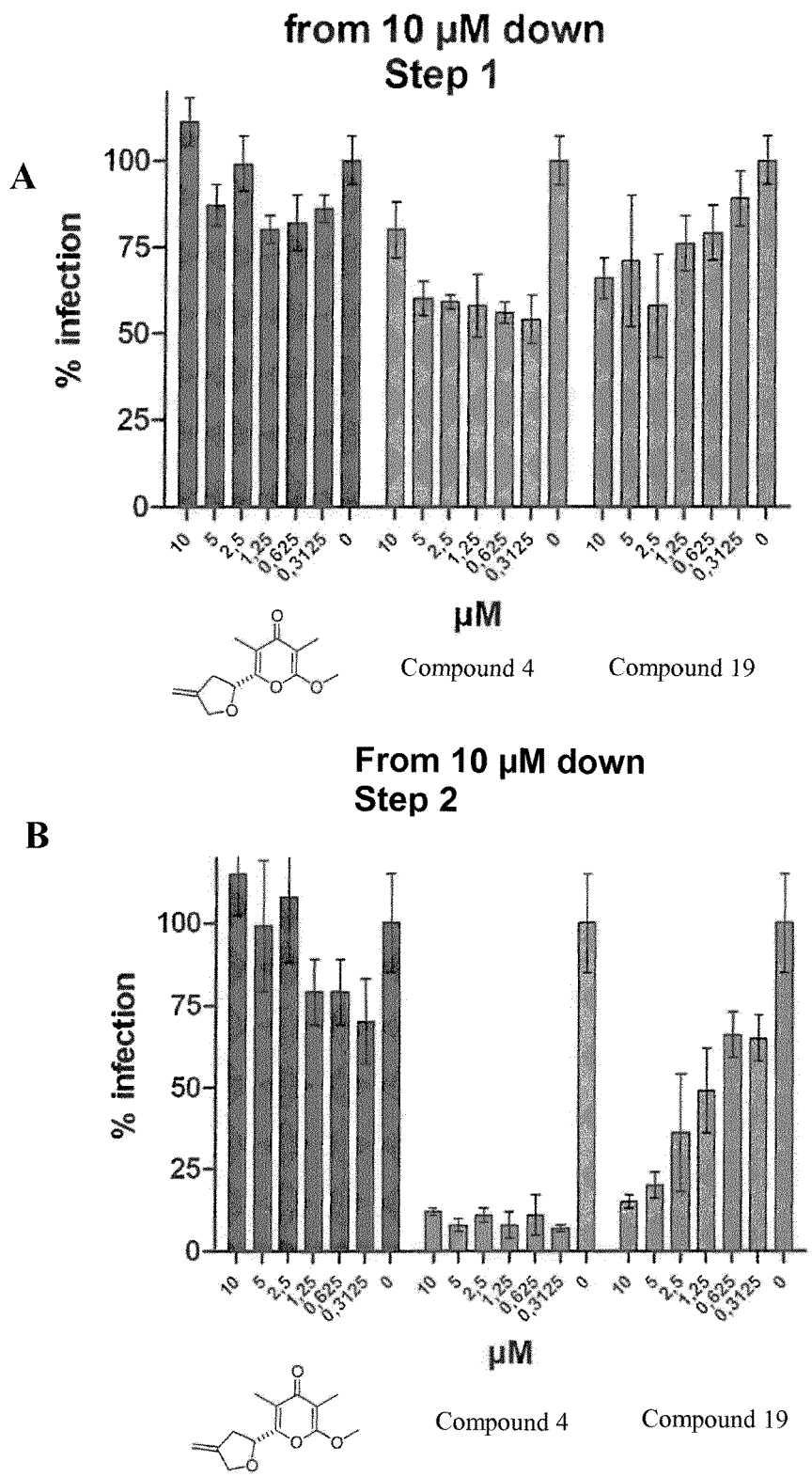
Figure 5:
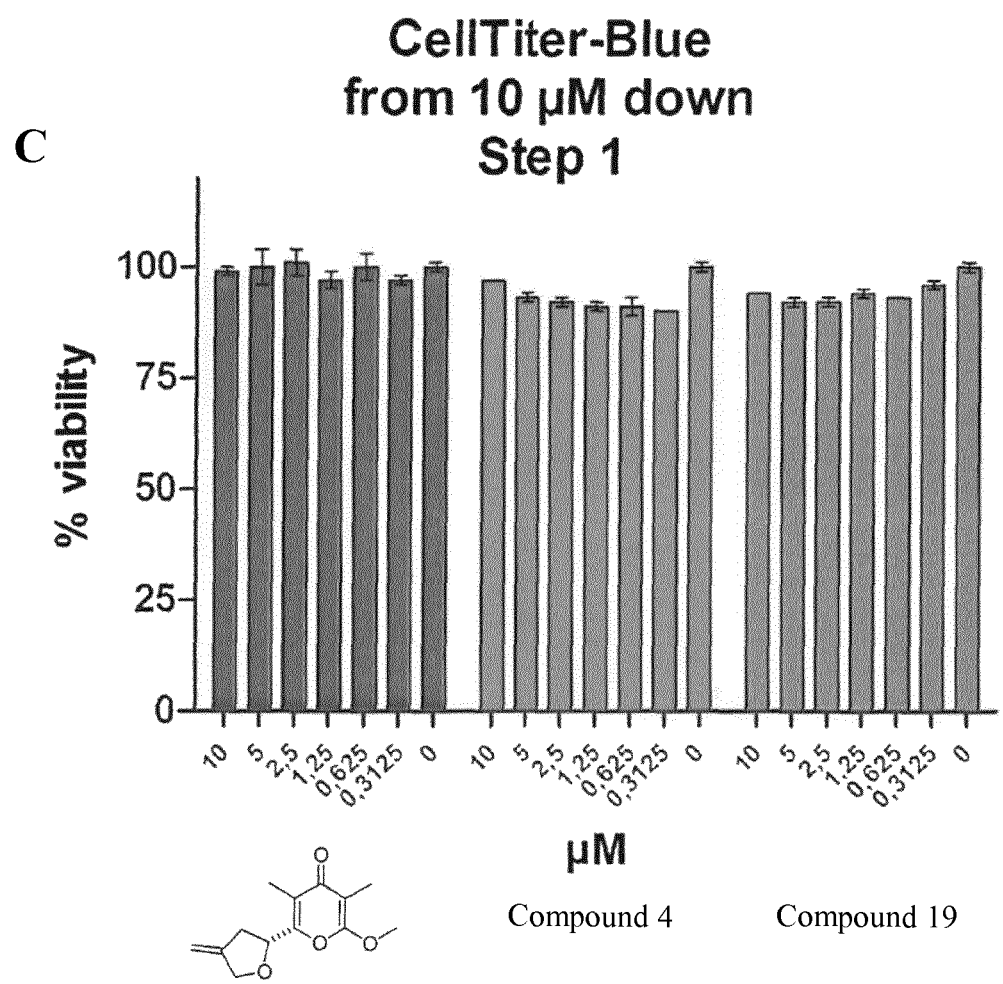

FIG. 5: Efficacies of Anti-HIV-1 Activites of Compounds 4 and 19 in LC5-RIC Cells Exposed to HIV-1 Compared to a Non-active Compound Lacking the Gamma-pyrone Moiety (Depicted Structure).

LC5-RIC cells were exposed to different concentrations of the compounds and HIV-1 inoculum for 48 h and inhibitory effects of compounds on virus replication evaluated in two steps. The first step (FIG. 5A) measured fluorescence signal intensities of the cells in the test cultures. For the second step, aliquots of supernatants of the test cultures were transferred to a new plate with LC5-RIC cells (FIG. 5B) and fluorescent signals were measured 72 h after transfer. Effects of the compounds on the viability of cells in test cultures were analyzed by the CellTiter-Blue assay (FIG. 5C).

Figure 6:
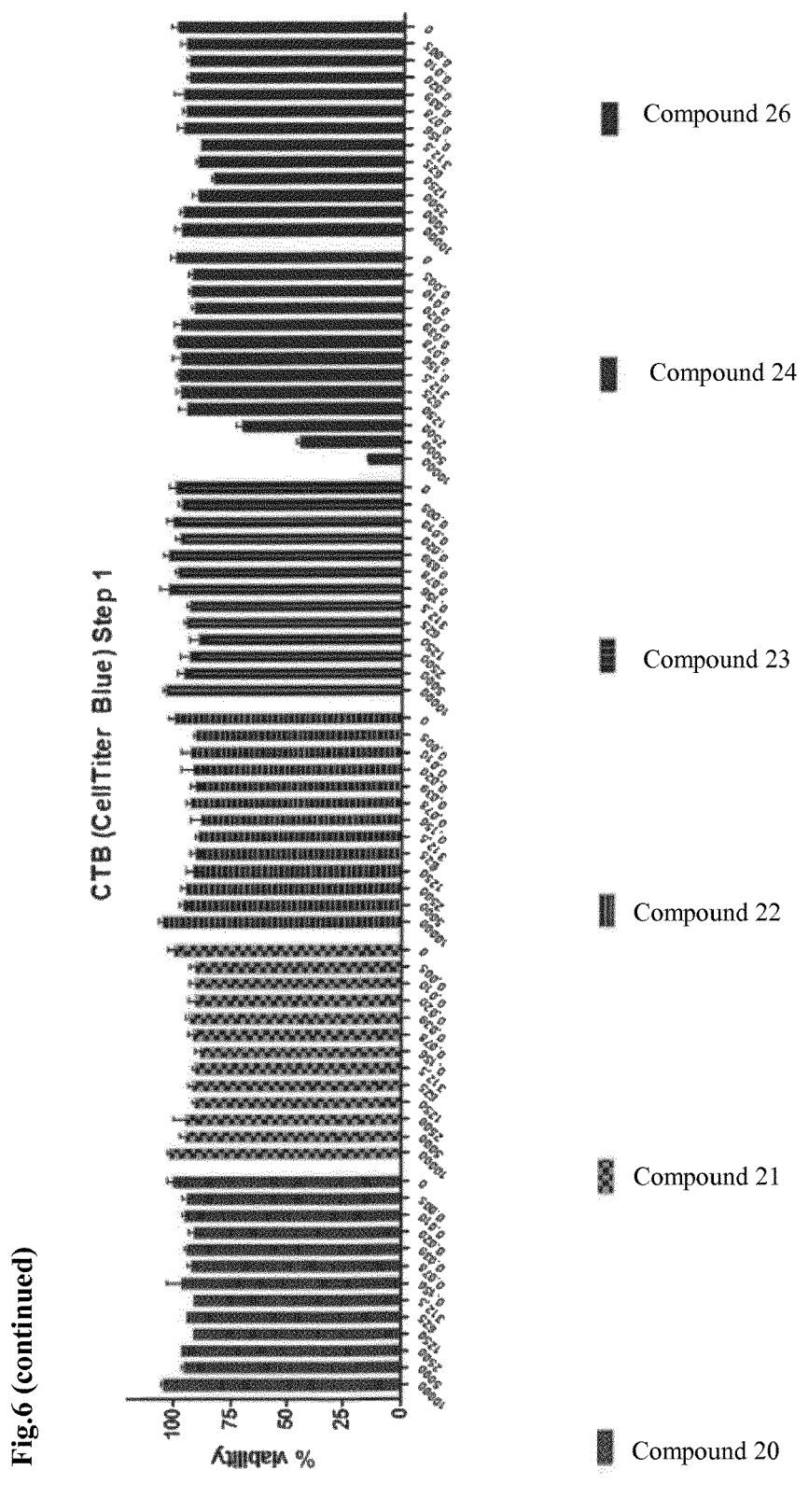

FIG. 6: Efficacies of Anti-HIV-1 Activites of Compounds 20, 21, 22, 23, 24 and 26 in LC5-RIC Cells Exposed to HIV-1.

LC5-RIC cells were exposed to different concentrations of the compounds for 48 h and inhibitory effects of compounds on virus replication evaluated in two steps. The first step (FIG. 6A) measured fluorescence signal intensities of the cells in the test cultures. For the second step, aliquots of supernatants of the test cultures were transferred to a new plate with LC5-RIC cells (FIG. 6B) and fluorescent signals were measured 72 h after transfer. Effects of the compounds on the viability of cells in test cultures were analyzed by the CellTiter-Blue assay (FIG. 6C).

Figure 7:
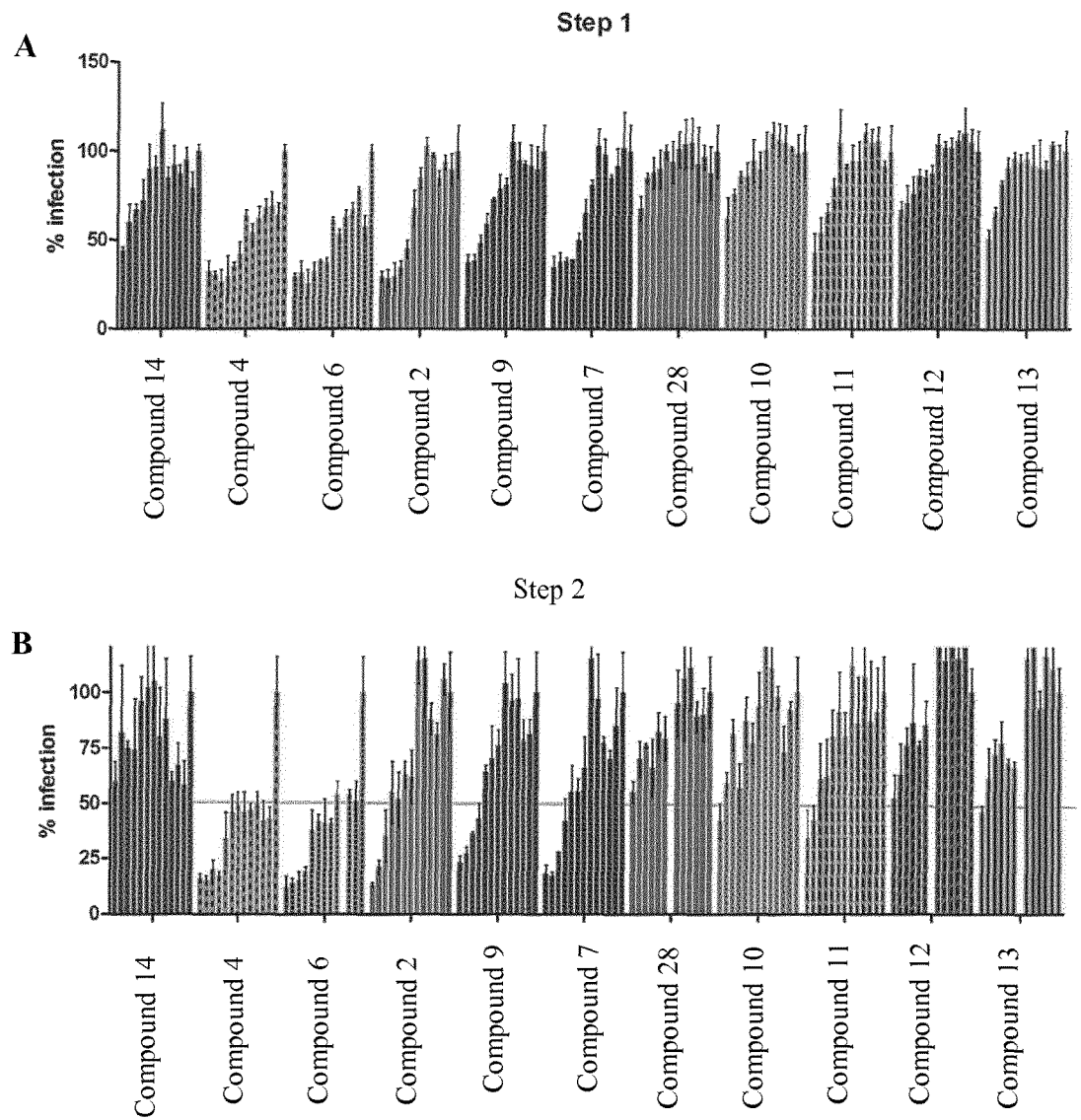
Figure 7:
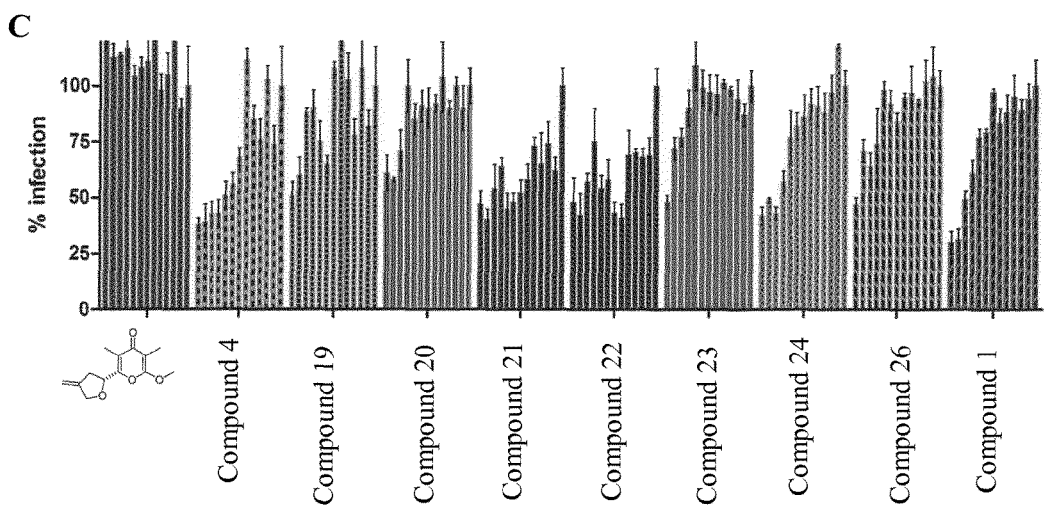
Figure 7:
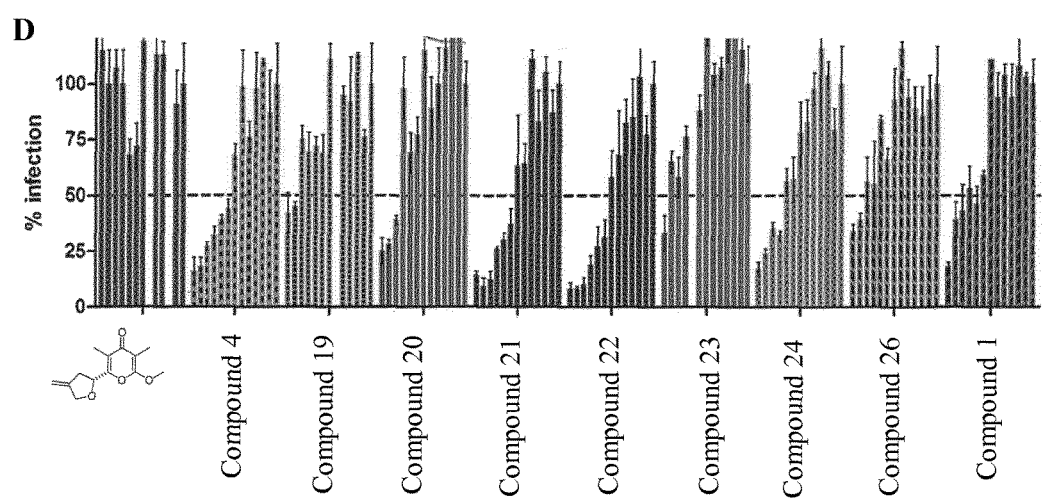

FIG. 7: Efficacies of Anti-HIV-1 Activites of the Indicated Compounds in LC5-RIC Cells Exposed to HIV-1. LC5-RIC cells were exposed to different concentrations of the indicated compounds for 48 h and inhibitory effects of compounds on virus replication evaluated in two steps. The first step (FIGS. 7A, 7C) measured fluorescence signal intensities of the cells in the test cultures. For the second step, aliquots of supernatants of the test cultures were transferred to a new plate with LC5-RIC cells (FIGS. 7B, 7D) and fluorescent signals were measured 72 h after transfer.

Figure 8:
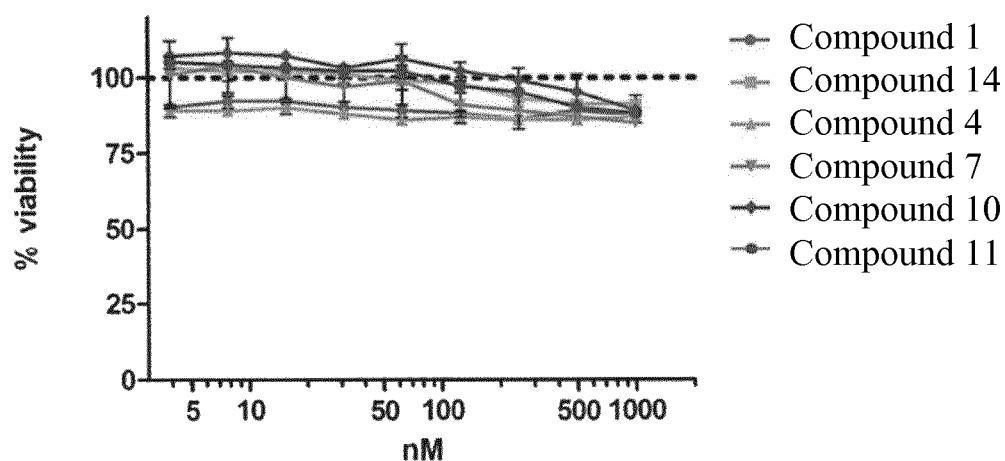
Figure 8:
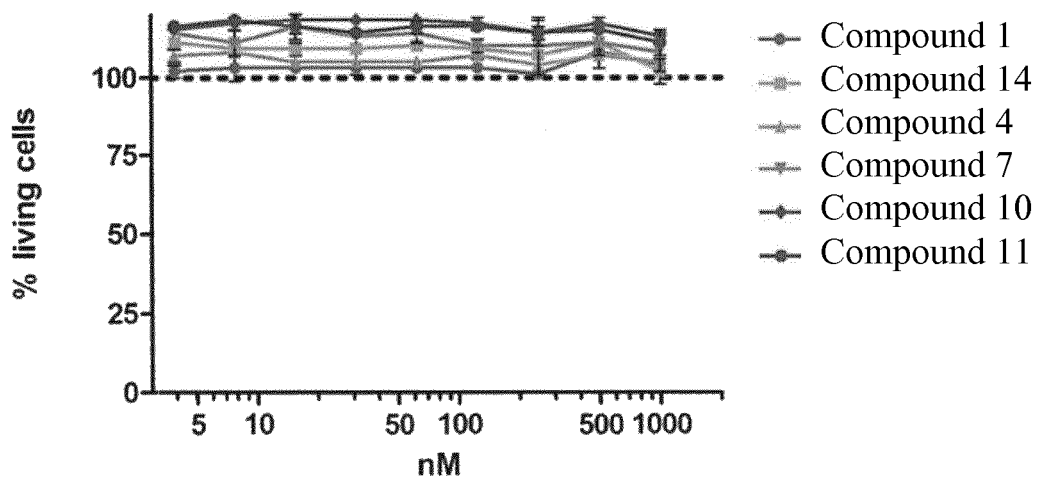

FIG. 8: Effects of Compounds 1, 4, 7, 10, 11 and 14 on the Viability of LC5-RIC Cells.

Effects of the compounds on the viability of LC5-RIC cells were evaluated by CellTiter-Blue assay (FIG. 8A) and the CellTox Green Assay (FIG. 8B).

DETAILED DESCRIPTION OF THE PRESENT INVENTION

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims and other disclosures herein. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment $R^3$ of the compound used in the invention is halogen (such as Cl) and in another embodiment of the compound used in the invention n is 1 or 3, then in a preferred embodiment, $R^3$ of the compound used in the invention is halogen (such as Cl) and n is 1 or 3.

Preferably, the terms used herein are defined as described in "*A multilingual glossary of biotechnological terms: (IUPAC Recommendations)*", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., "*Molecular Cloning: A Laboratory Manual*", $2^{nd}$ Edition, J. Sambrook et al. eds., Cold Spring Harbor Laboratory Press, Cold Spring Harbor 1989).

Throughout this specification and the claims which follow, unless the context requires otherwise, the term "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. For example, a pharmaceutical composition consisting essentially of the members/components as defined herein (such as a pyrone derivative and optionally one additional active compound) would exclude further active compounds (besides the pyrone derivative and the optional one additional active compound) but would not exclude contaminants (e.g., those from the isolation and purification method(s) used to produce the pyrone derivative and/or the optional one additional active compound) in trace amounts (e.g., the amount of the contaminant (preferably the amount of all contaminants present in the composition) is less than 5% by weight, such as less than 4% by weight, 3% by weight, 2% by weight, 1% by weight, 0.5% by weight, 0.1% by weight, with respect to the total composition) and/or pharmaceutically acceptable excipients (such as carriers, e.g., phosphate buffered saline, preservatives, and the like). The term "consisting of" means excluding all other members, integers or steps of significance. For example, a pharmaceutical composition consisting of the members/components as defined herein (such as a pyrone derivative, one excipient, and optionally one additional active compound) would exclude any other compound (including a second or further excipient) in an amount of more than 2% by weight (such as any other compound in an amount of more than 1% by weight, more than 0.5% by weight, more than 0.4% by weight, more than 0.3% by weight, more than 0.2% by weight, more than 0.1% by weight, more than 0.09% by weight, more than 0.08% by weight, more than 0.07% by weight, more than 0.06% by weight, more than 0.05% by weight, more than 0.04% by weight, more than 0.03% by weight, more than 0.02% by weight, more than 0.01% by weight) with respect to the total composition. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 20 carbon atoms, such as from 1 to 12 or from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkyl groups include methyl, ethyl, propyl, iso-propyl, butyl (e.g., n-butyl, iso-butyl, tert-butyl), pentyl (e.g., n-pentyl, iso-pentyl, sec-pentyl, neo-pentyl), 1,2-dimethyl-propyl, iso-amyl, n-hexyl, iso-hexyl, sec-hexyl, 2,2-dimethylbutyl, n-heptyl, iso-heptyl, n-octyl, 2-ethyl-hexyl, n-nonyl, n-decyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkyl include trifluoromethyl, 2,2,2-trichloroethyl, arylalkyl (also called "aralkyl", e.g., benzyl, chloro(phenyl)methyl, 4-methylphenylmethyl, (2,4-dimethylphenyl)methyl, o-fluorophenylmethyl, 2-phenylpropyl, 2-, 3-, or 4-carboxyphenylalkyl), or heteroarylalkyl (also called "heteroaralkyl").

The term "alkenyl" refers to a monoradical of an unsaturated straight or branched hydrocarbon having at least one carbon-carbon double bond. Generally, the maximum number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include ethenyl (i.e., vinyl), 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. An example of a substituted alkenyl is styryl (i.e., 2-phenylvinyl).

The term "alkynyl" refers to a monoradical of an unsaturated straight or branched hydrocarbon having at least one carbon-carbon triple bond. Generally, the maximum number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl (i.e., —C≡CCH$_3$), 2-propynyl (i.e., —CH$_2$CCH or propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom. A "substituted alkynyl" means that one or more (such as 1 to the maximum number of hydrogen atoms bound to an alkynyl group, e.g., 1, 2, 3, 4, 5, 6, 7, 8, 9, or up to 10, such as between 1 to 5, 1 to 4, or 1 to 3, or 1 or 2) hydrogen atoms of the alkynyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl.

The term "aryl" or "aromatic ring" refers to a monoradical of an aromatic cyclic hydrocarbon. Preferably, the aryl group contains 3 to 14 (e.g., 5 to 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. A "substituted aryl" means that one or more (such as 1 to the maximum number of hydrogen atoms bound to an aryl group, e.g., 1, 2, 3, 4, 5, 6, 7, 8, 9, or up to 10, such as between 1 to 5, 1 to 4, or 1 to 3, or 1 or 2) hydrogen atoms of the aryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{th}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted aryl include biphenyl, 2-fluorophenyl, anilinyl, 3-nitrophenyl, 4-hydroxyphenyl, methoxyphenyl (i.e., 2-, 3-, or 4-methoxyphenyl), and 4-ethoxyphenyl.

The term "heteroaryl" or "heteroaromatic ring" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl, pyrrolyl, imidazolyl, pyrazolyl, triazolyl, tetrazolyl, thiazolyl, isothiazolyl, thiadiazolyl, pyridyl, pyrimidinyl, pyrazinyl, triazinyl, benzofuranyl, indolyl, isoindolyl, benzothienyl, 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl, pyridazinyl, phenoxazinyl, thiazolopyridinyl, pyrrolothiazolyl, phenothiazinyl, isobenzofuranyl, chromenyl, xanthenyl, pyrrolizinyl, indolizinyl, indazolyl, purinyl, quinolizinyl, phthalazinyl, naphthyridinyl, cinnolinyl, pteridinyl, carbazolyl, phenanthridinyl, acridinyl, perimidinyl, phenanthrolinyl, and phenazinyl. Exemplary 5- or 6-memered heteroaryl groups include furanyl, thienyl, oxazolyl, isoxazolyl, oxadiazolyl, pyrrolyl, imidazolyl (e.g., 2-imidazolyl), pyrazolyl, triazolyl, tetrazolyl, thiazolyl, isothiazolyl, thiadiazolyl, pyridyl (e.g., 4-pyridyl), pyrimidinyl, pyrazinyl, triazinyl, and pyridazinyl. A "substituted heteroaryl" means that one or more (such as 1 to the maximum number of hydrogen atoms bound to a heteroaryl group, e.g., 1, 2, 3, 4, 5, 6, 7, 8, 9, or up to 10, such as between 1 to 5, 1 to 4, or 1 to 3, or 1 or 2) hydrogen atoms of the heteroaryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted heteroaryl include 3-phenylpyrrolyl, 2,3'-bifuryl, 4-methylpyridyl, 2-, or 3-ethylindolyl.

The term "cycloalkyl" or "cycloaliphatic" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 7 carbon atoms. In one embodiment, the cycloalkyl group has 1, 2, or more (preferably 1 or 2) double bonds. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclopentenyl, cyclohexyl, cyclohexenyl, cyclohexadienyl, cycloheptyl, cyclooctyl, spiro[3,3]heptyl, spiro [3,4]octyl, spiro [4,3]octyl, spiro [4,5]decanyl, bicyclo[4.1.0]heptyl, bicyclo[3.2.0]heptyl, bicyclo[2.2.1]heptyl (i.e., norbornyl), bicyclo[2.2.2]octyl, bicyclo[5.1.0]octyl, bicyclo[4.2.0]octyl, bicyclo[4.3.0]nonyl, 1,2,3,4-tetrahydronaphthyl (i.e., tetralinyl), and bicyclo[4.4.0]decanyl (i.e., decalinyl). A "substituted cycloalkyl" means that one or more (such as 1 to the maximum number of hydrogen atoms bound to a cycloalkyl group, e.g., 1, 2, 3, 4, 5, 6, 7, 8, 9, or up to 10, such as between 1 to 5, 1 to 4, or 1 to 3, or 1 or 2) hydrogen atoms of the cycloalkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted cycloalkyl include oxocyclohexyl, oxocyclopentyl, fluorocyclohexyl, and oxocyclohexenyl.

The term "heterocyclyl" or "heterocyclic ring" means a cycloalkyl group as defined above in which from 1, 2, 3, or 4 carbon atoms in the cycloalkyl group are replaced by heteroatoms of oxygen, nitrogen, silicon, selenium, phosphorous, or sulfur, preferably O, S, or N. A heterocyclyl group has preferably 1 or 2 rings containing from 3 to 10, such as 3, 4, 5, 6, or 7, ring atoms. Preferably, in each ring of the heterocyclyl group the maximum number of O atoms is 1, the maximum number of S atoms is 1, and the maximum total number of 0 and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholinyl, pyrrolidinyl, imidazolidinyl, pyrazolidinyl, piperidinyl (also called piperidyl), piperazinyl, di- and tetrahydrofuranyl, di- and tetrahydrothienyl, di- and tetrahydropyranyl, urotropinyl, lactones, lactams, cyclic imides, and cyclic anhydrides. A "substituted heterocyclyl" means that one or more (such as 1 to the maximum number of hydrogen atoms bound to a heterocyclyl group, e.g., 1, 2, 3, 4, 5, 6, 7, 8, 9, or up to 10, such as between 1 to 5, 1 to 4, or 1 to 3, or 1 or 2) hydrogen atoms of the heterocyclyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{th}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl).

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The term "5-to 8-membered ring" means a cycloaliphatic, aromatic, heterocyclic or heteroaromatic ring as defined above which is condensed with the phenyl group of formula (I) or (II) and which has 5, 6, 7, or 8, preferably 6 ring atoms. In one embodiment, the 5-to 8-membered ring is cycloaliphatic. In another embodiment, the 5-to 8-membered ring is aromatic. For example, in case the 5-to 8-membered ring is an aromatic ring having 6 carbon atoms, said ring together with the phenyl group of formula (I) or (II) form a naphthyl moiety. The 5-to 8-membered ring may be substituted, i.e., so that one or more (such as 1 to the maximum number of hydrogen atoms bound to the 5-to 8-membered ring, e.g., 1, 2, 3, 4, 5, or 6, such as between 1 to 5, 1 to 4, or 1 to 3, or 1 or 2) hydrogen atoms of the 5-to 8-membered ring are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl).

The term "halogen" or "halo" means fluoro, chloro, bromo, or iodo. The term "hydroxy" means OH. The term "nitro" means NO$_2$. The term "cyano" means the group —CN. The term "isocyano" means the group —NC. The term "cyanato" means the group —OCN. The term "isocyanato" means the group —NCO. The term "thiocyanato" means the group —SCN. The term "isothiocyanato" means the group —NCS. The term "azido" means N$_3$. The term "phosphoryl" means a monoradical of a phosphor containing group (such as OP(OR$^{11}$)$_3$ or OP(hal)$_3$, wherein hal is halogen, e.g., Cl or Br). Examples of a phosphoryl group include —O(O)P(OR$^{11}$)$_2$ and —P(O)Cl$_2$.

The term "optionally substituted" indicates that one or more (such as 1 to the maximum number of hydrogen atoms bound to a moiety, e.g., 1, 2, 3, 4, 5, 6, 7, 8, 9, or up to 10, such as between 1 to 5, 1 to 4, or 1 to 3, or 1 or 2) hydrogen atom(s) may be replaced with a group (i.e., a $1^{st}$ level substituent) different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 3-to 14-membered aryl), heteroaryl (preferably, 3-to 14-membered heteroaryl), cycloalkyl (preferably, 3-to 14-membered cycloalkyl), heterocyclyl (preferably, 3-to 14-membered heterocyclyl), halogen, —CN, —NC, —NCO, —CNO, —SCN, —NCS, —N$_3$, —NO$_2$, —OR$^{71}$, —N(R$^{72}$)(R$^{73}$), —ON(R$^{72}$)(R$^{73}$), —N$^+$(—O)(R$^{72}$)(R$^{73}$), —S(O)$_{0-2}$R$^{71}$ (i.e., —SR$^{71}$, —S(O)R$^{71}$, or —S(O)$_2$R$^{71}$), —S(O)$_{0-2}$OR$^{71}$ (e.g., —S(O)$_{1-2}$OR$^{71}$), —OS(O)$_{0-2}$OR$^{71}$ (e.g., —OS(O)$_{1-2}$OR$^{71}$), —S(O)$_{0-2}$N(R$^{72}$)(R$^{73}$) (e.g., —S(O)$_{1-2}$N(R$^{72}$)(R$^{73}$)), —OS(O)$_{0-2}$N(R$^{72}$)(R$^{73}$) (e.g., —OS(O)$_{1-2}$N(R$^{72}$)(R$^{73}$)), —N(R$^{71}$)S(O)$_{0-2}$R$^{71}$ (e.g., —N(R$^{71}$)S(O)$_{1-2}$R$^{71}$), —NR$^{71}$S(O)$_{0-2}$OR$^{71}$ (e.g., —NR$^{71}$S(O)$_{1-2}$OR$^{71}$), —NR$^{71}$S(O)$_{0-2}$N(R$^{72}$)(R$^{73}$) (e.g., —NR$^{71}$S(O)$_{1-2}$N(R$^{72}$)(R$^{73}$)), —C(=X$^1$)

$R^{71}$, —C(=$X^1$)$X^1R^{71}$, —$X^1$C(=$X^1$)$R^{71}$, and —$X^1$C(=$X^1$)$X^1R^{71}$, and/or any two 1$^{st}$ level substituents which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups of the 1$^{st}$ level substituent may themselves be substituted by one or more (e.g., one, two or three) substituents (i.e., 2$^{nd}$ level substituents) selected from the group consisting of $C_{1-6}$ alkyl, $C_{2-6}$ alkenyl, $C_{2-6}$ alkynyl, 3-to 14-membered aryl, 3-to 14-membered heteroaryl, 3-to 14-membered cycloalkyl, 3-to 14-membered heterocyclyl, halogen, —$CF_3$, —CN, —NC, —NCO, —CNO, —SCN, —NCS, —$N_3$, —$NO_2$, —$OR^{81}$, —$N(R^{82})(R^{83})$, —$ON(R^{82})(R^{83})$, —$N^+$(—O)($R^{82}$)($R^{83}$), —$S(O)_{0-2}R^{81}$ (i.e., —$SR^{81}$, —$S(O)R^{81}$, or —$S(O)_2R^{81}$), —$S(O)_{0-2}OR^{81}$ (e.g., —$S(O)_{1-2}OR^{81}$), —$OS(O)_{0-2}R^{81}$ (e.g., —$OS(O)_{1-2}R^{81}$), —$OS(O)_{0-2}OR^{81}$ (e.g., —$OS(O)_{1-2}OR^{81}$), —$S(O)_{0-2}N(R^{82})(R^{83})$ (e.g., —$S(O)_{1-2}N(R^{82})(R^{83})$), —$OS(O)_{0-2}N(R^{82})(R^{83})$ (e.g., —$OS(O)_{1-2}N(R^{82})(R^{83})$), —$N(R^{81})S(O)_{0-2}R^{81}$ (e.g., —$N(R^{81})S(O)_{1-2}R^{81}$), —$NR^{81}S(O)_{0-2}OR^{81}$ (e.g., —$NR^{81}S(O)_{1-2}OR^{81}$), —$NR^{81}S(O)_{0-2}N(R^{82})(R^{83})$ (e.g., —$NR^{81}S(O)_{12}N(R^{82})(R^{83})$), —C(=$X^2$)$R^{81}$, —C(=$X^2$)$X^2R^{81}$, —$X^2$C(=$X^2$)$R^{81}$, and —$X^2$C(=$X^2$)$X^2R^{81}$, and/or any two 2$^{nd}$ level substituents which are bound to the same carbon atom of a cycloalkyl or heterocyclyl group may join together to form =$X^2$, wherein each of the $C_{1-6}$ alkyl, $C_{2-6}$ alkenyl, $C_{2-6}$ alkynyl, 3-to 14-membered aryl, 3-to 14-membered heteroaryl, 3-to 14-membered cycloalkyl, 3-to 14-membered heterocyclyl groups of the 2$^{nd}$ level substituent is optionally substituted with one or more (e.g., one, two or three) substituents (i.e., 3$^{rd}$ level substituents) independently selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$alkyl), —N($C_{1-3}$ alkyl)$_2$, —NHS(O)$_2$($C_{1-3}$alkyl), —S(O)$_2NH_{2-z}$($C_{1-3}$ alkyl)$_z$, —C(=O)($C_{1-3}$alkyl), —C(=O)OH, —C(=O)O($C_{1-3}$ alkyl), —C(=O)$NH_{2-z}$($C_{1-3}$ alkyl)$_z$, —OC(=O)($C_{1-3}$ alkyl), —OC(=O)O($C_{1-3}$ alkyl), —OC(=O)$NH_{2-z}$($C_{1-3}$alkyl)$_z$, —NHC(=O)($C_{1-3}$alkyl), —NHC(=O)$NH_{z-2}$($C_{1-3}$alkyl)$_z$, —NHC(=NH)$NH_{z-2}$($C_{1-3}$alkyl)$_z$, and —N($C_{1-3}$alkyl)C(=NH)$NH_{2-z}$($C_{1-3}$alkyl)$_z$, wherein z is 0, 1, or 2 and $C_{1-3}$ alkyl is methyl, ethyl, propyl or isopropyl, and/or any two 3$^{rd}$ level substituents which are bound to the same carbon atom of a cycloalkyl or heterocyclyl group may join together to form =O, =S, =NH, or =N($C_{1-3}$ alkyl); wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3-to 7-membered cycloalkyl, 5- or 6-membered aryl, 5- or 6-membered heteroaryl, and 3-to 7-membered heterocyclyl, wherein each of the $C_{1-6}$ alkyl, $C_{2-6}$ alkenyl, $C_{2-6}$ alkynyl, 3-to 7-membered cycloalkyl, 5- or 6-membered aryl, 5- or 6-membered heteroaryl, and 3-to 7-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)($C_{1-3}$ alkyl), —C(=O)OH, —C(=O)O($C_{1-3}$ alkyl), —C(=O)$NH_{2-z}$($C_{1-3}$ alkyl)$_z$, —OC(=O)($C_{1-3}$ alkyl), —OC(=O)O($C_{1-3}$ alkyl), —OC(=O)$NH_{2-z}$($C_{1-3}$ alkyl)$_z$, —NHC(=O)($C_{1-3}$ alkyl), —NHC(=O)$NH_{z-2}$($C_{1-3}$ alkyl)$_z$, —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl, or $R^{72}$ and $R^{73}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)($C_{1-3}$ alkyl), —C(=O)OH, —C(=O)O($C_{1-3}$ alkyl), —C(=O)$NH_{2-z}$($C_{1-3}$ alkyl)$_z$, —OC(=O)($C_{1-3}$ alkyl), —OC(=O)O($C_{1-3}$ alkyl), —OC(=O)$NH_{2-z}$($C_{1-3}$ alkyl)$_z$, —NHC(=O)($C_{1-3}$ alkyl), —NHC(=O)$NH_{z-2}$($C_{1-3}$ alkyl)$_z$, —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3-to 6-membered cycloalkyl, 5- or 6-membered aryl, 5- or 6-membered heteroaryl, and 3-to 6-membered heterocyclyl, wherein each of the $C_{1-4}$ alkyl, $C_{2-4}$ alkenyl, $C_{2-4}$ alkynyl, 3-to 6-membered cycloalkyl, 5- or 6-membered aryl, 5- or 6-membered heteroaryl, and 3-to 6-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)($C_{1-3}$ alkyl), —C(=O)OH, —C(=O)O($C_{1-3}$ alkyl), —C(=O)$NH_{2-z}$($C_{1-3}$ alkyl)$_z$, —OC(=O)($C_{1-3}$ alkyl), —OC(=O)O($C_{1-3}$ alkyl), —OC(=O)$NH_{2-z}$($C_{1-3}$ alkyl)$_z$, —NHC(=O)($C_{1-3}$ alkyl), —NHC(=O)$NH_{z-2}$($C_{1-3}$ alkyl)$_z$, —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl, or $R^{82}$ and $R^{83}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)($C_{1-3}$ alkyl), —C(=O)OH, —C(=O)O($C_{1-3}$ alkyl), —C(=O)$NH_{2-z}$($C_{1-3}$ alkyl)$_z$, —OC(=O)($C_{1-3}$ alkyl), —OC(=O)O($C_{1-3}$ alkyl), —OC(=O)$NH_{2-z}$($C_{1-3}$ alkyl)$_z$, —NHC(=O)($C_{1-3}$ alkyl), —NHC(=O)$NH_{z-2}$($C_{1-3}$ alkyl)$_z$, —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl;

$X^1$ and $X^2$ are independently selected from O, S, and N($R^{84}$), wherein $R^{84}$ is —H or $C_{1-3}$ alkyl.

Typical 1$^{st}$ level substituents are preferably selected from the group consisting of $C_{1-6}$ alkyl, $C_{2-6}$ alkenyl, $C_{2-6}$ alkynyl, 3-to 14-membered (such as 5- or 6-membered) aryl, 3-to 14-membered (such as 5- or 6-membered) heteroaryl, 3-to 14-membered (such as 3-to 7-membered) cycloalkyl, 3-to 14-membered (such as 3-to 7-membered) heterocyclyl, halogen, —CN, —NC, —NCO, —CNO, —SCN, —NCS, —$N_3$, —$NO_2$, —$OR^{71}$, —$N(R^{72})(R^{73})$, —$S(O)_{0-2}R^{71}$, —$S(O)_{0-2}OR^{71}$, —$OS(O)_{0-2}R^{71}$, —$OS(O)_{0-2}OR^{71}$, —$S(O)_{0-2}N(R^{72})(R^{73})$, —$OS(O)_{0-2}N(R^{72})(R^{73})$, —$N(R^{71})S(O)_{0-2}R^{71}$, —$NR^{71}S(O)_{0-2}OR^{71}$, —C(=$X^1$)$R^{71}$, —C(=$X^1$)$X^1R^{71}$, —$X^1$C(=$X^1$)$R^{71}$, and —$X^1$C(=$X^1$)$X^1R^{71}$, such as $C_{1-4}$ alkyl, $C_{2-4}$ alkenyl, $C_{2-4}$ alkynyl, 5- or 6-membered aryl, 5- or 6-membered heteroaryl, 3-to 7-membered cycloalkyl, 3-to 7-membered heterocyclyl, halogen, —$CF_3$, —CN, —NC, —NCO, —CNO, —SCN, —NCS, —N$_3$, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; X$^1$ is independently selected from O, S, NH and N(CH$_3$); and R$^{71}$, R$^{72}$, and R$^{73}$ are as defined above or, preferably, are independently selected from the group consisting of —H, C$_{1-4}$ alkyl, C$_{2-4}$ alkenyl, C$_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl), —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; or R$^{72}$ and R$^{73}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl), —NHS(O)$_2$ (C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl.

Typical 2$^{nd}$ level substituents are preferably selected from the group consisting of C$_{1-4}$ alkyl, C$_{2-4}$ alkenyl, C$_{2-4}$ alkynyl, 5- or 6-membered aryl, 5- or 6-membered heteroaryl, 5- or 6-membered cycloalkyl, 5- or 6-membered heterocyclyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH) NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl. Particularly preferred 2$^{nd}$ level substituents include 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —CH$_2$CH$_2$OCH$_3$, —OCH$_2$CH$_2$OCH$_3$, —CH$_2$CH$_2$NH$_{2-z}$(CH$_3$)$_z$, —OCH$_2$CH$_2$NH$_{2-z}$(CH$_3$)$_z$, —CF$_3$, and —OCF$_3$.

Typical 3$^{th}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, C$_{1-3}$ alkyl, halogen, —NC, —NCO, —CNO, —SCN, —NCS, —N$_3$, —CF$_3$, —OH, —OCH$_3$, —OCF$_3$, —SCH$_3$, —NH$_{2-z}$(CH$_3$)$_z$, —C(=O)OH, and —C(=O)OCH$_3$, wherein z is 0, 1, or 2.

The term "molecular probe" means an atom or molecule which can be attached to a compound of interest (e.g., a pyrone derivative of formula (I) or (II)) in order to label said compound (i.e., resulting in a labeled compound of interest). For example, the molecular probe can be radioactive or luminescent (e.g., fluorescent), or can comprise one member of a complementary binding pair. Thus, depending on the particular molecular probe used, the labeled compound can be detected by (i) measuring the radioactivity emitted by the labeled compound, (ii) measuring the radiation (e.g., fluorescence) emitted by the labeled compound (optionally after having applied radiation of a wavelength suitable for excitation of the molecular probe), or (iii) using the second member of the complementary binding pair. Examples of radioactive molecular probes include a radioisotope (e.g., $^3$H, $^{14}$C, $^{32}$P, $^{57}$Co, $^{60}$Co, $^{90}$Sr, $^{99m}$Tc, $^{111}$In, $^{113m}$In, $^{123}$I, $^{124}$I, $^{131}$I, $^{153}$Gd, $^{137}$CS) and a group (such as a 1$^{st}$, 2$^{nd}$, or 3$^{rd}$ level substituent as specified herein) containing one or more of said radioisotopes (preferably one or more of $^3$H, $^{14}$C, and $^{32}$P), such as $^{14}$CH$_3$ or CH$_2$CH$_2$($^3$H). Examples of fluorescent molecular probes include fluorescent dyes and fluorescent labels. Exemplary complementary binding pairs are streptavidin and biotin, an antibody and the antigen to which the antibody binds, and an anticalin and the antigen to which the anticalin binds. The molecular probe does not abolish the activity of the compound of interest (e.g., the therapeutic activity of a pyrone derivative of formula (I) or (II)) against a condition, disorder or disease that is mediated or caused by an animal pathogenic virus as defined herein. Preferably, the activity of the labeled compound of interest is at least 50%, at least 60%, at least 70%, at least 80%, at least 90%, at least 95%, at least 98%, at least 99% of the activity of the unlabeled compound of interest. In one embodiment, the activity of the labeled compound of interest is substantially identical to the activity of the unlabeled compound of interest. In one embodiment, the activity of the labeled compound of interest is identical to or higher than the activity of the unlabeled compound of interest.

The term "anticalin" means a protein that is able to bind to an antigen and has a molecular weight up to 20 kDa. Anticalins are not structurally related to antibodies. In particular, anticalins have a barrel structure which is formed by eight antiparallel β-strands pairwise connected by loops and an attached α-helix and which they share with naturally occurring lipocalins. Due to their ability to bind antigens anticalins are sometimes called antibody mimetics. See, e.g., Skerra, A., *FEBS J.* 275 (2008), 2677-2683.

The term "antigen" relates to an agent such as a protein or peptide comprising an epitope against which an immune response is directed and/or is to be directed. In a preferred embodiment, an antigen is a viral antigen, i.e., a constituent of a virus which may be derived from the capsid, the envelop, or a nucleoprotein, in particular those antigens which are produced, preferably in large quantity, intracellular or as surface antigens on cells infected with the virus.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules (such as amino acids or sugar side chains) and usually have specific three dimensional structural characteristics, as well as specific charge characteristics. Conformational and non-conformational epitopes are distinguished in that the binding to the former but not the latter is lost in the presence of denaturing solvents. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies, and antibody derivatives. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies may be derived from different species, including but not limited to mouse, rat, rabbit, guinea pig and human.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However, the definition is not limited to this particular example.

The term "antibody derivatives" refers to any modified form of an antibody, e.g., a conjugate of the antibody and another agent or antibody, or an antibody fragment. In this respect, the term "conjugate" means that at least two substances (e.g., an antibody and another agent, e.g., a fluorescent label) are attached to each other, preferably by one or more covalent linkages. Exemplary linkages are given below within the section concerning fluorescent labels.

The term "antibody fragment" refers to one or more fragments of an antibody that retain the ability to specifically bind to an antigen. It has been shown that the antigen-binding function of an antibody can be performed by fragments of a full-length antibody. Examples of antibody fragments include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883).

The term "folic acid" which is also known as vitamin B9, vitamin Bc, pteroyl-L-glutamic acid, or pteroyl-L-glutamate means (2S)-2-[(4-{[(2-amino-4-hydroxypteridin-6-yl)methyl]amino}phenyl)-formamido]pentanedioic acid having the formula

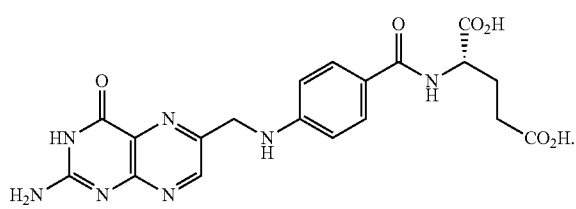 [SMILES: Nc1nc2ncc(CNc3ccc(C(=O)N[C@@H](CCC(=O)O)C(=O)O)cc3)nc2c(=O)[nH]1]

The term "fluorescent dye" means a fluorescent chemical compound which is able to absorb light energy of a specific wavelength and emit light at a longer wavelength. The emission of light by fluorescence dyes at a longer wavelength usually occurs immediately in contrast to phosphorescence dyes. For a comprehensive review on fluorescence dyes, their use and labeling of compounds with said dyes see e.g., "*The Molecular Probes® Handbook—A Guide to Fluorescent Probes and Labeling Technology*", Iain Johnson and Michelle T. Z. Spence (Editors), 11th Edition (2010).

The term "fluorescent label" means a reactive derivative of a fluorescent dye. Preferably, the fluorescent label is capable of binding to a functional group contained in a compound of interest (e.g., a pyrone derivative of formula (I) or (II)). In one embodiment, the fluorescent label comprises an electrophilic group which is capable of reacting with a nucleophilic group contained in a compound of interest. In another embodiment, the fluorescent label comprises a nucleophilic group which is capable of reacting with an electrophilic group contained in a compound of interest. Suitable pairs of electrophilic and nucleophilic groups are known to the skilled person and include activated ester/amines (resulting in carboxamide linkages), acyl halides/amines (resulting in carboxamide linkages), acyl halides/alcohols (resulting in ester linkages), aldehydes/amines (resulting in imine linkages), alkyl halides/amines (resulting in alkyl amine linkages), alkyl halides/thiols (resulting in thio ether linkages), anhydrides/alcohols (resulting in ester linkages), epoxides/thiols (resulting in thioether linkages), haloacetamides/thiols (resulting in thioether linkages), isocyanates/amines (resulting in urea linkages), isocyanates/alcohols (resulting in urethane linkages), isothiocyanates/amines (resulting in thiourea linkages), maleimides/thiols (resulting in thioether linkages), silyl halides/alcohols (resulting in silyl ether linkages), and sulfonyl halides/amines (resulting in sulfonamide linkages). Examples of activated esters include succinimidyl esters, sulfosuccinimidyl esters, and benzotriazolyl esters. For example, "*The Molecular Probes® Handbook—A Guide to Fluorescent Probes and Labeling Technology*", supra, gives guidance and examples for means and conditions for attaching a fluorescent label to a compound of interest.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are not enantiomers. "Tautomers" are structural isomers of the same chemical substance that spontaneously interconvert with each other, even when pure.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds described herein (in particular, the pyrone derivatives of formula (I) or (II)) include deuterium, $^{11}C$, $^{13}C$, $^{14}C$, $^{15}N$, $^{18}F$, $^{32}S$, $^{36}Cl$, and $^{125}I$. The term "isotopically enriched" means that the occurrence of the isotope is beyond the natural abundance.

The term "half-life" relates to the period of time which is needed to eliminate half of the activity, amount, or number of molecules. In the context of the present invention, the half-life of a compound of formula (I) or (II) is indicative for the stability of said compound.

In case a structural formula shown in the present application can be interpreted to encompass more than one isomer, said structural formula, unless explicitly stated otherwise, encompasses all possible isomers, and hence each individual such isomer. For example, a compound of formula (I) encompasses both isomers, i.e., the isomer having the following formula (Ia) and the isomer having the following formula (Ib):

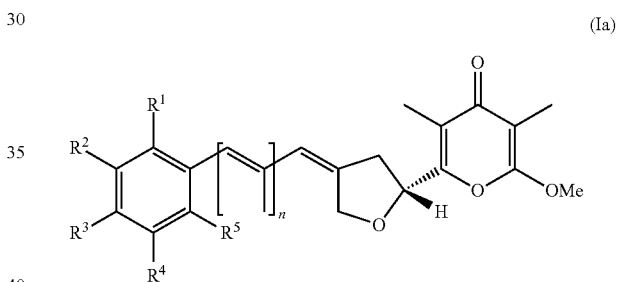

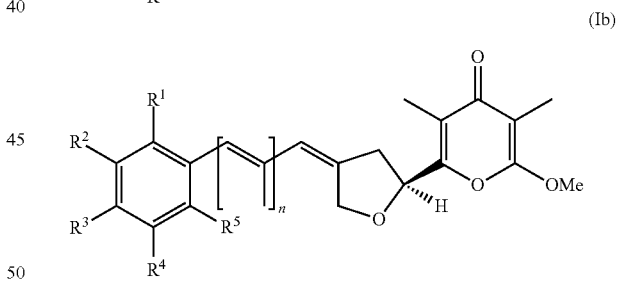

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:

solvent effects (the packing of crystal may be different in polar and nonpolar solvents);
certain impurities inhibiting growth pattern and favor the growth of a metastable polymorphs;

the level of supersaturation from which material is crystallized (in which generally the higher the concentration above the solubility, the more likelihood of metastable formation);

temperature at which crystallization is carried out;

geometry of covalent bonds (differences leading to conformational polymorphism);

change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a compound of the present invention) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them.

The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form.

The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

The term "naturally occurring", as used herein in context with an object, refers to the fact that an object can be found in nature. For example, a polypeptide or polynucleotide sequence that is present in an organism (including viruses) that can be isolated from a source in nature and which has not been intentionally modified by man in the laboratory is naturally occurring.

By "treat" is meant to administer a compound or composition or a combination of compounds or compositions (e.g., pharmaceutical compositions) to a subject in order to eliminate a condition, disorder or disease; arrest or slow a condition, disorder or disease in a subject; decrease the frequency or severity of symptoms and/or recurrences in a subject who currently has or who previously has had a condition, disorder or disease (e.g., by reducing the number of virus particles in a subject); and/or prolong, i.e. increase the lifespan of the subject. In particular, the term "treating a condition, disorder or disease" includes curing, shortening the duration, ameliorating, slowing down or inhibiting progression or worsening, of a condition, disorder or disease or the symptoms of said condition, disorder or disease.

According to the present invention, terms such as "protect", "prevent", "prophylactic", "preventive", or "protective" relate to the prevention of the occurrence and/or the propagation of a condition, disorder or disease in a subject and, in particular, to minimizing the chance that a subject will develop a condition, disorder or disease or to delaying the onset or development of a condition, disorder or disease (e.g., by inhibiting or slowing the development of a new condition, disorder or disease in a subject). For example, a person at risk for being infected with a virus would be a candidate for therapy to prevent the infection with said virus.

By "being at risk" is meant a subject that is identified as having a higher than normal chance of developing a condition, disorder or disease (in particular, a condition, disorder or disease that is mediated or caused by an animal pathogenic virus) compared to the general population. In addition, a subject who has had, or who currently has, a condition, disorder or disease (in particular, a condition, disorder or disease that is mediated or caused by an animal pathogenic virus), is a subject who has an increased risk for developing a condition, disorder or disease, as such a subject may continue to develop a condition, disorder or disease.

The term "animal pathogenic virus" refers to a virus which can infect a subject and which cause or mediate a condition, disorder or disease in said subject. Examples of animal pathogenic viruses include viruses belonging to the following families: Adenoviridae, Herpesviridae, Papillomaviridae, Polyomaviridae, Poxviridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, and Reoviridae.

The family Adenoviridae can be subdivided into the genera mastadenovirus, aviadenovirus, atadenovirus, siadenovirus, and ichtadenovirus. Examples of mastadenoviruses include all human adenoviruses (such as human adenovirus A, humanadenovirus B, humanadenovirus C, humanadenovirus D, humanadenovirus E, human adenovirus F, humanadenovirus G), bovineadenovirus A, bovineadenovirus B, bovineadenovirus C, canineadenovirus, equineadenovirus A, equineadenovirus B, murineadenovirus A, ovineadenovirus A, ovineadenovirus B, porcineadenovirus A, porcineadenovirus B, porcineadenovirus C, tree shrew adenovirus, caprineadenovirus (goat adenovirus 2), guinea pig adenovirus 1, murineadenovirus B, ovineadenovirus C, and simianadenovirus, squirrel adenovirus 1. Examples of aviadenoviruses include falcon adenovirus A, fowl adenovirus A, fowl adenovirus B, fowl adenovirus C, fowl adenovirus D, fowl adenovirus E, goose adenovirus A, and turkey adenovirus B. Examples of atadenoviruses include bovine adenovirus D (e.g., bovine adenovirus 4, bovine adenovirus 5, bovine adenovirus 8), duck adenovirus A (e.g., duck adenovirus 1), ovine adenovirus D (e.g., goat adenovirus 1, ovine adenovirus 7), possum adenovirus (e.g., possum adenovirus 1), agamid adenovirus 1, agamid atadenovirus Ben, agamid atadenovirus Well, bovine adenovirus E, bovine adenovirus F, cervine adenovirus, chameleon adenovirus, eublepharid adenovirus 1, gekko adenovirus, helodermatid adenovirus 1, scincid adenovirus 1, and snake adenovirus. Examples of siadenoviruses include frog adenovirus 1 and turkey adenovirus A. An example of ichtadenoviruses is sturgeon adenovirus A.

The family Herpesviridae can be subdivided into Alphaherpesvirinae (including the genera simplexvirus, varicellovirus, mardivirus, and iltovirus), Betaherpesvirinae (including the genera cytomegalovirus, muromegalovirus, proboscivirus, and roseolovirus), and Gammaherpesvirinae (including the lymphocryptovirus, macavirus, percavirus, and rhadinovirus). Examples of simplexviruses include herpes simplex virus 1 (HSV-1), HSV-2, bovine herpesvirus 2, cercopithecine herpesvirus 1 (also known as herpes B virus), and ateline herpesvirus 1 (spider monkey herpesvirus). Examples of varicelloviruses includevaricella zoster virus, pseudorabies virus, simian varicella virus, bovine herpesvirus 1, bovine herpesvirus 5, caprine herpesvirus 1, porcine herpesvirus 1, equine herpesvirus 1, equine herpesvirus 3, equine herpesvirus 4, canine herpesvirus 1, feline herpesvirus 1, and duck herpesvirus 1. Examples of mardiviruses include Marek's disease virus (gallid herpesvirus 2), gallid herpesvirus 3, and herpesvirus of turkeys. An example of iltoviruses is gallid herpesvirus 1. Examples of cytomegaloviruses include human cytomegalovirus (HCMV, human herpesvirus 5 (HHV-5)), chimpanzee cytomegalovirus (CCMV, panine herpesvirus 2 (PaHV-2) and pongine herpesvirus-4 (PoHV-4)), simian cytomegalovirus (SCCMV, cercopithecine herpesvirus-5 (CeHV-5)), rhesus cytomegalovirus (RhCMV, cercopithecine herpesvirus 8 (CeHV-8)), herpesvirus aotus 1, and herpesvirus aotus 3. Examples of muromegaloviruses include murid herpesvirus 1, murid herpesvirus 2, and murid herpesvirus 3. Examples of proboscivirus include elephantid herpesvirus 1 (elephant endotheliotropic herpesvirus), caviid herpesvirus 2 (guinea pig cytomegalovirus), suid herpesvirus 2 (pig cytomegalovirus), and tupaiid herpesvirus 1 (tree shrew herpesvirus). Examples of roseoloviruses include human herpesvirus 6 and human herpesvirus 7. Another example of a virus belonging to the subfamily betaherpesvirinae is porcine herpesvirus 2. Examples of lymphocryptoviruses include human Epstein-Barr virus (EBV, Human herpesvirus 4, HHV-4), chimpanzee lymphocryptovirus (pongine herpesvirus 1, PoHV-1, herpesvirus pan), orangutan lymphocryptovirus (pongine herpesvirus 2, PoHV-2, orangutan herpesvirus), gorilla lymphocryptovirus (herpesvirus gorilla, pongine herpesvirus 3, PoHV-3), baboon lymphocryptovirus (baboon herpesvirus, herpesvirus papio, HVP, cercopithecine herpesvirus 12, CeHV-12), African green monkey EBV-like virus (cercopithecine herpesvirus 14, CeHV-14), rhesus lymphocryptovirus (rhesus LCV, RLV, cercopithecine HV 15), and marmoset lymphocryptovirus. Examples of rhadinoviruses include alcelaphine herpesvirus 1, alcelaphine herpesvirus 2, ateline herpesvirus 2, ateline herpesvirus 3, bovine herpesvirus 4 (Movar virus), equid herpesvirus 2 equid herpesvirus 5, equid herpesvirus 7 (asinine herpesvirus 2), hippotragine herpesvirus 1 (roan antelope herpesvirus), human herpesvirus 8 (HHV-8, Kaposi's sarcoma-associated herpesvirus), macacine herpesvirus 5 (rhesus rhadinovirus), murid herpesvirus 4 (mouse herpesvirus strain 68), ovine herpesvirus 2, saimiriine herpesvirus 2, and Japanese macaque rhadinovirus.

The family Papillomaviridae can be subdivided into the genera alphapapillomavirus, betapapillomavirus, gammapapillomavirus, deltapapillomavirus, epsilonpapillomavirus, etapapillomavirus, iotapapillomavirus, kappapapillomavirus, lamb dapapillomavirus, mupapillomavirus, nupapillomavirus, omikronpapillomavirus, pipapillomavirus, thetapapillomavirus, xipapillomavirus, and zetapapillomavirus. Human papillomaviruses can be subdivided into the genera alphapapillomavirus, betapapillomavirus, gammapapillomavirus, mupapillomavirus and nupapillomavirus. Examples of alphapapillomaviruses include human papillomvirus 2 (HPV-2, e.g., subtypes HPV-2, 27, 57), HPV-6 (e.g., subtypes HPV-6, 11, 13, 44, 74), bonobo papillomavirus 1 and 1-Chimpanzee (PCPV-1, PCPV-1C), human papillomavirus 7 (HPV-7, e.g., subtypes HPV-7, 40, 43, HPV-cand91), human papillomavirus 10 (HPV-10, e.g., subtypes HPV-3, 10, 28, 29, 77, 78, 94), human papillomavirus 16 (HPV-16, e.g., subtypes HPV-16, 31, 33, 35, 52, 58, 67), human papillomavirus 18 (HPV-18, e.g., subtypes HPV-18, 39, 45,59, 68, 70, HPV-cand85), human papillomavirus 26 (HPV-26, e.g., subtypes HPV-26, 51, 69, 82), human papillomavirus 32 (HPV-32, e.g., subtypes HPV-32 and 42), human papillomavirus 34 (HPV-34, e.g., subtypes HPV-34 and 73), human papillomavirus 53 (HPV-53, e.g., subtypes HPV-30, 53, 56, 66), human papillomavirus 54 (HPV-54), human papillomavirus 61 (HPV-61, e.g., subtypes HPV-61, 72, 81, 83, 84, cand62, cand86, cand87, cand89), human papillomavirus 71 (HPV-71), human papillomavirus cand90 (HPV-cand90), rhesus papillomavirus 1 (RhPV-1). Examples of betapapillomaviruses include human papillomavirus 5 (HPV-5, e.g., subtypes HPV-5, 8, 12, 14, 19, 20, 21, 24, 25, 36, 47), human papillomavirus 9 (HPV-9, e.g., subtypes HPV-9, 15, 17, 22, 23, 37, 38, 80), human papillomavirus 49 (HPV-49, e.g., subtypes HPV-49, 75, 76), human papillomavirus cand92 (HPV-cand92), and human papillomavirus cand96 (HPV-cand96). Examples of gamapapillomaviruses include human papillomavirus 4 (HPV-4, e.g., subtypes HPV-4, 65, 95), human papillomavirus 48 (HPV-48), human papillomavirus 50 (HPV-50), human papillomavirus 60 (HPV-60), and human papillomavirus 88 (HPV-88). Examples of xipapillomaviruses include bovine papillomavirus (BPV) 3, such as BPV-3, BPV-4, and BPV-6. Further examples of papillomaviruses include HPV-1, HPV-63, BPV-1, trichosurusvulpecula papillomavirus, possum papillomavirus, phocoenaspinipinnis papillomavirus, oral hamster papillomavirus, and cottontail rabbit papillomavirus.

The family Polyomaviridae can be subdivided into the genera orthopolyomavirus, wukipolyomavirus, and avipolyomavirus. Examples of orthopolyomaviruses include B-lymphotropic polyomavirus, baboon polyomavirus 1, bat polyomavirus, BK polyomavirus, Bornean orang-utan polyomavirus, bovine polyomavirus, California sea lion polyomavirus, dolphin polyomavirus 1, hamster polyomavirus, JC polyomavirus, Merkel Cell polyomavirus, murine pneumotropic virus, murine polyomavirus, Simian virus 40, squirrel monkey polyomavirus, Sumatran orang-utan polyomavirus, and Trichodysplasia spinuolsa-associated polyomavirus. Examples of wukipolyomaviruses include human polyomavirus 6, human polyomavirus 7, KI polyomavirus, and WU polyomavirus. Examples of avipolyomaviruses include avian polyomavirus, canary polyomavirus, crow polyomavirus, finch polyomavirus, and goose hemorrhagic polyomavirus. Further examples of the family polyomaviridae include African elephant polyomavirus 1, athymic rat polyomavirus, baboon polyomavirus 2, chimpanzee polyomavirus, cynomolgus polyomavirus, gorilla gorilla gorilla polyomavirus 1, human polyomavirus 9, human polyomavirus 10, mastomys polyomavirus, MW polyomavirus, MX polyomavirus, pan troglodytes verus polyomavirus 1a, pan troglodytes verus polyomavirus 2c, and rabbit kidney vacuolating virus.

The family Poxviridae can be subdivided into Chordopoxvirinae (including the genera avipoxvirus, capripoxvirus, cervidpoxvirus, crocodylipoxvirus, leporipoxvirus, molluscipoxvirus, orthopoxvirus, parapoxvirus, suipoxvirus, and yatapoxvirus) and Entomopoxvirinae (including the genera alphaentomopoxvirus, betaentomopoxvirus, and gammaentomopoxvirus). Examples of avipoxviruses include canarypox virus, fowlpox virus, juncopox virus, mynahpox virus, pigeonpox virus, psittacinepox virus, quailpox virus, sparrowpox virus, starlingpox virus, and turkeypox virus. Examples of capripoxviruses include sheeppox virus, goatpox virus, and lumpy skin disease virus. Examples of orthopoxviruses include buffalopox virus, camelpox virus, cowpox virus, ectromelia virus, monkeypox virus, raccoonpox virus, taterapox virus, vaccinia virus, variola virus, and volepox virus. Examples of parapoxviruses include bovine papular stomatitis virus, orf virus, parapoxvirus of red deer in New Zealand, pseudocowpox virus, squirrel parapoxvirus, auzduk disease virus, chamois contagious ecthyma virus, and Sealpox virus. Examples of yatapoxviruses include tanapox and yaba monkey tumor virus.

The family Hepadnaviridae can be subdivided into the genera orthohepadnavirus and avihepadnavirus. Examples of orthohepadnaviruses include bat hepatitis virus, ground squirrel hepatitis virus, hepatitis B virus, woodchuck hepatitis virus, and woolly monkey hepatitis B virus. Examples of avihepadnaviruses include duck hepatitis B virus, heron hepatitis B virus, ross Goose hepatitis B virus, snow goose hepatitis B virus, stork hepatitis B virus, and crane hepatitis B virus.

The family Parvoviridae can be subdivided into Densovirinae (including the genera brevidensovirus, densovirus, iteravirus, and pefudensovirus) and Parvovirinae (including the genera amdovirus, bocavirus, dependovirus, erythrovirus, parvovirus, and partetravirus). Examples of amdoviruses include aleutian mink disease virus and the gray fox amdovirus. Examples of bocaviruses include bovine bocavirus, canine minute virus, chimpanzee bocavirus, feline bocavirus, gorilla bocavirus 1, human bocavirus 1, human bocavirus 2, human bocavirus 3, human bocavirus 4, porcine bocavirus 1, porcine bocavirus 2, and porcine bocavirus 3. Examples of erythrovirus include human parvovirus B19, pig tailed macaque parvovirus, rhesus macaque parvovirus, and simian parvovirus. Examples of parvoviruses include bovine parvovirus, canine parvovirus, chicken parvovirus, feline panleukopenia virus, goose parvovirus, hamster parvovirus, HB virus, H-1 virus, human PARV 4, human PARV 5, Kilham rat virus, lapine parvovirus, LUIII virus, mink enteritis virus, minute virus of mice, murine parvovirus 1, porcine parvovirus, porcine hokovirus, raccoon parvovirus, rat minute virus 1a, rat minute virus 1b, rat minute virus 1c, RT parvovirus, and tumor virus X.

The family Astroviridae can be subdivided into the genera avastrovirus (e.g., avian nephritis virus, chicken astrovirus, duck astrovirus, and turkey astrovirus) and mamastrovirus (e.g., bovine astrovirus, capreolus capreolus astrovirus, feline astrovirus, human astrovirus, ovine astrovirus, mink astrovirus, and porcine astrovirus).

The family Caliciviridae can be subdivided into the genera lagovirus (e.g., European brown hare syndrome virus and rabbit haemorrhagic disease virus), nebovirus, norovirus (e.g., Norwalk virus), sapovirus, and vesivirus (e.g., canine calicivirus, feline calicivirus, San Miguel sealion virus, vesicular exanthema of swine virus, vesivirus Crol, and walrus calicivirus).

The family Picornaviridae can be subdivided into the genera aphthovirus (e.g., bovine rhinitis A virus, bovine rhinitis B virus, equine rhinitis A virus, and foot-and-mouth disease virus), aquamavirus, avihepatovirus, cardiovirus (e.g., encephalomyocarditis virus and theilovirus), cosavirus, dicipivirus, enterovirus (e.g., enterovirus A, enterovirus B, enterovirus C, enterovirus D, enterovirus E, enterovirus F, enterovirus G, enterovirus H, enterovirus J, rhinovirus A, rhinovirus B, and rhinovirus C), erbovirus (e.g., equine rhinitis B virus), hepatovirus (e.g., hepatitis A virus), kobuvirus (e.g., aichi virus, bovine kobuvirus, porcine kobuvirus and canine kobuvirus), megrivirus, parechovirus (e.g., human parechovirus 1, human parechovirus 2, and human parechoviruses 3, 4, 5 and 6), salivirus, sapelovirus, senecavirus, teschovirus (e.g., Porcine teschovirus), and tremovirus.

The family Coronaviridae can be subdivided into Coronavirinae (including the genera alphacoronavirus, betacoronavirus, deltacoronavirus, and gammacoronavirus (e.g., beluga whale coronavirus SW1)) and Torovirinae (including the genera bafinivirus (e.g., White Bream virus) and torovirus). Examples of alphacoronaviruses include alphacoronavirus 1, human coronavirus 229E, human coronavirus NL63, miniopterus bat coronavirus 1, miniopterus bat coronavirus HKU8, porcine epidemic diarrhea virus, rhinolophus bat coronavirus HKU2, and scotophilus bat coronavirus 512. Examples of betacoronaviruses include human coronavirus (CoV) 0C43, human coronavirus HKU1, MERS-CoV, SARS-CoV, pipistrellus bat coronavirus HKU5, tylonycteris bat coronavirus HKU4, and rousettus bat coronavirus HKU9. Examples of deltcoronaviruses include bulbul coronavirus HKU11, munia coronavirus HKU13, and thrush coronavirus HKU12. Examples of toroviruses include bovine torovirus, equine torovirus, human torovirus, and porcine torovirus.

The family Flaviviridae can be subdivided into the genera flavivirus, hepacivirus, pegivirus, and pestivirus. Examples of flaviviruses include Alkhurma virus, Deer tick virus, Gadgets Gully virus, Kadam virus, Karshi virus, Kyasanur Forest disease virus, Langat virus, Louping ill virus, Omsk hemorrhagic fever virus, Powassan virus, Royal Farm virus, Tick-borne encephalitis virus, Turkish sheep encephalitis virus, Meaban virus, Saumarez Reef virus, Tyuleniy virus, Aedes flavivirus, Barkedji virus, Calbertado virus, Cell fusing agent virus, Chaoyang virus, Culex flavivirus, Culex theileri flavivirus, Donggang virus, Kamiti River virus, Lammi virus, Nakiwogo virus, Nounane virus, Quang Binh virus, Aroa virus, Dengue virus, Kedougou virus, Bussuquara virus, Cacipacore virus, Koutango virus, Ilheus virus, Japanese encephalitis virus, Murray Valley encephalitis virus, Rocio virus, St. Louis encephalitis virus, Usutu virus, West Nile virus, Yaounde virus, Kokobera virus, Bagaza virus, Duck egg drop syndrome virus, Ilheus virus, Jiangsu virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, and Rio Bravo virus. Examples of hepaciviruses include canine hepacivirus, GBV-B, Guereza hepacivirus, hepatitis C virus, and rodent hepacivirus. Examples of pegiviruses include bat pegivirus, chimpanzee pegivirus, equine pegivirus, GB virus C, rodent pegivirus, and simian pegivirus. Examples of pestiviruses include antelope pestivirus, border disease virus, bovine viral diarrhoea virus 1, bovine viral diarrhoea virus 2, bungowannah pestivirus, classical swine fever virus, giraffe pestivirus, Hobi-like pestivirus, and Tunisian sheep virus.

The family Togaviridae can be subdivided into the genera alphavirus and rubivirus. Examples of alphaviruses include Aura virus, Babanki virus, Barmah Forest virus, Bebaru virus, Buggy Creek virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Mosso das Pedras virus, Mucambo virus, Ndumu virus, Ockelbo virus, O'nyong'nyong virus, Paramana virus, Pixuna virus, Rio Negro virus, Ross River virus, Salmon pancreas disease virus, Semliki Forest virus, Sindbis virus, Sleeping Disease virus, Southern elephant seal virus, Tonate virus, Trocara virus, Una virus, Venezuelan equine encephalitis virus, Western equine encephalitis virus, and Whataroa virus.

Examples of the family Hepeviridae include hepatitis E virus and rat hepatitis E virus.

The family Retroviridae can be subdivided into Orthoretrovirinae (including the genera alpharetrovirus, betaretrovirus, deltaretrovirus, epsilonretrovirus, gammaretrovirus, and lentivirus) and Spumaretrovirinae. Examples of alpharetroviruses include avian carcinoma Mill Hill virus 2, avian leukosis virus, avian myeloblastosis virus, avian myelocytomatosis virus 29, avian sarcoma virus CT10, Fujinami sarcoma virus, Rous sarcoma virus, UR2 sarcoma virus, and Y73 sarcoma virus. Examples of betaretroviruses include Jaagsiekte sheep retrovirus, Langur virus, Mason-Pfizer monkey virus, Mouse mammary tumor virus, and Squirrel monkey retrovirus. Examples of deltaretroviruses include bovine leukemia virus, primate T-lymphotropic virus 1, primate T-lymphotropic virus 2, and primate T-lymphotropic virus 3. Examples of epsilonretroviruses include Walleye dermal sarcoma virus, Walleye epidermal hyperplasia virus 1, and Walleye epidermal hyperplasia virus 2. Examples of gammaretroviruses include feline leukemia virus, gibbon ape leukemia virus, guinea pig type-C oncovirus, porcine type-C oncovirus, murine leukemia virus, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus, viper retrovirus, Chick syncytial virus, reticuloendotheliosis virus, and Trager duck spleen necrosis virus. Examples of lentiviruses include bovine immunodeficiency virus, Jembrana disease virus, equine infectious anemia virus, feline immunodeficiency virus, puma lentivirus, caprine arthritis encephalitis virus, Visna/maedi virus, human immunodeficiency virus (HIV) 1, HIV-2, and simian immunodeficiency virus. Examples of spumaviruses include African green monkey simian foamy virus, macaque simian foamy virus, bovine foamy virus, equine foamy virus, and feline foamy virus.

The family Orthomyxoviridae can be subdivided into the genera influenzavirus A, influenzavirus B, influenzavirus C, isavirus (e.g., infectious salmon anemia virus), quaranjavirus, and thogotovirus (e.g., thogoto virus and Dhori virus). Subtypes of influenzavirus A include H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7. Further examples of the family orthomyxoviridae include Quaranfil virus, Johnston Atoll virus, and Lake Chad virus.

Examples of the family Arenaviridae include Gbagroube virus, Ippy virus, Kodoko virus, Lassa virus, Lujo virus, Luna virus, Lunk virus, Lymphocytic choriomeningitis virus, Merino Walk virus, Menekre virus, Mobala virus, Mopeia virus, Amapari virus, Chapare virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, and Whitewater Arroyo virus.

The family Bunyaviridae can be subdivided into the genera hantavirus, nairovirus, orthobunyavirus, and phlebovirus. Examples of hantaviruses include Andes virus, Amur virus, Asama virus, Azagny virus, Bayou virus, Black Creek Canal virus, Bloodland Lake virus, Blue River virus, Cano Delgadito virus, Calabazo virus, Carrizal virus, Catacamas virus, Choclo virus, Dobrava-Belgrade virus, El Moro Canyon virus, Gou virus, Hantaan River virus, Huitzilac virus, Imjin virus, Isla Vista virus, Khabarovsk virus, Laguna Negra virus, Limestone Canyon virus, Magboi virus, Maripa virus, Monongahela virus, Montano virus, Mouyassue virus, Muleshoe virus, Muju virus, New York virus, Nova virus, Oran virus, Oxbow virus, Playa de Oro virus, Prospect Hill virus, Puumala virus, Rockport virus, Rio Mamore virus, Rio Segundo virus, Sangassou virus, Saaremaa virus, Seoul virus, Serang virus, Sin Nombre virus, Soochong virus, Tanganya virus, Thailand virus, Thottapalayam virus, Topografov virus, Tula virus, and Xuan Son virus. Examples of nairoviruses include Abu Hammad virus, Abu Mina virus, Bandia virus, Crimean-Congo hemorrhagic fever virus, Dera Ghazi Khan virus, Dugbe virus, Erve virus, Farallon virus, Ganjam virus, Hazara virus, Hughes virus, Kupe virus, Nairobi sheep disease virus, Punte Salinas virus, Qalyub virus, Raza virus, Sakhalin virus, Thiafora virus, and Tillamok virus. Examples of orthobunyaviruses include Acara virus, Akabane virus, Alajuela virus, Anopheles A virus, Anopheles B virus, Bakau virus, Batama virus, Benevides virus, Bertioga virus, Bimiti virus, Botambi virus, Bunyamwera virus, Bushbush virus, Bwamba virus, California encephalitis virus, Capim virus, Caraparu virus, Catu virus, Estero Real virus, Gamboa virus, Guajara virus, Guama virus, Guaroa virus, Jatobal virus, Kaeng Khoi virus, Kairi virus, Koongol virus, Kowanyama virus, La Crosse virus, M'Poko virus, Madrid virus, Main Drain virus, Manzanilla virus, Marituba virus, Minatitlan virus, Nyando virus, Olifantsvlei virus, Oriboca virus, Oropouche virus, Patois virus, Sathuperi virus, Schmallenberg virus, Shamonda virus, Shuni virus, Simbu virus, South River virus, Tacaiuma virus, Tahyna virus, Tete virus, Thimiri virus, Timboteua virus, Turlock virus, Wyeomyia virus, and Zegla virus. Examples of phleboviruses include Adria virus, Alenquer virus, Ambe virus, Arbia virus, Arboledas virus, Armero virus, Arumowot virus, Belterra virus, Bhanja virus, Bujaru virus, Chandiru virus, Chagres virus, Changuinola virus, Chilibre virus, Durania virus, Essaouira virus, Forecariah virus, Frijoles virus, Gabek Forest virus, Gordil virus, Granada virus, Heartland virus, Henan Fever virus, Ixcanal virus, Kala Iris virus, Kismayo virus, Joa virus, Karimabad virus, Lone Star virus, Mariquita virus, Massilia virus, Odrenisrou virus, Pacui virus, Palma virus, Punta Toro virus, Rift Valley fever virus, Rio Grande virus, Salehebad virus, Salobo virus, Soldado virus, Saint Floris virus, Sandfly fever Naples virus, Sandfly fever Sicilian virus, SFTS virus, Toscana virus, Tunis virus, and Uukuniemi virus.

The family Filoviridae can be subdivided into the genera cuevavirus (e.g., Lloviu cuevavirus), ebolavirus (e.g., Bundibugyo ebolavirus, Reston ebolavirus, Sudan ebolavirus, TO Forest ebolavirus, and Zaire ebolavirus), and Marburgvirus.

The family Paramyxoviridae can be subdivided into Paramyxovirinae (including the genera aquaparamyxovirus, avulavirus, ferlavirus, henipavirus, morbillivirus, respirovirus, rubulavirus, and TPMV-like viruses) and Pneumovirinae (including the genera metapneumovirus (e.g., human metapneumovirus) and pneumovirus). Examples of the genera avulavirus include avian paramyxovirus (e.g., avian paramyxovirus 2, 3, 4, 5, 6, 7, 8, 9, 11, 12), goose paramyxovirus, and Newcastle disease virus. Examples of henipaviruses include Cedar virus, Hendra virus, and Nipah virus. Examples of morbiliviruses include canine distemper virus, cetacean morbillivirus, feline morbillivirus, measles virus, peste-des-petits-ruminants virus, phocine distemper virus, and rinderpest virus. Examples of rubulaviruses include Achimota virus 1, Achimota virus 2, Mapuera virus, Menangle virus, mumps virus, parainfluenza type 2, parainfluenza type 4, parainfluenza type 5, porcine rubulavirus, simian virus 41, Tioman virus, Tuhokovirus virus 1, Tuhokovirus virus 2, and Tuhokovirus virus 3.

The family Rhabdoviridae can be subdivided into the genera ephemerovirus (e.g., Bovine ephemeral fever virus), lyssavirus, novirhabdovirus, perhabdovirus (e.g., perch rhabdovirus), sigmavirus (e.g., Drosophila melanogaster sigmavirus), tibrovirus (e.g., Tibrogargan virus), and vesiculovirus. Examples of lyssaviruses include Aravan virus, Australian bat lyssavirus, Bokeloh bat lyssavirus, Duvenhage virus, European bat lyssavirus 1, European blyssavirus 2, Irkut virus, Khujand virus, Lagos bat virus, Mokola virus, rabies virus, West Caucasian bat virus, and Shimoni bat virus. Examples of novirhabdoviruse include Hirame rhabdovirus, infectious hematopoietic necrosis virus, viral hemorrhagic septicemia virus, and snakehead rhabdovirus. Examples of vesiculoviruses include Carajas virus, Chandipura virus, Cocal virus, Isfahan virus, Malpais Spring virus, Maraba virus, Piry virus, spring viraemia of carp virus, vesicular stomatitis Alagoas virus, and vesicular stomatitis New Jersey virus. Examples of orthoreoviruses include avian orthoreovirus, baboon orthoreovirus, Kampar virus, mammalian orthoreovirus, Melaka virus, Nelson Bay virus, Pulau virus, reptilian orthoreovirus, Steller sea lion reovirus, Tvarminne avian virus, and Xi River virus. A further example of the family spinareovirinae is piscine reovirus.

The family Reoviridae can be subdivided into Sedoreovirinae (including the genera cardoreovirus, mimoreovirus, orbivirus, rotavirus (e.g., rotavirus A, B, C, D, and E), and seadornavirus (e.g., Banna virus)) and Spinareovirinae (including the genera aquareovirus, coltivirus (e.g., Colorado tick fever virus), cypovirus, dinovernavirus, idnoreovirus, mycoreovirus, orthoreovirus, andcrabreovirus). Examples of orbiviruses include African horse sickness virus, Bluetongue virus, Changuinola virus, Chenuda virus, Chobar Gorge virus, Corriparta virus, Epizootic hemorrhagic disease virus, Equine encephalosis virus, Eubenangee virus, Great Island virus, Ieri virus, Lebombo virus, Orungo virus, Palyam virus, Peruvian horse sickness virus, Sathuvachari virus, St Croix River virus, Umatilla virus, Wad Medani virus, Wallal virus, Warrego virus, Wongorr virus, and Yunnan orbivirus.

A further example of an animal pathogenic virus is hepatitis delta virus.

Preferred animal pathogenic viruses belong to a family selected from the group consisting of Herpesviridae, Papillomaviridae, Polyomaviridae, Hepadnaviridae, Flaviviridae and Retroviridae. For example, the animal pathogenic virus may be selected from the group consisting of HIV, HBV and herpes virus.

A "human pathogenic virus" is an animal pathogenic virus as specified above which can infect a human and which causes or mediates a condition, disorder or disease in said human.

The term "virus which uses cellular mechanisms in the animal host for its replication and/or transcription" means that the virus at least partially depends on the DNA and RNA synthesizing machinery and/or RNA processing machinery of the virus' host for the virus' replication. In one embodiment, the virus uses at least one (e.g., 1, 2, or 3) of its own viral enzymes for its replication and/or transcription. In this respect, the virus' enzymes may be selected from the group consisting of viral proteases, viral polymerases, viral kinases, and viral integrases. Examples of the viral polymerases include RNA polymerases, DNA polymerases (such as RNA-dependent RNA polymerases (e.g., an RNA replicase), DNA-dependent RNA polymerases, RNA-dependent DNA polymerases) and reverse transcriptases (which have activities of RNA-dependent DNA polymerases and DNA-dependent DNA polymerases).

The term "reverse transcribing virus" means a virus the replication of which involves reverse transcription. In this respect, the term "reverse transcription" refers to the process of generating complementary DNA from an RNA template. The reverse transcribing virus may have an RNA genome (i.e., Baltimore classification group VI; e.g., the virus is a member of the family Retroviridae) or a DNA genome (i.e., Baltimore classification group VII, e.g., the virus is a member of the family Hepadnaviridae).

A DNA virus refers to a virus which has DNA as its genetic material and replicates using a DNA-dependent DNA polymerase. A DNA virus may be double-stranded (dsDNA; Baltimore classification group I) or single-stranded (ssDNA, Baltimore classification group II). An RNA virus refers to a virus which has RNA as its genetic material and replicates using an RNA-dependent RNA polymerase. An RNA virus may be double-stranded (dsRNA; Baltimore classification group III) or single-stranded which can be further classified into positive sense viruses ((+)ssRNA, Baltimore classification group IV) or negative sense viruses ((-)ssRNA, Baltimore classification group V).

The terms "disease", "disorder" and "condition", when used in the context of treatment or therapy (including prophylactic therapy), are used herein interchangeably and refer to any pathological state, including cancer, in particular those pathological states (including cancer forms) described herein.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease.

The term "cancer" comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Any reference herein to cancer or particular forms of cancer also includes cancer metastasis thereof. By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" relates to lymph node metastasis.

As used herein, the term "small molecules" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds), and salts, esters, and other pharmaceutically acceptable forms of any of the foregoing, wherein the organic and inorganic compounds have a molecular weight less than about 10,000 grams per mole, such as less than about 5,000 grams per mole, less than about 1,000 grams per mole, less than about 500 grams per mole, or less than about 100 grams per mole.

The term "a condition, disorder or disease that is mediated or caused by a virus" means any pathological state which is elicited indirectly and/or directly by the virus. I.e., a disease caused by a virus refers to a disease which is directly elicited by the virus (i.e., a primary infection). In this respect, the term "primary infection" means that the disease is caused as a result of the virus' presence or activity within the normal, healthy subject, and the virus' intrinsic virulence is at least partially a necessary consequence of the virus' need to reproduce and spread. An example of a primary infection is hepatitis B caused by HBV. According to the present invention, a disease mediated by a virus refers to a disease which is indirectly elicited by the virus (i.e., an opportunistic infection). In this respect, the term "opportunistic infection" means that the disease results from an otherwise innocuous pathogen and requires that the subject's defenses are impaired by the virus (e.g., since the virus has immunosuppressive activity). An example of an opportunistic infection is AIDS-related Karposi sarcoma.

The term "virus strain" means a genetic variant or subtype of a virus having a common mutation profile distinguishing the strain from the wild type virus. The common mutation profile may alter one or more of the virus' properties (such as virulence, latency, antiviral drug resistance, immunosuppression, etc.). In this respect, the term "alter" includes not only the situation that one or more of the virus' properties are increased or decreased but also the situation that the mutation profile imparts a new property (such as virulence to a new subject, latency, antiviral drug resistance, immunosuppression, etc.) to the virus strain compared to the wild-type virus which does not have said new property.

The term "virulence" of a virus (in particular, a virus strain) means the degree of pathogenicity of the virus as indicated by case fatality rates and/or the ability of the virus to invade the tissues of the host (i.e., the virus' infectivity). The pathogenicity of a virus (in particular, a virus strain) means its ability to cause or mediate a disease (i.e., disease severity). The expression "ability to cause or mediate a disease" is to be understood in the same manner as in the term "a condition, disorder or disease that is mediated or caused by a virus" described above. I.e., the virus' ability to cause a disease is the virus' ability to directly elicit a disease (i.e., a primary infection), whereas the virus' ability to mediate a disease is the virus' ability to indirectly elicit a disease (i.e., an opportunistic infection). The virus' pathogenicity can be determined by its virulence factors which comprise the colonization of a niche in the host (including attachment to cells), immunoevasion (i.e., the virus' ability to evade the host's immune response), immunosuppression (i.e., the ability to inhibit the host's immune response), entry into and exit out of cells, and the ability to obtain nutrition from the host.

The term "persistent infection" means a viral infection in which the virus is not cleared from the subject but remains in cells of the subject either for a long time (e.g., weeks (e.g., 1, 2, 3, 4, 5, 6, 7, or, 8 weeks), to months (e.g., 1, 2, 3, 4, 5, 6, 7, 8, 9, 10, 11, or 12 months) or years (e.g., 1, 2, 3, 4, 5, 6, 7, 8, 9, or 10 years or more) or life-long. Persistent infections can be classified into three types, i.e., latent, chronic and slow infections. Cells of a subject which are infected by a persistent infection may be cells which do not produce viruses (in particular detectable infectious virus or viral progeny) and/or cells which produce viruses (in particular detectable infectious virus or viral progeny). For example, cells of a subject which are infected by a persistent infection may produce viruses (in particular detectable infectious virus or viral progeny) during one or more periods of time (i.e., during productive periods), whereas during other periods of time they do not produce viruses (in particular detectable infectious virus or viral progeny). The productive periods may comprise recurring episodes of disease (which normally do not lead to (i) the killing of the subject or (ii) excessive (e.g., irreparable or fatal) damage of the cells of the subject; cf. infections caused by herpesviruses) or onset of severe disease (cf., e.g., infections caused by lentiviruses). During persistent infections, the viral genome may be either stably integrated into the cellular DNA of the subject or maintained in another way (e.g., episomally such as in the form of covalently closed circular DNA (cccDNA)). A virus may maintain more than one type of persistent infection at the same time, but in different cells of the same subject, wherein the type of persistent infection may or may not depend on the cell type and the physiologic state of the cell. Thus, in one subject, infection with a single virus may involve multiple types of persistence (e.g., a latent infection and a chronic infection), each of which may become more or less important depending on the subject's response to the disease.

The term "latent infection", as used herein, means a persistent infection lacking detectable virus (in particular detectable infectious virus or viral progeny) between episodes of recurrent disease. The term "viral latency" means the ability of a virus to lie dormant (latent) within a cell of a subject. Latency can be denoted as the phase in the life cycle of a virus in which, after initial infection, the generation of viruses (in particular, infectious viruses or viral progeny) ceases, although the virus' genome is not cleared (i.e., fully eradicated) from the subject. Consequently, the virus can reactivate (or can be reactivated by a stimulus including changes in cell physiology, superinfection by another virus, physical stress or trauma, and/or immunosuppression of the subject) and begin producing viruses (in particular, infectious viruses or viral progeny) without the subject being infected by new outside virus and stays within the subject indefinitely.

The term "chronic infection", as used herein, means a persistent infection in which, after initial infection, the virus (in particular detectable infectious virus or viral progeny) is present in the subject for a long time (e.g., weeks (e.g., 1, 2, 3,4, 5, 6, 7, or, 8 weeks), to months (e.g., 1, 2, 3, 4, 5, 6, 7, 8, 9, 10, 11, or 12 months) or years (e.g., 1, 2, 3, 4, 5, 6, 7, 8, 9, or 10 years or more) or life-long and results in chronic or recurrent disease. A chronic infection may be eventually cleared.

The term "slow infection", as used herein, means a persistent infection having a prolonged incubation period followed by progressive disease. In contrast to latent and chronic infections, slow infection do not start with an acute period of viral multiplication.

The term "acute" infection, as used herein, means an infection having a short duration (i.e., in the order of several days, such as 1 to 10 days, e.g., 1, 2, 3, 4, 5, 6, 7, 8, 9, or 10 days). Usually, an acute infection is characterized by a fast onset of disease (i.e., early production of viruses (in particular, infectious viruses or viral progeny)), a relatively short period (e.g., in the order of several days, such as 1 to 10 days, e.g., 1, 2, 3, 4, 5, 6, 7, 8, 9, or 10 days) of symptoms, and resolution within days (such as 1 to 10 days, e.g., 1, 2, 3, 4, 5, 6, 7, 8, 9, or 10 days) normally, due to the action of the immune system of the subject).

The term "antiviral drug", as used herein, means a drug used specifically for treating viral infections. An antiviral drug does not destroy its target virus (such as an animal pathogenic virus as disclosed herein) but inhibits its development, e.g., by inhibiting one or more stages of the life cycle of the virus, e.g., one or more of attachment of the virus to a cell of the subject, release of viral genes and optionally enzymes into the cell, replication of viral components, assembly of viral components into complete viral particles, and release of viral particles to infect new host cells. Thus, examples of antiviral drugs include entry inhibitors, reverse transcriptase (RT) inhibitors, integrase inhibitors, replication enzyme inhibitors, protease inhibitors, inhibitors of viral kinases, uncoating inhibitors, assembly inhibitors, and release inhibitors.

The term "inhibitor" as used herein above refers to any compound capable of reducing one or more of biological activities of a target, e.g., a target protein such as a target enzyme. Biological activities as used herein include the enzymatic activity of the target, its catalytic activity and any other capability of the target in order to serve its purpose (e.g., to produce infectious virus particles). With respect to viruses (such as an animal pathogenic virus as disclosed herein), the target may be any protein or enzyme which is needed to produce virus progeny, in particular infectious virus progeny, such as infectious virus particles. In one embodiment, the target protein or enzyme is viral. In another embodiment, the target protein or enzyme is from the host which the virus infects. The protein or enzyme which is needed to produce virus progeny may be a structural protein (e.g., a capsid protein, membrane protein, or nucleoprotein), a uncoating protein (e.g., an enzyme which degrades the viral capsid or envelope after entry of the virus into the host cell), an integrase, a reverse transcriptase, or a replication enzyme (e.g., an RNA or DNA polymerase, such as an RNA-dependent RNA polymerase (such as an RNA replicase), a DNA-dependent RNA polymerase, or an RNA-dependent DNA polymerase). Generally, the inhibitor may be for example a small molecule or a peptide, polypeptide (including antibodies) or peptidomimetic.

Reducing the biological activity preferably means a reduction by up to or by at least 10%, by up to or by at least 20%, by up to or by at least 30%, by up to or by at least 40%, by up to or by at least 50%, by up to or by at least 60%, by up to or by at least 70%, by up to or by at least 80%, by up to or by at least 90% or by up to 100%. The term includes any kind of inhibitor such as a reversible or irreversible inhibitor. For determining the biological activity, the following assay conditions as published in Rosenbaum et al. 2010 (*J. Med. Chem.* 2010, 53: 5281-5289) can be used.

An entry inhibitor may be a compound, preferably a small molecule or a peptide, peptide analog or peptidomimetic, interfering with or preventing (i) the binding of a virus to its host cell, (ii) fusion of a virus with its host cell and/or (iii) entry of a virus into its host cell. Particular examples of entry inhibitors include a CCR5 inhibitor (such as maraviroc or an antibody binding to CCR5), a compound binding to gp41 (such as enfuvirtide (also called T-20) or an antibody binding to gp41), a compound binding to CD4, a compound binding to CXCR4, and a compound binding to gp120.

A reverse transcriptase (RT) inhibitor may be a compound, preferably a small molecule or a peptide, peptide analog or peptidomimetic, interfering with or preventing the reverse transcription of viral RNA into DNA. In one embodiment, the incorporation of an RT inhibitor into the DNA chain can result in the termination of the DNA chain. In another embodiment, the RT inhibitor reduces (or blocks) the enzymatic activity of RT by binding directly to RT. RT inhibitors can be nucleoside analogs, nucleotide analogs, or non-nucleoside compounds. Particular examples of nucleoside analogs RT inhibitors include zidovudine (also called azidothymidine), didanosine, zalcitabine (also called dideoxycytidine), stavudine, lamivudine, abacavir, emtricitabine, and entecavir. Particular examples of nucleotide analogs RT inhibitors include tenofovir (such as tenofovir disoproxil fumarate) and adefovir. Particular examples of non-nucleoside RT inhibitors include efavirenz, nevirapine, delavirdine, etravirine, and rilpivirine.

A replication enzyme inhibitor may be a compound, preferably a small molecule or a peptide, peptide analog or peptidomimetic, interfering with or preventing the replication (in particular the synthesis) of viral nucleic acids, e.g., by the incorporation of a replication enzyme inhibitor into the nucleic acid (such as DNA or RNA) chain resulting in the termination of the nucleic acid chain. Examples of replication enzyme inhibitors include nucleoside analogs and nucleotide analogs, such as those described above, and pyrophosphate anlogs (such as foscarnet). Particular examples of replication enzyme inhibitors are zidovudine, didanosine, zalcitabine, stavudine, lamivudine, abacavir, emtricitabine, entecavir, tenofovir (such as tenofovir disoproxil fumarate), adefovir, ganciclovir, acyclovir, famciclovir, and valacyclovir.

An integrase inhibitor may be a compound, preferably a small molecule or a peptide, peptide analog or peptidomimetic, interfering with or preventing the insertion of viral genome into the genome of the host cell. Particular examples of integrase inhibitors include raltegravir, elvitegravir and dolutegravir.

A protease inhibitor may be a compound, preferably a small molecule or a peptide, peptide analog or peptidomimetic, interfering with or preventing/blocking proteolytic cleavage of viral protein precursors that are necessary for the production of infectious viral particles. Particular examples of protease inhibitors include saquinavir, ritonavir, indinavir, nelfinavir, amprenavir, boceprevir, telaprevir, lopinavir, atazanavir, fosamprenavir, tipranavir, and darunavir.

An uncoating inhibitor may be a compound, preferably a small molecule or a peptide, peptide analog or peptidomimetic, interfering with or preventing the uncoating/dismanteling of a virus upon or after entry of the virus into the host cell. Particular examples of uncoating inhibitors include amantadine and rimantidine.

An assembly inhibitor may be a compound, preferably a small molecule or a peptide, peptide analog or peptidomimetic, interfering with or preventing the assembly of infectious virus particles (e.g., the assembly of viral capsid proteins). A particular example of assembly inhibitors includes rifampicin.

A release inhibitor may be a compound, preferably a small molecule or a peptide, peptide analog or peptidomimetic, interfering with or preventing the release of infectious virus particles from the host cell, e.g., by interfering with or preventing budding of the virus particles. Particular examples of release inhibitor include zanamivir and oseltamivir.

The term "immunosuppression", as used herein, means the reduced activation and/or efficacy of the immune system. Immunosuppression can be deliberately induced (e.g., in order to prevent the subject's body from rejecting an organ transplant, treating graft-versus-host disease, and/or for the treatment of auto-immune diseases), for example, by drugs, surgery (e.g., splenectomy), plasmapharesis, or radiation. Immunosuppression can also be induced non-deliberately (e.g., by malnutrition, aging, many types of cancer (such as leukemia, lymphoma, multiple myeloma), and certain chronic infections such as HIV) leading to increased susceptibility to pathogens such as virus (e.g., an animal pathogenic virus as disclosed herein). An immunocompromised subject is an individual who is undergoing immunosuppression, or whose immune system is weak for other reasons (e.g., because of chemotherapy, HIV, or Lupus).

The term "virus strain which is resistant to one or more antiviral drugs", as used herein, means that the one or more antiviral drugs exhibit a reduced effectiveness against said virus strain (in particular a virus strain of an animal pathogenic virus as disclosed herein) compared to the effectiveness of the same one or more antiviral drugs against the wild type virus (preferably, all experimental conditions other than the type of virus used (i.e., resistant virus strain vs. wild-type virus) used to determine the effectiveness are identical or comparable). When the virus strain is resistant against more than one antiviral drug (e.g., against 2, 3, or 4 antiviral drugs), it exhibits multidrug resistance (MDR) or is multidrug-resistant. The effectiveness may be measured with respect to (i) the amount of virus progeny (e.g., infectious virus progeny, in particular infectious virus particles) released from the infected host cell; (ii) the amount of total viral nucleic acid and/or protein in the infected host cell; (iii) the amount of specific viral nucleic acid (e.g., ccc DNA) and/or protein in the infected host cell; (iv) the amount of antiviral drug required to achieve a certain result (such as the induction of a response halfway between the baseline and maximum after a specified exposure time ($EC_{50}$ value)); and/or (v) the survival time of the infected host cell. In one embodiment, the effectiveness of the one or more antiviral drugs against said virus strain is reduced to at most 90% (such at most 80%, at most 70%, at most 60%, at most 50%, at most 45%, at most 40%, at most 35%, at most 30%, at most 25%, at most 20%, at most 15%, at most 10%, at most 9%, at most 8%, at most 7%, at most 6%, at most 5%, at most 4%, at most 3%, at most 2%, at most 1%, at most 0.9%, at most 0.8%, at most 0.7%, at most 0.6%, at most 0.5%, at most 0.4%, at most 0.3%, at most 0.2%, at most 0.1%, at most 0.05%, at most 0.01%, at most 0.009%, at most 0.008%, at most 0.007%) with respect to the effectiveness of the same one or more antiviral drugs against the wild type virus. For example, if the effectiveness is determined on the basis of the survival time of the infected host cell, the survival time of the host cell which is infected with the resistant virus strain and which has been treated with the one or more antiviral drugs may be at most 90% (such at most 80%, at most 70%, at most 60%, at most 50%, at most 45%, at most 40%, at most 35%, at most 30%, at most 25%, at most 20%, at most 15%, at most 10%, at most 9%, at most 8%, at most 7%, at most 6%, at most 5%, at most 4%, at most 3%, at most 2%, at most 1%, at most 0.9%, at most 0.8%, at most 0.7%, at most 0.6%, at most 0.5%, at most 0.4%, at most 0.3%, at most 0.2%, at most 0.1%, at most 0.05%, at most 0.01%, at most 0.009%, at most 0.008%, at most 0.007%) with respect to the survival time of a host cell which is infected with the wild type virus and which has been treated with the one or more antiviral drugs (preferably, all experimental conditions other than the type of virus (i.e., resistant virus strain vs. wild-type virus) used to determine the amount of virus progeny are identical or comparable). If the effectiveness is determined on the basis of the amount of virus progeny (e.g., infectious virus progeny, in particular infectious virus particles) released from the infected host cell, the amount of virus progeny released from the host cell which is infected with the resistant virus strain and which has been treated with the one or more antiviral drugs may be at least 110% (such as at least 125%, at least 140%, at least 165%, at least 200%, at least 220%, at least 250%, at least 285%, at least 330%, at least 400%, at least 500%, at least 670%, at least 1000%, at least 1110%, at least 1250%, at least 1430%, at least 1665%, at least 2000%, at least 2500%, at least 3330%, at least 5000%, at least 10 000%, at least 11 100%, at least 12 500%, at least 14 285%, at least 16 665%, at least 20 000%, at least 25 000%, at least 33 000%, at least 50 000%, at least 100 000%, at least 200 000%, at least 1 000 000%, at least 1 111 000%, at least 1 250 000%, at least 1 300 000%) with respect to the amount of virus progeny (e.g., infectious virus progeny, in particular infectious virus particles) released from a host cell which is infected with the wild type virus and which has been treated with the one or more antiviral drugs (preferably, all experimental conditions other than the type of virus (i.e., resistant virus strain vs. wild-type virus) used to determine the amount of antiviral drug required to achieve the result are identical or comparable). The same applies if the effectiveness is determined on the basis of (ii) the amount of total viral nucleic acid and/or protein in the infected host cell; (iii) the amount of specific viral nucleic acid (e.g., ccc DNA) and/or protein in the infected host cell; or (iv) the amount of antiviral drug required to achieve a certain result (such as the induction of a response halfway between the baseline and maximum after a specified exposure time ($EC_{50}$ value)) (i.e., the amount of total viral nucleic acid and/or protein in the host cell which is infected with the resistant virus strain and which has been treated with the one or more antiviral drugs may be at least 110% (such as at least 125%, . . . at least 100 000%, at least 200 000%, at least 1 000 000%, at least 1 111 000%, at least 1 250 000%, at least 1 300 000%) with respect to the amount of total viral nucleic acid and/or protein in the host cell which is infected with the wild-type virus and which has been treated with the one or more antiviral drugs.

Examples of multidrug-resistant viruses include strains of HIV, influenza virus (resistant to amantadine, optionally also to neuraminidase inhibitors such as oseltamivir), cytomegalovirus (resistant to ganciclovir and foscarnet), and Herpes simplex virus (rarely resistant to acyclovir, mostly in the form of cross-resistance to famciclovir and valacyclovir).

The term "host" as used in the context of a virus means a subject (e.g., a species thereof) or a cell of the subject which can be infected by the virus and/or in which the virus replicates. Preferably, a virus' host is a subject (e.g., a species thereof) in which a condition, disorder or disease is mediated or caused by the virus.

The terms "patient", "subject", "individual", or "animal" relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, sheep, cattle, goats, pigs, horses etc., laboratory mammals such as rodents, e.g., mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc.; particular non-limiting examples of bony or cartilaginous fish include those suitable for cultivation by aquiculture, and include bony fish such as salmon, trout, perch, carp, cat-fish, etc.

Compounds

The compounds used in the present invention are selected from the group consisting of a pyrone derivative having the general formula (I) or (II)

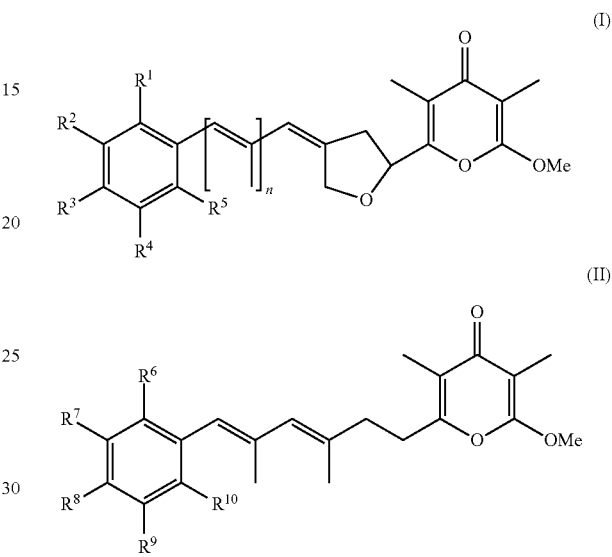

and hydrates, solvates, salts, complexes, racemic mixtures, diastereomers, enantiomers, and tautomers thereof and isotopically enriched forms of any of the foregoing, wherein $R^1$, $R^2$, $R^3$, $R^4$, and $R^5$ are independently selected from the group consisting of hydrogen, halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})$ $(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, cycloalkyl, heterocyclyl, aryl, and heteroaryl groups is substituted with from 0 to 3 substituents independently selected from the group consisting of $R^{30}$, phosphoryl, folic acid, and molecular probes; or either $R^1$ and $R^2$, or $R^2$ and $R^3$, or $R^3$ and $R^4$, or $R^4$ and $R^5$ may join together with the atoms to which they are attached to form a 5-to 8-membered ring that is substituted with from 0 to 3 substituents independently selected from the group consisting of $R^{30}$, phosphoryl, folic acid, and molecular probes;

$R^6$, $R^7$, $R^8$, $R^9$, and $R^{10}$ are independently selected from the group consisting of hydrogen, halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{12}R^{11}$, —$NR^{11}S(O)_{1-2}OR^{11}$, —$NR^{11}S(O)_{1-2}N(R^{12})$ $(R^{13})$, —$C(=X)R^{11}$, —$C(=X)$ $XR^{11}$, —$XC(=X)R^{11}$, and —$XC(=X)XR^{11}$, wherein each of the alkyl, alkenyl, alkynyl, cycloalkyl, heterocyclyl, aryl, and heteroaryl groups is substituted with from 0 to 3 substituents independently selected from the group consisting of $R^{30}$, phosphoryl, folic acid, and molecular probes; or either $R^6$ and $R^7$, or $R^7$ and $R^8$, or $R^8$ and $R^9$, or $R^9$ and $R^{10}$ may join together with the atoms to which they are attached to form a 5-to 8-membered ring that is substituted with from 0 to 3 substituents independently selected from the group consisting of $R^{30}$, phosphoryl, folic acid, and molecular probes;

n is 1, 2, or 3,

X is independently selected from O, S, and $N(R^{14})$;

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —$N=CR^{15}R^{16}$, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —$NH_yR^{20}{}_{2-y}$, or $R^{15}$ and $R^{16}$ may join together with the atom to which they are attached to form a ring which is optionally substituted with one or more independently selected $R^{30}$, wherein each of the alkyl, alkenyl, alkynyl, cycloalkyl, aryl, heteroaryl, and heterocyclyl groups is optionally substituted with one or more independently selected $R^{30}$; y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, —NC, —NCO, —CNO, —SCN, —NCS, —$N_3$, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}$, —$S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3-to 14-membered aryl, 3-to 14-membered heteroaryl, 3-to 14-membered cycloalkyl, 3-to 14-membered heterocyclyl, halogen, —$CF_3$, —CN, —NC, —NCO, —CNO, —SCN, —NCS, —$N_3$, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}$, —$S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3-to 14-membered aryl, 3-to 14-membered heteroaryl, 3-to 14-membered cycloalkyl, 3-to 14-membered heterocyclyl groups being a $2^{nd}$ level substituent is optionally substituted with one or more $3^{rd}$ level substituents, wherein said $3^{rd}$ level substituent is, in each case, independently selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=O)NH_{2-z}(C_{1-3}$ alkyl)$_z$, —$NHC(=NH)NH_{2-z}(C_{1-3}$ alkyl)$_z$, —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3-to 14-membered cycloalkyl or heterocyclyl group being a $2^{nd}$ level substituent may join together to form =O, =S, =NH, or =$N(C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3-to 7-membered cycloalkyl, 5- or 6-membered aryl, 5- or 6-membered heteroaryl, and 3-to 7-membered heterocyclyl, wherein each of the $C_{1-6}$ alkyl, $C_{2-6}$ alkenyl, $C_{2-6}$ alkynyl, 3-to 7-membered cycloalkyl, 5- or 6-membered aryl, 5- or 6-membered heteroaryl, and 3-to 7-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —$OC(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl; $R^{81}$, $R^{82}$, and $R^{83}$ are independently selected from the group consisting of —H, $C_{1-4}$ alkyl, $C_{2-4}$ alkenyl, $C_{2-4}$ alkynyl, 3-to 6-membered cycloalkyl, 5- or 6-membered aryl, 5- or 6-membered heteroaryl, and 3-to 6-membered heterocyclyl, wherein each of the $C_{1-4}$ alkyl, $C_{2-4}$ alkenyl, $C_{2-4}$ alkynyl, 3-to 6-membered cycloalkyl, 5- or 6-membered aryl, 5- or 6-membered heteroaryl, and 3-to 6-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}(C_{1-3}$ alkyl)$_z$, —$OC(=O)(C_{1-3}$ alkyl), —$OC(=O)O(C_{1-3}$ alkyl), —OC(=O)NH$_{2-z}$(C$_{1-3}$ alkyl)$_z$, —NHC(=O)(C$_{1-3}$ alkyl), —NHC(=O)NH$_{2-z}$(C$_{1-3}$ alkyl)$_z$, —NHC(=NH) NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; and X$^1$ and X$^2$ are independently selected from O, S, and N(R$^{84}$), wherein R$^{84}$ is —H or C$_{1-3}$ alkyl.

In one embodiment, the pyrone derivative has the formula (Ia) or (Ib)

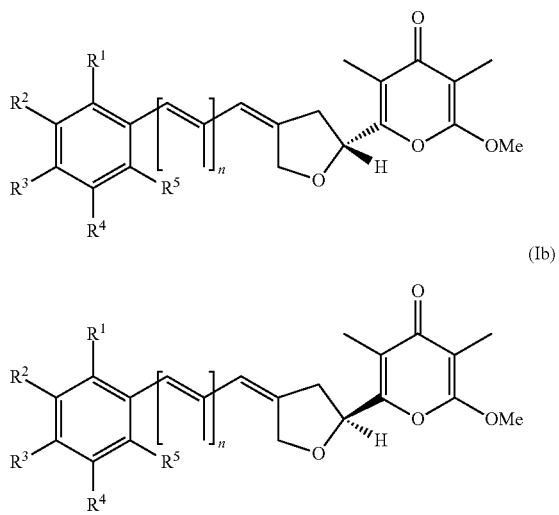

wherein R$^1$ to R$^5$ and n are as defined above or below.

In any of the above embodiments (in particular with respect to formulas (I), (Ia), and (Ib)), at least one of R$^1$ to R$^5$ may be hydrogen and the rest of R$^1$ to R$^5$ is as defined above or below. Thus, in one example of any of the above embodiments (in particular with respect to formulas (I), (Ia), and (Ib)), at least one of R$^1$ to R$^5$ (e.g., at least R$^1$, or at least R$^2$, or at least R$^3$, or at least R$^4$ or at least R$^5$) is hydrogen and the rest of R$^1$ to R$^5$ is as defined above or below. In a further example of any of the above embodiments (in particular with respect to formulas (I), (Ia), and (Ib)), at least two of R$^1$ to R$^5$ (e.g., at least R$^1$ and R$^2$; at least R$^1$ and R$^3$; at least R$^1$ and R$^4$; at least R$^1$ and R$^5$; at least R$^2$ and R$^3$; at least R$^2$ and R$^4$; at least R$^2$ and R$^5$; at least R$^3$ and R$^4$; at least R$^3$ and R$^5$; or at least R$^4$ and R$^5$) are hydrogen and the rest of R$^1$ to R$^5$ is as defined above or below. In a further example of any of the above embodiments (in particular with respect to formulas (I), (Ia), and (Ib)), at least three of R$^1$ to R$^5$ (e.g., at least R$^1$, R$^2$ and R$^3$; or at least R$^1$, R$^2$ and R$^4$; at least R$^1$, R$^2$ and R$^5$; at least R$^1$, R$^3$ and R$^4$; at least R$^1$, R$^3$ and R$^5$; at least R$^1$, R$^4$ and R$^5$; at least R$^2$, R$^3$ and R$^4$; at least R$^2$, R$^3$ and R$^5$; at least R$^2$, R$^4$ and R$^5$; or at least R$^3$, R$^4$ and R$^5$) are hydrogen and the rest of R$^1$ to R$^5$ is as defined above or below. In a further example of any of the above embodiments (in particular with respect to formulas (I), (Ia), and (Ib)), at least four of R$^1$ to R$^5$ (e.g., at least R$^1$, R$^2$, R$^3$ and R$^4$; or at least R$^1$, R$^2$, R$^3$ and R$^5$; at least R$^1$, R$^2$, R$^4$ and R$^5$; at least R$^1$, R$^3$, R$^4$ and R$^5$; or at least R$^2$, R$^3$, R$^4$ and R$^5$) are hydrogen and the rest of R$^1$ to R$^5$ is as defined above or below.

In one particular example of any of the above embodiments (in particular with respect to formulas (I), (Ia), and (Ib)), one of R$^1$ to R$^5$ (e.g., R$^1$, R$^2$, R$^3$, R$^4$, or R$^5$) is hydrogen and the rest of R$^1$ to R$^5$ is other than hydrogen. In a further particular example of any of the above embodiments (in particular with respect to formulas (I), (Ia), and (Ib)), two of R$^1$ to R$^5$ (e.g., R$^1$ and R$^2$; R$^1$ and R$^3$; R$^1$ and R$^4$; R$^1$ and R$^5$; R$^2$ and R$^3$; R$^2$ and R$^4$; R$^2$ and R$^5$; R$^3$ and R$^4$; R$^3$ and R$^5$; or R$^4$ and R$^5$) is hydrogen and the rest of R$^1$ to R$^5$ is other than hydrogen. In a further particular example of any of the above embodiments (in particular with respect to formulas (I), (Ia), and (Ib)), three of R$^1$ to R$^5$ (e.g., R$^1$, R$^2$ and R$^3$; R$^1$, R$^2$ and R$^4$; R$^1$, R$^2$ and R$^5$; R$^1$, R$^3$ and R$^4$; R$^1$, R$^3$ and R$^5$; R$^1$, R$^4$ and R$^5$; R$^2$, R$^3$ and R$^4$; R$^2$, R$^4$, R$^3$ and R$^5$; R, and R$^5$; or R$^3$, R$^4$ and R$^5$) are hydrogen and the rest of R$^1$ to R$^5$ is other than hydrogen. In a further particular example of any of the above embodiments (in particular with respect to formulas (I), (Ia), and (Ib)), four of R$^1$ to R$^5$ (e.g., R$^1$, R$^2$, R$^3$ and R$^4$; R$^1$, R$^2$, R$^3$ and R$^5$; R$^1$, R$^2$, R$^4$ and R$^5$; R$^1$, R$^3$, R$^4$ and R$^5$; or R$^2$, R$^3$, R$^4$ and R$^5$) are hydrogen and the rest of R$^1$ to R$^5$ is other than hydrogen. In a further example of any of the above embodiments (in particular with respect to formulas (I), (Ia), and (Ib)), R$^1$ to R$^5$ are hydrogen.

In one exemplary embodiment of the pyrone derivative, wherein at least two of R$^1$ to R$^5$ are hydrogen, the derivative has the formula (Ic)

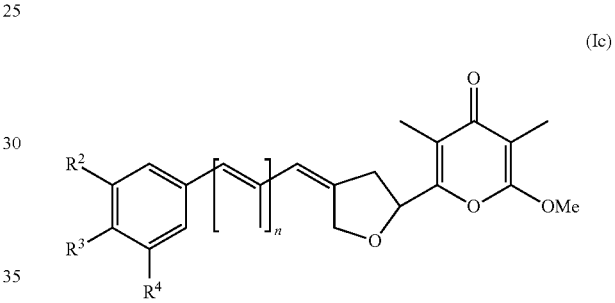

wherein R$^2$ to R$^4$ are as defined above or below.

In exemplary embodiments of the pyrone derivative, wherein at least three of R$^1$ to R$^5$ are hydrogen, the derivative has the formula (Id) or (Ie)

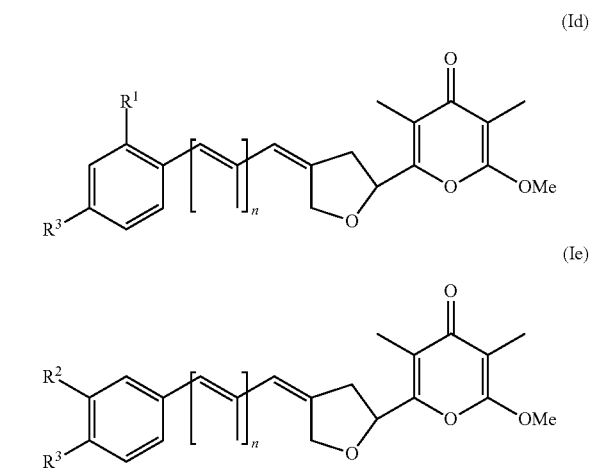

wherein R$^1$ to R$^3$ are as defined above or below.

In exemplary embodiments of the pyrone derivative, wherein at least four of R$^1$ to R$^5$ are hydrogen, the derivative has the formula (If), (Ig) or (Ih)

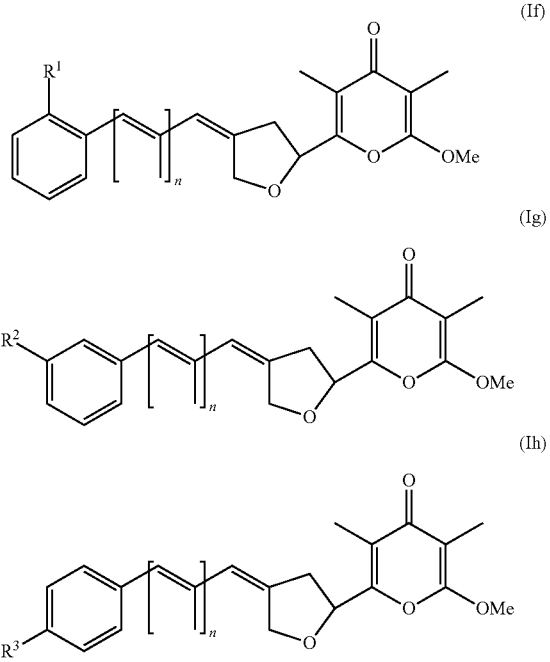

wherein R¹ to R³ are as defined above or below.

In any of the above embodiments (in particular with respect to formulas (I), (Ia), (Ib), (Ic), (Id), (Ie), and (Ih)), $R^3$ may be selected from the group consisting of hydrogen, halogen, methoxy, methyl, trifluoromethyl, and nitro. In one embodiment, $R^3$ is nitro. In another embodiment, $R^3$ may be selected from the group consisting of hydrogen, halogen, methoxy, methyl, and trifluoromethyl. In some embodiments $R^3$ may be selected from the group consisting of hydrogen, halogen, methoxy, methyl, trifluoromethyl, tert-butyl, —S(O)$_2$—CH$_3$, —NH—S(O)$_2$—CH$_3$ and nitro. In some embodiments $R^3$ may be chloro. In some embodiments $R^3$ may be iodo. In some embodiments $R^3$ may be tert-butyl. In some embodiments $R^3$ may be trifluoromethyl. In some embodiments $R^3$ may be —S(O)$_2$—CH$_3$. In some embodiments $R^3$ may be —NH—S(O)$_2$—CH$_3$.

In one embodiment, the pyrone derivative has the formula (I), (Ia), (Ib), (Ic), or (Ie), wherein $R^2$ and $R^3$ are taken together with the atoms to which they are attached to form a 6-membered cycloaliphatic ring; and $R^4$ and n are as defined above or below. For example, $R^4$ may be hydrogen.

In one embodiment, the pyrone derivative has the formula (I), (Ia), (Ib), (Ic), or (Ie), wherein $R^2$ and $R^3$ are taken together with the atoms to which they are attached to form a 6-membered aromatic ring (e.g., phenyl); and $R^4$ and n are as defined above or below. For example, $R^4$ may be hydrogen.

In one embodiment, the pyrone derivative has the formula (I), (Ia), (Ib), (Ic), (Id), (Ie) or (Ih), wherein $R^3$ is selected from the group consisting of halogen (e.g., fluoro, chloro or iodo), nitro, —OR$^{11}$, alkyl, —S(O)$_{0-2}$R$^{11}$, —N(R$^{11}$)S(O)$_{1\text{-}2}$R$^{11}$, and —C(=X)XR$^{11}$, wherein the alkyl group is substituted with from 0 to 3 independently selected $R^{30}$.

In one embodiment, the pyrone derivative has the formula (I), (Ia), (Ib), (Ic), (Id), or (Ie), wherein two of R¹ to R⁵ (such as R¹ and R²; R¹ and R³; R¹ and R⁴; R¹ and R⁵; R² and R³; R² and R⁴; R² and R⁵; R³ and R⁴; R³ and R⁵; or R⁴ and R⁵, preferably R¹ and R³ or R² and R³) are selected from halogen and —OR$^{11}$. In some embodiments R¹ and R³ are each fluoro. In some embodiments R² and R³ are each methoxy.

In one embodiment, the pyrone derivative has the formula (I), (Ia), (Ib), (Ic), (Id), (Ie), or (Ih), wherein R¹, R², R⁴, and R⁵ are each hydrogen; and $R^3$ is selected from the group consisting of hydrogen, halogen, methoxy, methyl, nitro, trifluoromethyl, tert-butyl, —C(O)NH$_2$, —S(O)$_2$—CH$_3$, and —NH—S(O)$_2$—CH$_3$; and n is 1, 2, or 3, such as 1 or 3. For example, $R^3$ is nitro. Alternatively, $R^3$ is selected from the group consisting of hydrogen, halogen, methoxy, methyl, trifluoromethyl, tert-butyl, —C(O)NH$_2$, —S(O)$_2$—CH$_3$, and —NH—S(O)$_2$—CH$_3$, such as hydrogen, halogen, methoxy, and methyl. In some embodiments $R^3$ is selected from the group consisting of halogen, trifluoromethyl, tert-butyl, —S(O)$_2$—CH$_3$, —NH—S(O)$_2$—CH$_3$ and nitro. In some embodiments $R^3$ may be halo. In some embodiments $R^3$ may be chloro. In some embodiments $R^3$ may be iodo. In some embodiments $R^3$ may be tert-butyl. In some embodiments $R^3$ may be trifluoromethyl. In some embodiments $R^3$ may be —S(O)$_2$—CH$_3$. In some embodiments $R^3$ may be —NH—S(O)$_2$—CH$_3$.

In one embodiment, the pyrone derivative has the formula (I), (Ia), (Ib), (Ic), (Ie), or (Ig), wherein R¹, R³, R⁴, and R⁵ are each hydrogen; $R^2$ is nitro; and n is 1, 2, or 3, such as 1 or 3.

In one embodiment, the pyrone derivative has the formula (I), (Ia), (Ib), (Id), or (If), wherein R², R³, R⁴, and R⁵ are each hydrogen; $R^1$ is halogen; and n is 1, 2, or 3, such as 1 or 3.

In one embodiment, the pyrone derivative has the formula (I), (Ia), (Ib), (Ic), (Ie), or (Ig), wherein R¹, R³, R⁴, and R⁵ are each hydrogen; $R^2$ is halogen (such as fluoro or chloro); and n is 1, 2, or 3, such as 1 or 3.

In one embodiment, the pyrone derivative has the formula (I), (Ia), (Ib), or (Id), wherein R², R⁴, and R⁵ are each hydrogen; R¹ and R³ are each halogen (such as fluoro or chloro); and n is 1, 2, or 3, such as 1 or 3. In some embodiments R¹ and R³ are each fluoro.

In one embodiment, the pyrone derivative has the formula (I), (Ia), (Ib), or (Ie), wherein R¹, R⁴, and R⁵ are each hydrogen; R² and R³ are each —O(C$_{1\text{-}3}$ alkyl) (such as methoxy); and n is 1, 2, or 3, such as 1 or 3. In some embodiments R² and R³ are each methoxy.

In any of the above embodiments with respect to formula (II), at least one of R⁶ to R¹⁰ may be hydrogen and the rest of R⁶ to R¹⁰ is as defined above or below. Thus, in one example of any of the above embodiments with respect to formula (II), at least one of R⁶ to R¹⁰ (e.g., at least R⁶, or at least R⁷, or at least R⁸, or at least R⁹ or at least R¹⁰) is hydrogen and the rest of R⁶ to R¹⁰ is as defined above or below. In a further example of any of the above embodiments with respect to formula (II), at least two of R⁶ to R¹⁰ (e.g., at least R⁶ and R⁷; at least R⁶ and R⁸; at least R⁶ and R⁹; at least R⁶ and R¹⁰; at least R⁷ and R⁸; at least R⁷ and R⁹; at least R⁷ and R¹⁰; at least R⁸ and R⁹; at least R⁸ and R¹⁰; or at least R⁹ and R¹⁰) are hydrogen and the rest of R⁶ to R¹⁰ is as defined above or below. In a further example of any of the above embodiments with respect to formula (II), at least three of R⁶ to R¹⁰ (e.g., at least R⁶, R⁷ and R⁸; or at least R⁶, R⁷ and R⁹; at least R⁶, R⁷ and R¹⁰; at least R⁶, R⁸ and R⁹; at least R⁶, R⁸ and R¹⁰; at least R⁶, R⁹ and R¹⁰; at least R⁷, R⁸ and R⁹; at least R⁷, R⁸ and R¹⁰; at least R⁷, R⁹ and R¹⁰; or at least R⁸, R⁹ and R¹⁰) are hydrogen and the rest of R⁶ to R¹⁰ is as defined above or below. In a further example of any of the above embodiments with respect to formula (II), at least four of R⁶ to R¹⁰ (e.g., at least R⁶, R⁷, R⁸ and R⁹; or at least R⁶, R⁷, R⁸ and R¹⁰; at least R⁶, R⁷, R⁹ and R¹⁰; at least $R^6$, $R^8$, $R^9$ and $R^{10}$; or at least $R^7$, $R^8$, $R^9$ and $R^{10}$) are hydrogen and the rest of $R^6$ to $R^{10}$ is as defined above or below.

In one particular example of any of the above embodiments with respect to formula (II), one of $R^6$ to $R^{10}$ (e.g., $R^6$, $R^7$, $R^8$, $R^9$, or $R^{10}$) is hydrogen and the rest of $R^6$ to $R^{10}$ is other than hydrogen. In a further particular example of any of the above embodiments with respect to formula (II), two of $R^6$ to $R^{10}$ (e.g., $R^6$ and $R^7$; $R^6$ and $R^8$; $R^6$ and $R^9$; $R^6$ and $R^{10}$; $R^7$ and $R^8$; $R^7$ and $R^9$; $R^7$ and $R^{10}$; $R^8$ and $R^9$; $R^8$ and $R^{10}$; or $R^9$ and $R^{10}$) is hydrogen and the rest of $R^6$ to $R^{10}$ is other than hydrogen. In a further particular example of any of the above embodiments with respect to formula (II), three of $R^6$ to $R^{10}$ (e.g., $R^6$, $R^7$ and $R^8$; $R^6$, $R^7$ and $R^9$; $R^6$, $R^7$ and $R^{10}$; $R^6$, $R^8$ and $R^9$; $R^6$, $R^8$ and $R^{10}$; $R^6$, $R^9$ and $R^{10}$; $R^7$, $R^8$ and $R^9$; $R^7$, $R^8$ and $R^{10}$; $R^7$, $R^9$ and $R^{10}$; or $R^8$, $R^9$ and $R^{10}$) are hydrogen and the rest of $R^6$ to $R^{10}$ is other than hydrogen. In a further particular example of any of the above embodiments with respect to formula (II), four of $R^6$ to $R^{10}$ (e.g., $R^6$, $R^7$, $R^8$ and $R^9$; $R^6$, $R^7$, $R^8$ and $R^{10}$; $R^6$, $R^7$, $R^9$ and $R^{10}$; $R^6$, $R^8$, $R^9$ and $R^{10}$; or $R^7$, $R^8$, $R^9$ and $R^{10}$) are hydrogen and the rest of $R^6$ to $R^{10}$ is other than hydrogen. In a further example of any of the above embodiments with respect to formula (II), $R^6$ to $R^{10}$ are hydrogen.

In one exemplary embodiment of the pyrone derivative, wherein at least two of $R^6$ to $R^{10}$ are hydrogen, the derivative has the formula (IIa)

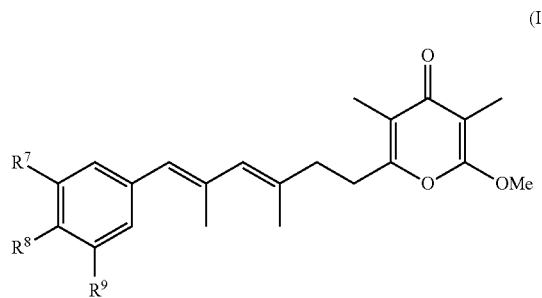

(IIa)

wherein $R^7$ to $R^9$ are as defined above or below.

In exemplary embodiments of the pyrone derivative, wherein at least three of $R^6$ to $R^{10}$ are hydrogen, the derivative has the formula (IIb) or (IIc)

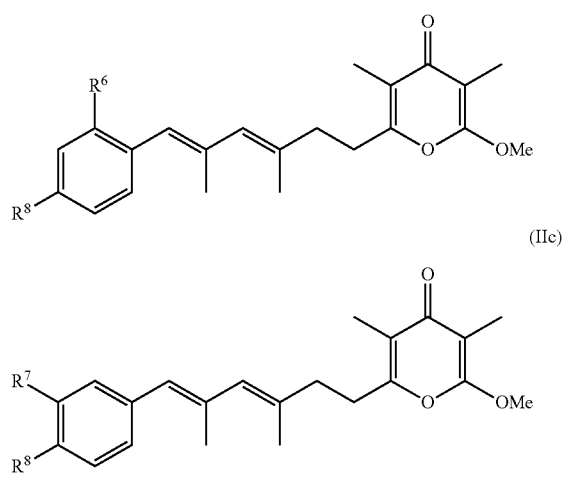

(IIb)

(IIc)

wherein $R^6$ to $R^8$ are as defined above or below.

In exemplary embodiments of the pyrone derivative, wherein at least four of $R^6$ to $R^{10}$ are hydrogen, the derivative has the formula (IId), (IIe) or (IIf)

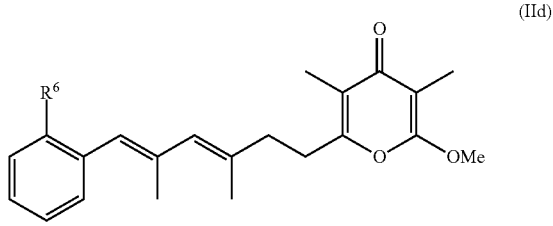

(IId)

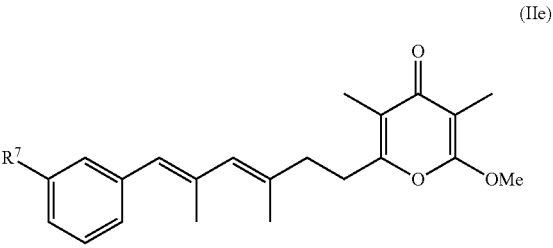

(IIe)

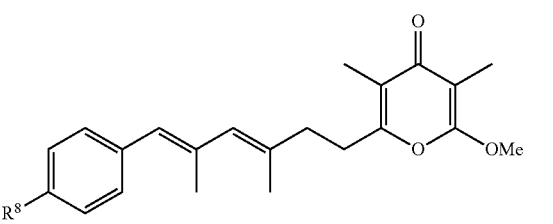

(IIf)

wherein $R^6$ to $R^8$ are defined as above or below.

In any of the above embodiments (in particular with respect to formula (II), (IIa), (IIb), (IIc), and (IIf)), $R^8$ may be selected from the group consisting of hydrogen, halogen, cyano, methoxy, methyl, and nitro. In one embodiment, $R^8$ is nitro. In another embodiment, $R^8$ may be selected from the group consisting of hydrogen, halogen, cyano, methoxy, and methyl. In some embodiments $R^8$ is cyano. In some embodiments $R^8$ is halogen, preferably chloro.

In one embodiment, the pyrone derivative has the formula (II), (IIa), or (IIc), wherein $R^7$ and $R^8$ are taken together with the atoms to which they are attached to form a 6-membered cycloaliphatic ring; and $R^9$ is defined above or below. For example, $R^9$ may be hydrogen.

In one embodiment, the pyrone derivative has the formula (II), (IIa), or (IIc), wherein $R^7$ and $R^8$ are taken together with the atoms to which they are attached to form a 6-membered aromatic ring (such as phenyl); and $R^9$ is defined above or below. For example, $R^9$ may be hydrogen.

In one embodiment, the pyrone derivative has the formula (II), (IIa), (IIb), (IIc), or (IIf)), wherein $R^8$ is selected from the group consisting of halogen (e.g., fluoro or chloro), nitro, —$OR^{11}$, alkyl, —$S(O)_{0-2}R^{11}$, —$N(R^{11})S(O)_{12}R^{11}$, and —$C(=X)XR^{11}$, wherein the alkyl group is substituted with from 0 to 3 independently selected $R^{30}$.

In one embodiment, the pyrone derivative has the formula (II), (IIa), (IIb), or (IIc), wherein two of $R^6$ to $R^{10}$ (such as $R^6$ and $R^7$; $R^6$ and $R^8$; $R^6$ and $R^9$; $R^6$ and $R^{10}$; $R^7$ and $R^8$; $R^7$ and $R^9$; $R^7$ and $R^{10}$; $R^8$ and $R^9$; $R^8$ and $R^{10}$; or $R^9$ and $R^{10}$, preferably $R^6$ and $R^8$ or $R^7$ and $R^8$) are selected from halogen and —$OR^{11}$.

In one embodiment, the pyrone derivative has the formula (II), (IIa), (IIb), (IIc), or (IIf), wherein $R^6$, $R^7$, $R^9$, and $R^{10}$ are each hydrogen; and $R^8$ is selected from the group consisting of hydrogen, halogen, cyano, methoxy, methyl, and nitro. For example, $R^8$ is nitro. Alternatively, $R^8$ is selected from the group consisting of hydrogen, halogen, cyano, methoxy, and methyl. In some embodiments $R^8$ is cyano. In some embodiments $R^8$ is halogen, preferably chloro.

In one embodiment, the pyrone derivative has the formula (II), (IIa), (IIc), or (IIe), wherein $R^6$, $R^8$, $R^9$, and $R^{10}$ are each hydrogen; and $R^7$ is nitro.

In one embodiment, the pyrone derivative has the formula (II), (IIb), or (IId), wherein $R^7$, $R^8$, $R^9$, and $R^{10}$ are each hydrogen; and $R^6$ is halogen.

In one embodiment, the pyrone derivative has the formula (II), (IIa), (IIc), or (IIe), wherein $R^6$, $R^8$, $R^9$, and $R^{10}$ are each hydrogen; and $R^7$ is halogen (such as fluoro or chloro).

In one embodiment, the pyrone derivative has the formula (II) or (IIb), wherein $R^7$, $R^9$, and $R^{10}$ are each hydrogen; and $R^6$ and $R^8$ are each halogen (such as fluoro or chloro).

In one embodiment, the pyrone derivative has the formula (II), (IIa), or (IIc), wherein $R^6$, $R^9$, and $R^{10}$ are each hydrogen; and $R^7$ and $R^8$ are each —O($C_{1-3}$ alkyl) (such as methoxy).

In one embodiment, the compound used in the invention is selected from the compounds shown in Table 1.

It is intended that the compounds used in the present invention (in particular, the compounds of any one of formulas (I), (Ia), (Ib), (Ic), (Id), (Ie), (If), (Ig), (Ih), (II), (IIa), (IIb), (IIc), (IId), (IIe), and (IIf) such as those depicted in Table 1, below) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof. In some embodiments the invention encompass the compounds 2, 4, 6, 7, 9, 10, 11, 12, 13, 14, 19, 20, 21, 22, 23, 24, 26, 27 and 28, preferably 2, 4, 6, 7, 9, 11, 20, 21, 22, 23, 24, 26 and 27, more preferably 2, 4, 6, 7, 21, 22, 24 and 27, even more preferably 2, 4, 6, 7, 21, 22 and 27, and their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically enriched forms, prodrugs, and any combinations thereof.

A selection of compounds which can be used according to the present invention is listed in the following Table 1. These compounds are designated as Compound 1 to Compound 28.

TABLE 1

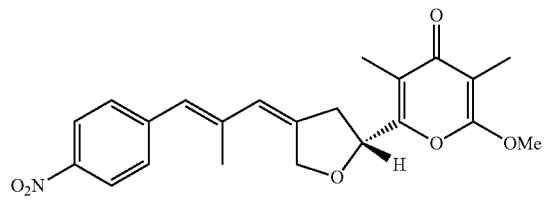 [SMILES: COc1oc([C@H]2C/C(=C/C(C)=C/c3ccc([N+](=O)[O-])cc3)CO2)c(C)c(=O)c1C]

1

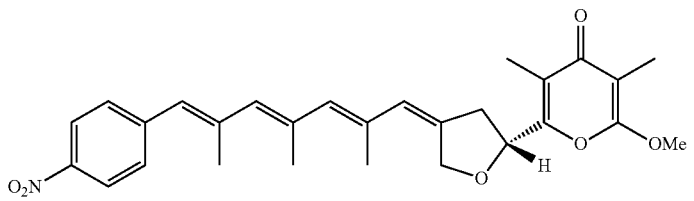 [SMILES: COc1oc([C@H]2C/C(=C/C(C)=C/C(C)=C/C(C)=C/c3ccc([N+](=O)[O-])cc3)CO2)c(C)c(=O)c1C]

2

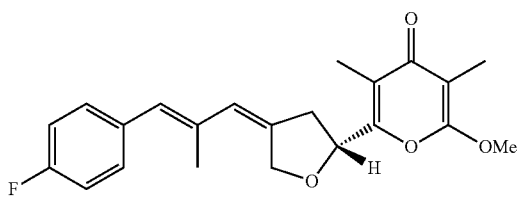

3

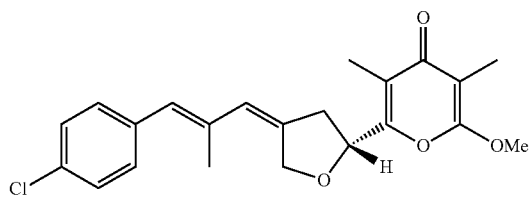

4

TABLE 1-continued
| | |
|---|---|
| 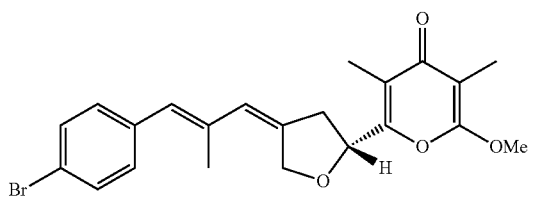 [SMILES: COc1oc([C@H]2C/C(=C/C(C)=C/c3ccc(Cl)cc3)CO2)c(C)c(=O)c1C] | 5 |
| 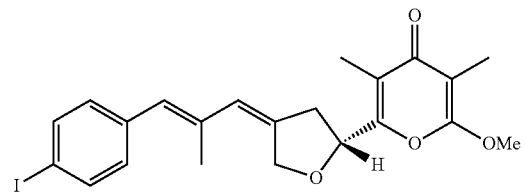 [SMILES: COc1oc([C@H]2C/C(=C/C(C)=C/c3ccc(I)cc3)CO2)c(C)c(=O)c1C] | 6 |
| 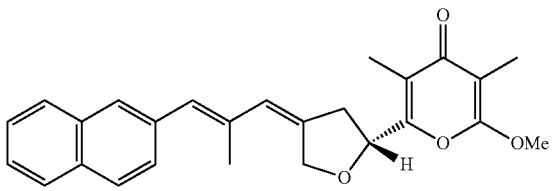 [SMILES: COc1oc([C@H]2C/C(=C/C(C)=C/c3ccc4ccccc4c3)CO2)c(C)c(=O)c1C] | 7 |
| 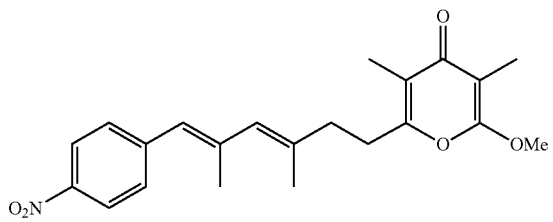 [SMILES: COc1oc(CC/C(C)=C/C(C)=C/c2ccc([N+](=O)[O-])cc2)c(C)c(=O)c1C] | 8 |
| 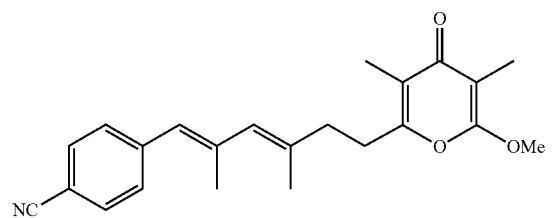 [SMILES: COc1oc(CC/C(C)=C/C(C)=C/c2ccc(C#N)cc2)c(C)c(=O)c1C] | 9 |
| 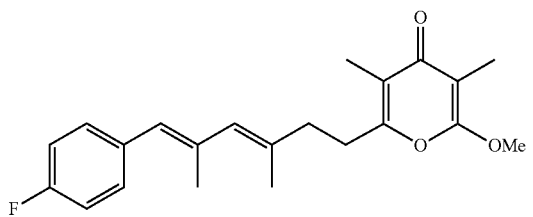 [SMILES: COc1oc(CC/C(C)=C/C(C)=C/c2ccc(F)cc2)c(C)c(=O)c1C] | 10 |
| 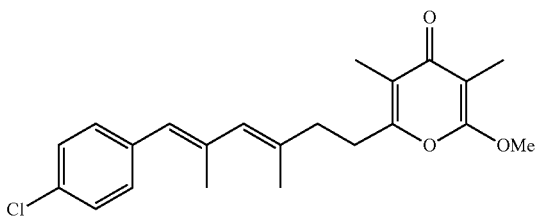 [SMILES: COc1oc(CC/C(C)=C/C(C)=C/c2ccc(Cl)cc2)c(C)c(=O)c1C] | 11 |

TABLE 1-continued
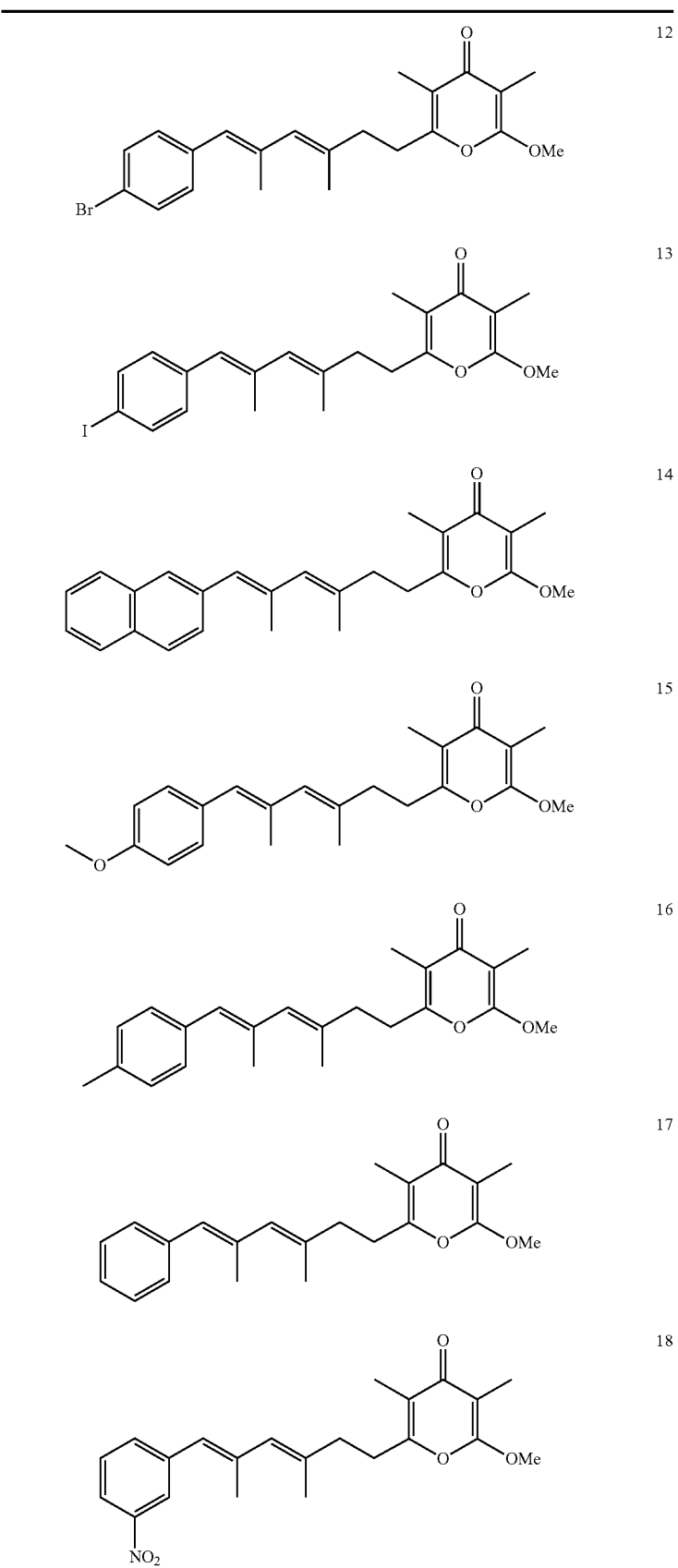

TABLE 1-continued
| | |
|---|---|
| 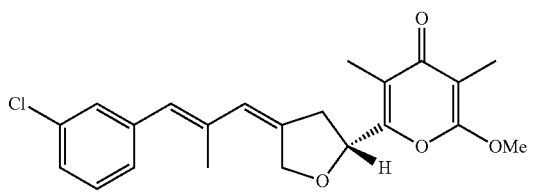 [SMILES: COc1oc([C@H]2C/C(=C/C(C)=C/c3cccc(Cl)c3)CO2)c(C)c(=O)c1C] | 19 |
| 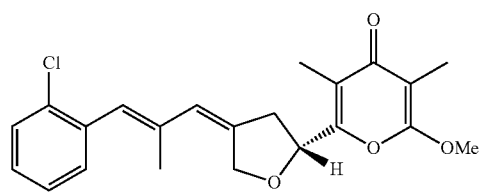 [SMILES: COc1oc([C@H]2C/C(=C/C(C)=C/c3ccccc3Cl)CO2)c(C)c(=O)c1C] | 20 |
| 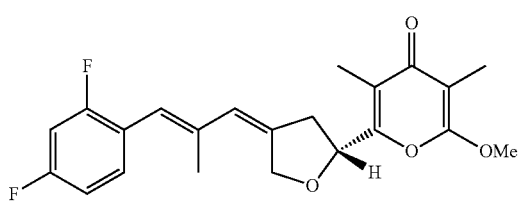 [SMILES: COc1oc([C@H]2C/C(=C/C(C)=C/c3ccc(F)cc3F)CO2)c(C)c(=O)c1C] | 21 |
| 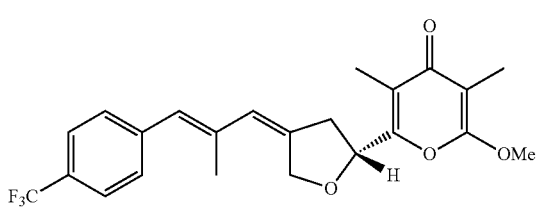 [SMILES: COc1oc([C@H]2C/C(=C/C(C)=C/c3ccc(C(F)(F)F)cc3)CO2)c(C)c(=O)c1C] | 22 |
| 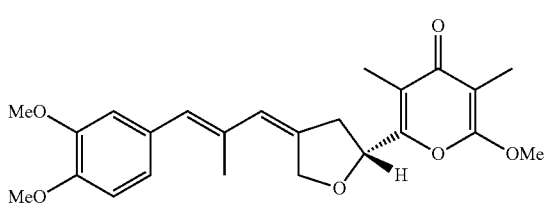 [SMILES: COc1ccc(/C=C(C)/C=C2\CO[C@@H](c3oc(OC)c(C)c(=O)c3C)C2)cc1OC] | 23 |
| 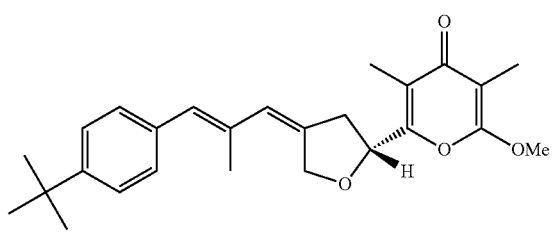 [SMILES: COc1oc([C@H]2C/C(=C/C(C)=C/c3ccc(C(C)(C)C)cc3)CO2)c(C)c(=O)c1C] | 24 |
| 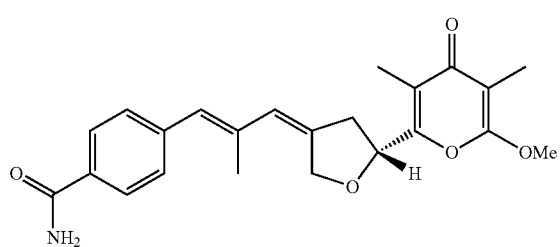 [SMILES: COc1oc([C@H]2C/C(=C/C(C)=C/c3ccc(C(N)=O)cc3)CO2)c(C)c(=O)c1C] | 25 |

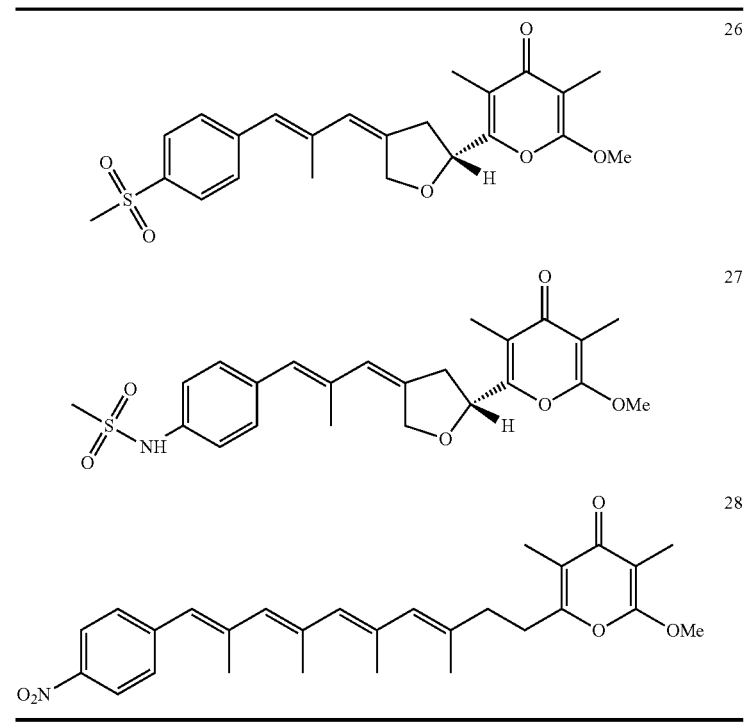

In some embodiments the used pyrone derivative is selected from the group consisting of:
2-methoxy-3,5-dimethyl-6-{(2R,4Z)-4-[(2E)-2-methyl-3-(4-nitrophenyl)prop-2-en-1-ylidene]tetra-hydrofuran-2-yl}-4H-pyran-4-one;
2-methoxy-3,5-dimethyl-6-{(2R,4Z)-4-[(2E,4E,6E)-2,4,6-trimethyl-7-(4-nitrophenyl)hepta-2,4,6-trien-1-ylidene]tetrahydrofuran-2-yl}-4H-pyran-4-one;
2-methoxy-3,5-dimethyl-6-{(2R,4Z)-4-[(2E)-2-methyl-3-(4-fluorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(4-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(4-bromophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(4-iodophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(naphtalen-2-yl)prop-2-en-1-ylidene]tetra-hydrofuran-2-yl}-4H-pyran-4-one;
2-[(3E,5E)-6-(4-nitrophenyl)-3,5-dimethylhexa-3,5-dien-1-yl]-6-methoxy-3,5-dimethyl-4H-pyran-4-one;
4-[(1E,3E)-6-(6-methoxy-3,5-dimethyl-4-oxo-4H-pyran-2-yl)-2,4-dimethylhexa-1,3-dien-1-yl]b enzo-nitrite;
2-[(3E,5E)-6-(4-fluorophenyl)-3,5-dimethylhexa-3,5-dien-1-yl]-6-methoxy-3,5-dimethyl-4H-pyran-4-one;
2-[(3E,5E)-6-(4-chlorophenyl)-3,5-dimethylhexa-3,5-dien-1-yl]-6-methoxy-3,5-dimethyl-4H-pyran-4-one;
2-[(3E,5E)-6-(4-bromophenyl)-3,5-dimethylhexa-3,5-dien-1-yl]-6-methoxy-3,5-dimethyl-4H-pyran-4-one;
2-[(3E,5E)-6-(4-iodophenyl)-3,5-dimethylhexa-3,5-dien-1-yl]-6-methoxy-3,5-dimethyl-4H-pyran-4-one;
2-[(3E,5E)-6-(naphtalen-2-yl)-3,5-dimethylhexa-3,5-dien-1-yl]-6-methoxy-3,5-dimethyl-4H-pyran-4-one;
2-methoxy-3,5-dimethyl-6-{(2R,4Z)-4-[(2E)-2-methyl-3-(3-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(2-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(2,4-difluorophenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(4-trifluoromethylphenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(3,4-dimethoxyphenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(4-tert-butylphenyl)prop-2-en-1-ylidene]tetrahydrofuran-2-yl}-4H-pyran-4-one;
4-{(1E,3Z)-3-[(5R)-5-(6-methoxy-3,5-dimethyl-4-oxo-4H-pyran-2-yl)dihydrofuran-3(2H)-ylidene]-2-methylprop-1-en-1-yl}benzamide;
2-methoxy-3,5-dimethyl-6-{(2R,4Z)-4-[(2E)-2-methyl-3-(4-(methylsulfonyl)phenyl)prop-2-en-1-ylidene]tetrahydrofuran-2-yl}-4H-pyran-4-one;
N-(4-{(1E,3Z)-3-[(5R)-5-(6-methoxy-3,5-dimethyl-4-oxo-4H-pyran-2-yl)dihydrofuran-3(2H)-ylidene]-2-methylprop-1-en-1-yl}) methane sulfonamide;
2-methoxy-3,5-dimethyl-6-{(2R,4Z)-4-[(2E)-2-methyl-3-(2-naphthalenyl)prop-2-en-1-ylidene]tetrahydrofuran-2-yl}-4H-pyran-4-one; and
2-[(3E,5E,7E,9E)-10-(4-nitrophenyl)-3,5,7,9-tetramethyldecan-3,5,7,9-tetraen-1-yl]-6-methoxy-3,5-dimethyl-4H-pyran-4-one.

The compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) which contain a basic functionality may form salts with a variety of inorganic or organic acids. The compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) which contain an acidic functionality may form salts with a variety of inorganic or organic bases. Exemplary inorganic and organic acids/bases as well as exemplary acid/base addition salts of the compounds used in the present invention are given in the definition of "pharmaceutically acceptable salt" in the section "Pharmaceutical composition", below. The compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) which contain both basic and acidic functionalities may be converted into either base or acid addition salt. The neutral forms of the compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) may be regenerated by contacting the salt with a base or acid and isolating the parent compound in the conventional manner.

The compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) may be in a prodrug form. Prodrugs of the compounds used in the present invention are those compounds that upon administration to an individual undergo chemical conversion under physiological conditions to provide the compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)). Additionally, prodrugs can be converted to the compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) by chemical or biochemical methods in an ex vivo environment. For example, prodrugs can be slowly converted to the compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) when, for example, placed in a transdermal patch reservoir with a suitable enzyme or chemical reagent. Exemplary prodrugs are esters or amides which are hydrolyzable in vivo.

In certain embodiments, the pyrone compounds described herein exhibit pharmacological properties (effectiveness against virus strains which are resistant to one or more known antiviral drugs; effectiveness against persistent diseases; toxicity; bioavailability; side effects; dosing; patient compliance; compatibility; stability; half-life; etc.), which are in at least one aspect superior to the pharmacological properties exhibited by one or more of known antiviral drugs such as those described herein. In one embodiment, the pyrone compounds described herein are more effective against virus strains (in particular virus strains of an animal pathogenic virus as disclosed herein) which are resistant to one or more known antiviral drugs. In one embodiment, the pyrone compounds described herein are more effective against a persistent disease caused by the animal pathogenic virus compared to one or more known antiviral drugs. In one embodiment, the pyrone compounds described herein can be administered in lower doses compared to one or more known antiviral drugs (preferably, without altering the therapeutic outcome). Preferably, the known antiviral drugs are selected from the group consisting of maraviroc, enfuvirtide, zidovudine, didanosine, zalcitabine, stavudine, lamivudine, abacavir, emtricitabine, entecavir, tenofovir, adefovir, efavirenz, nevirapine, delavirdine, etravirine, rilpivirine, raltegravir, elvitegravir, dolutegravir, saquinavir, ritonavir, indinavir, nelfinavir, amprenavir, boceprevir, telaprevir, lopinavir, atazanavir, fosamprenavir, tipranavir, darunavir, amantadine, rimantidine, rifampicin, zanamivir, and oseltamivir. In one embodiment, the known antiviral drugs are selected from the group consisting of enfuvirtide, zidovudine, raltegravir, and saquinavir.

The compounds used in the present invention (in particular those specified above such as those of formula (I), (Ia), (Ib), (Ic), (Id), (Ie), (If), (Ig), (Ih), (II), (IIa), (IIb), (IIc), (IId), (IIe), or (IIf)) can be prepared as described below or prepared by methods analogous thereto, which are readily known and available to one of ordinary skill in the art of organic synthesis.

For example, the compounds used in the present invention can be prepared by mutasynthesis or chemical synthesis.

Mutasynthesis is the combination of chemical semisynthesis with biosynthesis; cf., e.g., Weist et al., *Appl. Microbiol. Biotechnol.* 2005, 68, 141-150; and Rinehart et al., *Pure appl. Chem.* 1977, 49, 1361-1384. In particular, for mutasynthesis, biosynthetic mutants are generated which are fed with a muthasynthon and the metabolites thus generated are isolated. For example, compounds of formula (I) or (II) can be synthesized by methods which are identical or similar to those described in Werneburg et al., *J. Am. Chem. Soc.* 2010, 132, 10407-10413 and EP 2 108 650 A1. Examples of the biosynthetic mutants used in such methods include a bacterium of the genus *Streptomyces thioletus* (lacking the N-oxygenase gene aurF and the cytochrome P450 monooxygenase gene aurH), *S. lividans*, and *S. albus*. Examples of mutasynthons include compounds of the following formulas:

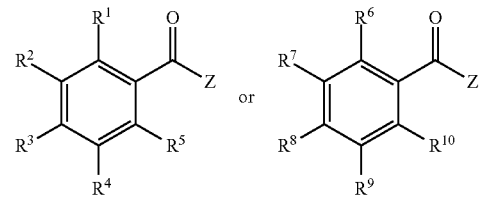

wherein $R^1$ to $R^{10}$ are as defined above and Z is OH or —S—$(CH_2)_2$NHC(O)$CH_3$.

Alternatively, the compounds used in the present invention can be chemically synthesized, e.g., by coupling a compound of the following formula with an appropriate organometal compound:

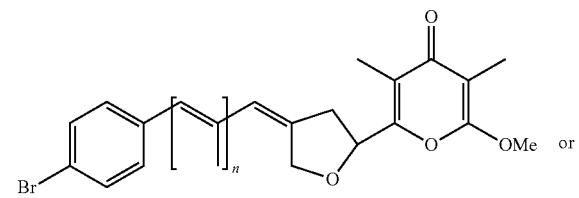

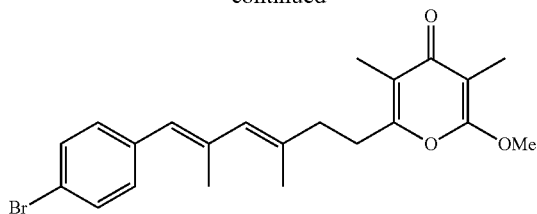

Examples of appropriate organometal compounds include compounds of the formula R'M, wherein M is selected from the group consisting of —Sn(R")$_3$, —Zn(R"), —Al(R")$_3$, —CuR", —InR", and —MgR", wherein R" is alkyl (e.g., methyl, ethyl, or butyl) or cycloalkyl (such as cyclohexyl), and R' is R$^{30}$, folic acid, or a molecular probe. The coupling reaction may be a Stille coupling. The resulting compounds may be derivatized (e.g., with an antibody, anticalin, folic acid, a molecular probe or a linker group, or sulfonated or phosphorylated) as known to the skilled person or described in EP 2 108 650 A1.

Pharmaceutical Compositions

The compounds described in present invention (in particular those specified above such as those of formula (I), (Ia), (Ib), (Ic), (Id), (Ie), (If), (Ig), (Ih), (II), (IIa), (IIb), (IIc), (IId), (IIe), or (IIf), preferably compounds 2, 4, 6, 7, 9, 10, 11, 12, 13, 14, 19, 20, 21, 22, 23, 24, 26, 27 and 28) are preferably administered to a patient in need thereof via a pharmaceutical composition. In one embodiment, the pharmaceutical composition comprises a pyrone derivative as described above (e.g. having the general formula (I), (Ia), (Ib), (Ic), (Id), (Ie), (If), (Ig), (Ih), (II), (IIa), (IIb), (IIc), (IId), (IIe), or (IIf) or a hydrate, solvate, salt, complex, racemic mixture, diastereomer, enantiomer, or tautomer thereof or an isotopically enriched form of any of the foregoing) and one or more pharmaceutically acceptable excipients.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds used in to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrab amine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, Berge et al., "Pharmaceutical Salts", *J. Pharm. Sci.*, 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound used in the present invention, either alone or in combination with one or more additional active compounds, may be coated in a material to protect the active compound(s) from the action of acids and other natural conditions that may inactivate the active compound.

Examples of suitable aqueous and non-aqueous carriers which may be employed in the pharmaceutical compositions used according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions used according to the present invention is contemplated.

Additional active compounds can be administered together with, before or after the compound used in the present invention (in particular that specified above such as those of formula (I), (Ia), (Ib), (Ic), (Id), (Ie), (If), (Ig), (Ih), (II), (IIa), (IIb), (IIc), (IId), (IIe), or (IIf)) or incorporated into the compositions). In one embodiment, the pharmaceutical composition described herein comprises a pyrone derivative as described above (e.g. having the general formula (I), (Ia), (Ib), (Ic), (Id), (Ie), (If), (Ig), (Ih), (II), (IIa), (IIb), (IIc), (IId), (IIe), or (IIf) or a hydrate, solvate, salt, complex, racemic mixture, diastereomer, enantiomer, or tautomer thereof or an isotopically enriched form of any of the foregoing), at least one additional active compound, and one or more pharmaceutically acceptable excipients.

The "additional active compound" (which is not a pyrone derivative having formula (I) or (II) as specified herein) may be selected from any compound which can be used in the treatment of viral infections, such as antiviral drugs (including antibodies) and immunostimulatory agents. Examples of immunostimulatory agents include interferons (e.g., interferon alpha or interferon gamma), interferon derivatives (such pegylated interferons (i.e., interferons bearing a polyethylene glycol group), such as peginterferon alfa, peginterferon alfa-2a, peginterferon alfa-2b, peginterferon Lambda-1a,), other cytokines (such as interleukins (e.g., interleukin 7 (IL-7), IL-1. IL-2, IL-12), tumor necrosis factor and colony-stimulating factor), or agents inducing the production of interferons by the host (e.g., agonists of Toll Like Receptor 3 (TLR3)). The additional active compound may induce an additive or synergistic therapeutic effect.

The pharmaceutical composition described herein may comprise, in addition to the pyrone derivative as described above, at least one, e.g., 1, 2, 3, 4, 5, 6, 7 or 8, additional active compounds. According to the present teaching, the at least additional active compound, for example the antiviral drug and/or immunostimulatory agent, may be formulated together with the pyrone derivative as described above in a single pharmaceutical composition. Alternatively, the pharmaceutical composition may be structured as kit of parts, wherein the pyrone derivative is provided in a first formulation and the at least one additional active compound, for example the antiviral drug and/or immunostimulatory agent, is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the pyrone derivative. Alternatively, the present teaching envisages administering the pyrone derivative formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

The compositions may also contain adjuvants such as preservatives, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the active compounds, which may be used in a suitable hydrated form, and/or the pharmaceutical compositions used according to the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999.).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound used in the present invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7: 27(1984)).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions used according to the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound used according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound used according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound used according to the present invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Actual dosage levels of the active ingredients in the pharmaceutical compositions used according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds used according to the present invention at levels lower than that required in order to achieve the desired therapeutic effect and gradually increase the dosage until the desired effect is achieved. In general, a suitable daily dose of a composition used according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound used according to the present invention to be administered alone, it is preferable to administer the compound as a pharmaceutical formulation/composition.

For oral administration, the pharmaceutical composition used according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the compound is orally administered in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the compound is parenterally administered (e.g., intravenously, intramuscularly, or subcutaneously), in a concentration of at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition used according to the present invention is conveniently delivered in the form of an aerosol spray presentation from a pressurized pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurized aerosol, the dosage unit can be determined by providing a valve to deliver a metered amount. Capsules and cartridges of, for example, gelatine, for use in an inhaler or insufflator can be formulated containing a powder mix of the pharmaceutical composition used according to the present invention and a suitable powder base such as lactose or starch.

The pharmaceutical composition used according to the present invention can be formulated for parenteral administration by injection, for example, by bolus injection or continuous infusion. In one embodiment, the compounds or compositions used according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions used according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition used according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions used according to the present invention which are suitable for vaginal administration also include pessaries, tampons, creams, gels, pastes, foams or spray formulations containing such carriers as are known in the art to be appropriate. Dosage forms for the topical or transdermal administration of compositions used according to the present invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Therapeutic/pharmaceutical compositions can be administered with medical devices known in the art. For example, in a preferred embodiment, a therapeutic/pharmaceutical composition used according to the present invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the compounds used according to the present invention can be formulated to ensure proper distribution in vivo. For example, the blood-brain barrier (BBB) excludes many highly hydrophilic compounds. To ensure that the compounds used according to the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment, the compounds used according to the present invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. The ability of a compound to inhibit viral infection (e.g., to reduce or inhibit the generation of viral progeny) can be evaluated by using an appropriate in vitro assay known to the skilled practitioner, such as the test system EASY-HIT described in Kremb et al., Antimicrob. Agents Chemother. 2010, 54, 5257-5268. Alternatively, the properties of a compound described in the present invention can be evaluated by examining the ability of the compound in appropriate animal model systems known to the skilled practitioner. A therapeutically effective amount of a compound used according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition used according to the invention can also, if desired, be presented in a pack, or dispenser device which can contain one or more unit dosage forms containing the active compound. The pack can for example comprise metal or plastic foil, such as blister pack. The pack or dispenser device can be accompanied with instruction for administration.

The pharmaceutical composition used according to the invention can be administered as sole active agent or can be administered in combination with other therapeutically and/or cosmetically active agents. In one embodiment, the pharmaceutical composition used according to the invention contains, or is administered with, one or more other therapeutically active agents selected from the group consisting of antiviral agents, antibodies (which are directed against an antigen of an animal pathogenic virus or another microorganism (e.g., a pathogenic bacterium or fungi) or against a cancer antigen), agents stimulating the immune system of the subject (e.g., interferons, such as interferon alpha or interferon beta, imiquimod, and resiquimod), and antimicrobial agents.

Therapeutic Applications

Generally, the present invention demonstrates that the pyrone derivatives described herein are capable of inhibiting viral replication.

Thus, in one aspect, the present invention is directed to a compound selected from the group consisting of a pyrone derivative having the general formula (I), (Ia), (Ib), (Ic), (Id), (Ie), (If), (Ig), (Ih), (II), (IIa), (IIb), (IIc), (IId), (IIe), or (IIf) described above (preferably compounds 2, 4, 6, 7, 9, 10, 11, 12, 13, 14, 19, 20, 21, 22, 23, 24, 26, 27 and/or 28) and hydrates, solvates, salts, complexes, racemic mixtures, diastereomers, enantiomers, and tautomers thereof and isotopically enriched forms of any of the foregoing, for use in a method of treating and/or preventing a condition, disorder or disease that is mediated or caused by an animal pathogenic virus which uses cellular mechanisms in the animal host for its replication and/or for its transcription. Optionally, the method comprises the step of administering at least one additional active compound to the animal. The at least one additional active compound can be administered together with, before or after the pyrone derivative.

In a further aspect, the present invention provides a pharmaceutical composition for use in a method and/or preventing a condition, disorder or disease that is mediated or caused by an animal pathogenic virus which uses cellular mechanisms in the animal host for its replication and/or for its transcription, said composition comprising a pyrone derivative as described herein (in particular a pyrone derivative having the general formula (I), (Ia), (Ib), (Ic), (Id), (Ie), (If), (Ig), (Ih), (II), (IIa), (IIb), (IIc), (IId), (IIe), or (IIf), preferably compounds 2, 4, 6, 7, 9, 10, 11, 12, 13, 14, 19, 20, 21, 22, 23, 24, 26, 27 and/or 28), and one or more excipients, and optionally at least one additional active compound. The at least one additional active compound can be administered together with, before or after the pyrone derivative.

In a further aspect, the present invention provides a method for treating and/or preventing a condition, disorder or disease that is mediated or caused by an animal pathogenic virus which uses cellular mechanisms in the animal host for its replication and/or for its transcription, said method comprising administering a therapeutically effective amount of a pyrone derivative as described herein (in particular a therapeutically effective amount of a pyrone derivative having the general formula (I), (Ia), (Ib), (Ic), (Id), (Ie), (If), (Ig), (Ih), (II), (IIa), (IIb), (IIc), (IId), (IIe), or (IIf), preferably compounds 2, 4, 6, 7, 9, 10, 11, 12, 13, 14, 19, 20, 21, 22, 23, 24, 26, 27 and/or 28) to an animal in need thereof. Optionally, the method comprises the step of administering at least one additional active compound to the animal. The at least one additional active compound can be administered together with, before or after the pyrone derivative.

In any of the above therapeutic aspects, the at least one additional active compound may be selected from the additional active compounds described above, such as antiviral drugs (including antibodies) and immunostimulatory agents. Preferably, the at least one additional active compound (such as 1, 2, 3, 4, 5, 6, 7, 8, 9, or 10 additional compounds) are independently selected from the group consisting of antiviral drugs (including antibodies directed against an animal pathogenic virus), interferons (e.g., interferon alpha or interferon gamma), interferon derivatives (such pegylated interferons, such as peginterferon alfa, peginterferon alfa-2a, peginterferon alfa-2b, peginterferon Lambda-1a,), other cytokines (such as interleukins (e.g., interleukin 7 (IL-7), IL-1. IL-2, IL-12)), or agents inducing the production of interferons by the host (e.g., agonists of Toll Like Receptor 3 (TLR3)).

In any of the above therapeutic aspects, wherein the method comprises the steps of administering a pyrone derivative as specified above and administering at least one additional active compound, the at least additional active compound, for example the antiviral drug and/or immunostimulatory agent, may be formulated together with the pyrone derivative as described above in a single pharmaceutical composition. Alternatively, the pharmaceutical composition may be structured as kit of parts, wherein the pyrone derivative is provided in a first formulation and the at least one additional active compound, for example the antiviral drug and/or immunostimulatory agent, is provided in a second formulation, i.e., a second pharmaceutical composition. The first and the second pharmaceutical compositions may be combined prior to use. In other words, before administering the pharmaceutical composition, a formulation comprising the additional active compound may be added to the first pharmaceutical composition comprising the pyrone derivative. Alternatively, the present teaching envisages administering the pyrone derivative formulated in a first pharmaceutical composition and administering the at least one additional active compound formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

In one embodiment, the animal pathogenic virus is selected from the viruses disclosed herein. Preferably, the animal pathogenic virus is a member of a family selected from the group conisisting of Retroviridae, Herpesviridae, Hepadnaviridae, Orthomyxoviridae, Flaviviridae, Polyomaviridae, and Papillomaviridae, preferably from the group consisting of Herpesviridae, Papillomaviridae, Polyomaviridae, Hepadnaviridae, Flaviviridae, and Retroviridae. In one embodiment, the animal pathogenic virus is a human pathogenic virus. In one embodiment, the animal pathogenic virus is selected from the group consisting of human deficiency virus (HIV), hepatitis B virus (HBV), herpes simplex virus (HSV), human herpesvirus 6 (HHV6), human herpesvirus 7 (HHV7), cytomegalovirus (CMV), Epstein-Barr virus (EBV), influenzavirus, hepatitis C virus (HCV), human papilloma virus (HPV), and human T-cell lymphotropic virus (HTLV), such as human deficiency virus (HIV), hepatitis B virus (HBV), and herpes simplex virus (HSV). For example, the animal pathogenic virus may be selected from the group consisting of HIV-1, HIV-2, HBV-A, HSV-1, HSV-2, human CMV (HCMV), EBV type 1, EBV type 2, influenzavirus A, influenzavirus B, human herpesvirus 6 (HHV6), human herpesvirus 7 (HHV7), HCV, HPV-16, HPV-18, HTLV-1, and HTLV-2.

In one embodiment, the animal pathogenic virus mediates or cuases a chronic condition, disorder or disease. Preferably, the animal pathgogenic animal that mediates or cuases a chronic condition, disorder or disease is a member of a family selected from the group conisisting of Herpesviridae, Papillomaviridae, Polyomaviridae, Hepadnaviridae, Flaviviridae, and Retroviridae. In one embodiment, the animal pathogenic virus that mediates or causes a chronic condition, disorder or disease is selected from the group consisting of human deficiency virus (HIV), hepatitis B virus (HBV), herpes simplex virus (HSV), human herpesvirus 6 (HHV6), human herpesvirus 7, cytomegalovirus (CMV), Epstein-Barr virus (EBV), hepatitis C virus (HCV), human papilloma virus (HPV), and human T-cell lymphotropic virus (HTLV), such as human deficiency virus (HIV), hepatitis B virus (HBV), human herpesvirus 6 (HHV6), human herpesvirus 7 and herpes simplex virus (HSV). For example, the animal pathogenic virus that mediates or causes a chronic condition, disorder or disease may be selected from the group consisting of HIV-1, HIV-2, HBV-A, HSV-1, HSV-2, human CMV (HCMV), EBV type 1, EBV type 2, HCV, HPV-16, HPV-18, human herpesvirus 6 (HHV6), human herpesvirus 7 (HHV7), HTLV-1, and HTLV-2, preferably HIV-1, HIV-2, HBV-A, HSV-1, HSV-2, human CMV (HCMV), EBV type 1, EBV type 2, HCV, HPV-16, HPV-18, HTLV-1, and HTLV-2.

In one embodiment, the animal pathogenic virus is a reverse transcribing virus, wherein the virus may have an RNA genome (i.e., Baltimore classification group VI; e.g., the virus is a member of the family Retroviridae) or a DNA genome (i.e., Baltimore classification group VII, e.g., the virus is a member of the family Hepadnaviridae). Particular examples are HIV and HBV.

In one embodiment, the condition, disorder or disease is mediated or caused by an animal pathogenic virus strain which is resistant against one or more antiviral drugs. For example, the condition, disorder or disease may be mediated or caused by an animal pathogenic virus strain which is resistant against one or more (e.g., 1, 2, 3, or 4) known antiviral drugs selected from the group consisting of entry inhibitors, reverse transcriptase (RT) inhibitors, integrase inhibitors, protease inhibitors, inhibitors of DNA synthesis, uncoating inhibitors, assembly inhibitors, and release inhibitors. Preferably, the known antiviral drugs are selected from the group consisting of maraviroc, enfuvirtide, zidovudine, didanosine, zalcitabine, stavudine, lamivudine, abacavir, emtricitabine, entecavir, tenofovir, adefovir, efavirenz, nevirapine, delavirdine, etravirine, rilpivirine, raltegravir, elvitegravir, dolutegravir, saquinavir, ritonavir, indinavir, nelfinavir, amprenavir, boceprevir, telaprevir, lopinavir, atazanavir, fosamprenavir, tipranavir, darunavir, amantadine, rimantidine, rifampicin, zanamivir, and oseltamivir. In one embodiment, the known antiviral drugs are selected from the group consisting of enfuvirtide, zidovudine, raltegravir, and saquinavir. In one embodiment, the animal pathogenic virus strain is resistant against (i) enfuvirtide; (ii) zidovudine; (iii) raltegravir; (iv) saquinavir; (v) oseltamivir; (vi) ganciclovir; (vii) foscarnet; (viii) acyclovir; (ix) famciclovir; (x) valacyclovir and/or (xi) amantadine. In one embodiment, the animal pathogenic virus strain is multidrug-resistant against (i) amantadine and oseltamivir; (ii) ganciclovir and foscarnet; (iii) acyclovir and famciclovir; (iv) acyclovir and valacyclovir; or (v) acyclovir, famciclovir, and valacyclovir.

In one embodiment, the pyrone derivates described herein (in particular the pyrone derivatives having the general formula (I), (Ia), (Ib), (Ic), (Id), (Ie), (If), (Ig), (Ih), (II), (IIa), (IIb), (IIc), (IId), (IIe), or (IIf) as well as any pharmaceutical composition described herein which contains at least on such pyrone derivate) may be used to treat and/or prevent a persistent infection, such as a chronic or latent infection. Particular examples of viruses causing a chronic infection include hepatitis B virus, hepatitis D virus, hepatitis C virus, viruses of the family Herpesviridae, Epstein-Barr virus, cytomegalovirus and human T-lymphotropic virus (such as HTLV type III). Particular examples of viruses causing a latent infection include viruses of the family Herpesviridae, such as Chicken-pox virus, Herpes simplex viruses (HSV-1, HSV-2), human herpesvirus 6 (HHV6), human herpesvirus 7 (HHV7), and Epstein-Barr Virus.

In one embodiment, the pyrone derivatives described herein (in particular the pyrone derivatives having the general formula (I), (Ia), (Ib), (Ic), (Id), (Ie), (If), (Ig), (Ih), (II), (IIa), (IIb), (IIc), (IId), (IIe), or (IIf) as well as any pharmaceutical composition described herein which contains at least on such pyrone derivate) may be used to treat and/or prevent a persistent infection in a subject which is caused by a virus the viral genome of which is stably integrated into the cellular DNA of the subject. Particular examples of viruses the genome of which is stably integrated into the cellular DNA of the subject include hepatitis B virus, and viruses of the family Retroviridae (such as human T-lymphotropic virus).

Alternatively, the pyrone derivatives described herein (in particular the pyrone derivatives having the general formula (I), (Ia), (Ib), (Ic), (Id), (Ie), (If), (Ig), (Ih), (II), (IIa), (IIb), (IIc), (IId), (IIe), or (IIf) as well as any pharmaceutical composition described herein which contains at least on such pyrone derivate) may be used to treat and/or prevent a persistent infection in a subject which is caused by a virus the genome of which is maintained in episomes (such episomes may be in the cytoplasm and/or the nucleus of host cells infected with the virus; the viral genome may be in the form of covalently closed circular DNA). Particular examples of viruses the genome of which is maintained in episomes include Chicken-pox virus, Herpes simplex viruses (HSV-1, HSV-2), human herpesvirus 6 (HHV6), human herpesvirus 7 (HHV7) and Epstein-Barr Virus.

In one embodiment, the pyrone derivatives described herein (in particular the pyrone derivatives having the general formula (I), (Ia), (Ib), (Ic), (Id), (Ie), (If), (Ig), (Ih), (II), (IIa), (IIb), (IIc), (IId), (IIe), or (IIf)) can be administered in lower doses compared to one or more known antiviral drugs (preferably, without altering the therapeutic outcome when using the same or comparable conditions (including mode and time period of administration, severity of the disease to be treated, age, gender, and condition of the subject to be treated, etc.)). In certain embodiments, the pyrone compounds described herein (in particular the pyrone derivatives having the general formula (I), (Ia), (Ib), (Ic), (Id), (Ie), (If), (Ig), (Ih), (II), (IIa), (IIb), (IIc), (IId), (IIe), or (IIf)) can be administered in doses which are at most 90% (such at most 80%, at most 70%, at most 60%, at most 50%, at most 45%, at most 40%, at most 35%, at most 30%, at most 25%, at most 20%, at most 15%, at most 10%, at most 9%, at most 8%, at most 7%, at most 6%, at most 5%, at most 4%, at most 3%, at most 2%, at most 1%, at most 0.9%, at most 0.8%, at most 0.7%, at most 0.6%, at most 0.5%, at most 0.4%, at most 0.3%, at most 0.2%, at most 0.1%, at most 0.05%, at most 0.01%, at most 0.009%, at most 0.008%, at most 0.007%) of the dose of the known antiviral drug. Preferably, the known antiviral drugs are selected from the group consisting of maraviroc, enfuvirtide, zidovudine, didanosine, zalcitabine, stavudine, lamivudine, abacavir, emtricitabine, entecavir, tenofovir, adefovir, efavirenz, nevirapine, delavirdine, etravirine, rilpivirine, raltegravir, elvitegravir, dolutegravir, saquinavir, ritonavir, indinavir, nelfinavir, amprenavir, boceprevir, telaprevir, lopinavir, atazanavir, fosamprenavir, tipranavir, darunavir, amantadine, rimantidine, rifampicin, zanamivir, and oseltamivir. In one embodiment, the known antiviral drugs are selected from the group consisting of enfuvirtide, zidovudine, raltegravir, and saquinavir.

Generally, the amount of a pyrone derivative as described herein (in particular the amount of a pyrone derivative having the general formula (I), (Ia), (Ib), (Ic), (Id), (Ie), (If), (Ig), (Ih), (II), (IIa), (IIb), (IIc), (IId), (IIe), or (IIf)) administered daily to an individual may be at most 100 mg/kg (such as at most 50 mg/kg, at most 40 mg/kg, at most 30 mg/kg, at most 20 mg/kg, at most 10 mg/kg, at most 9 mg/kg, at most 8 mg/kg, at most 7 mg/kg, at most 6 mg/kg, at most 5 mg/kg, at most 4 mg/kg, at most 3 mg/kg, at most 2 mg/kg, or at most 1 mg/kg), depending on factors such as the condition of the subject to be treated and the mode of administration. For example, the amount of a pyrone derivative as described herein (in particular the amount of a pyrone derivative having the general formula (I), (Ia), (Ib), (Ic), (Id), (Ie), (If), (Ig), (Ih), (II), (IIa), (IIb), (IIc), (IId), (IIe), or (IIf)) administered daily to an individual may range from about 0.01 mg/kg to 100 mg/kg (such as from about 0.05 mg/kg to 50 mg/kg, from about 0.1 mg/kg to 40 mg/kg, from about 0.2 mg/kg to 30 mg/kg, from about 0.3 mg/kg to 20 mg/kg, from about 0.4 mg/kg to 10 mg/kg, from about 0.5 mg/kg to 9 mg/kg, from about 0.6 mg/kg to 8 mg/kg, from about 0.7 mg/kg to 7 mg/kg, from about 0.8 mg/kg to 6 mg/kg, from about 0.9 mg/kg to 5 mg/kg, from about 1 mg/kg to 4 mg/kg or from about 2 mg/kg to 3 mg/kg) depending on factors such as the condition of the subject to be treated and the mode of administration.

In one embodiment, the pyrone derivative (in particular the pyrone derivative having the general formula (I), (Ia), (Ib), (Ic), (Id), (Ie), (If), (Ig), (Ih), (II), (IIa), (IIb), (IIc), (IId), (IIe), or (IIf)) is orally administered in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the pyrone derivative (in particular the pyrone derivative having the general formula (I), (Ia), (Ib), (Ic), (Id), (Ie), (If), (Ig), (Ih), (II), (IIa), (IIb), (IIc), (IId), (IIe), or (IIf)) is parenterally administered (e.g., intravenously, intramuscularly, or subcutaneously), in a concentration of at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

Other features and advantages of the present invention will be apparent from the following examples which are included to demonstrate preferred embodiments of the present invention but which do not limit the present invention. Rather, in light of the present disclosure, the skilled person will appreciate that many changes can be made in the specific embodiments which are disclosed and still obtain a like or similar result without departing from the scope of the invention.

EXAMPLES

Materials and Methods

Generally, the methods and materials described in Kremb, S., et al., *Antimicrob. Agents Chemother.* 54 (2010), 5257-5268 were used in the examples of the present application.

Cell Culture.

The HIV indicator LC5-RIC cell line (where RIC is red infected cells, indicating the LC5 parental line expressing the DsRed1 reporter), the $HIV1_{IIIB}$-producer T-lymphoma cell line KE37.1-IIIB, the uninfected T-lymphoma cell line KE37.1, and HEK 293T cells were cultured under standard conditions at 37° C. in 5% $CO_2$ in Dulbecco's modified Eagle medium (DMEM containing GlutaMAX-1; Gibco, Darmstadt, Germany) or very-low-endotoxin (VLE)-RPMI 1640 medium (Biochrom AG, Berlin, Germany) supplemented with 10% fetal bovine serum (Biochrom AG) and 1% antibiotic-antimycotic solution (Gibco). LC5-RIC reporter cells were maintained under selection pressure by addition of 0.74 mg/ml Geneticin (G418 sulfate; PAA Laboratories, Pasching, Austria) and 0.125 mg/ml hygromycin B (PAA Laboratories) to the cell culture medium at every second passage to retain stable expression of the CD4 receptor and to ensure stability of the reporter construct. Selection antibiotics were removed 2 days before the cells were seeded into the assay plates and were generally not used during the assay.

LC5-RIC cells were used for a maximum of 10 passages, and every new batch of cells was initially checked for the expression of CD4 and CXCR4 receptors by flow cytometry (see below) and signal performance by determination of the signal-to-background ratio. Only LC5-RIC batches showing expression of CD4 and CXCR4 on ≥80% of the cells, no background expression of the reporter, and over 100-fold induction of relative signal intensities in HIV infection assays were used for further applications.

Standard Assay Setup for Testing of Inhibitors.

LC5-RIC cells were seeded into 96-well plates (μCLEAR-Plate Black; Greiner Bio-One, Kremsmuenster, Germany), using only the 60 inner wells to avoid adverse effects caused by variations in the culture conditions in the outer wells. Cells were seeded at a density of $10^4$ per well at 24 h prior to infection. Compounds were tested either at single concentrations or in serial dilutions, with each concentration assayed in triplicate. Compound solution (100 μl) followed by 20 μl of HIV inoculum ($10^8$ RNA copies/ml inoculum for KE37.1-derived HIV-1IIIB or 28.8 ng of p24 for HIV-1LAI derived from HEK 293T cells) was added to each well. To assay maximum infection (i.e., 100%), HIV inoculum was added to LC5-RIC cells incubated with compound-free medium. Controls for background expression consisted of LC5-RIC cells cultured in conditioned medium from KE37.1 (i.e., uninfected) cells. Plates were incubated for 48 h after virus addition, after which cultures were assayed for cellular reporter expression and for titers of infectious virus in supernatant fluids. Reporter expression was determined by measuring the total fluorescent signal intensity of each culture with a fluorescence microplate reader (Fluoroskan Ascent; ThermoFisher, Schwerte, Germany) at an excitation filter wavelength of 544 nm and an emission filter wavelength of 590 nm or with a Tecan infinite M200 (Tecan, Crailsheim, Germany) at the monochromator wavelengths 552 nm for excitation and 596 for emission. To quantify infectious virus titers, supernatant fluids (30 μl of $HIV-1_{IIIB}$ or 20 μl for HIV-1LAI) from cultures in the first plate were transferred to a second plate with uninfected LC5-RIC cells in exact replicate, and total fluorescent signal intensities of cultures in the second plate were measured 72 h after transfer.

Cell Viability Assays.

Effects of compounds on cell viability wasy measured by MTT assay, Cell Titre Blue Assay and Cell Tox Green Assay. The MTT assay and the Cell Titre Blue Assay evaluate metabolic activity of cells, The Cell Tox Green assay measures cell death (i.e. loss of cell membrane integrity). The MTT assay measures the reduction of the yellow MTT to purple formazan by mitochondrial enzymes (Mosmann, T., *J. Immunol. Methods* 65 (1983), 55-63) Immediately following measurement of reporter expression, cultures were incubated with 100 μl of MTT solution (0.5 mg of MTT; Sigma, Taufkirchen, Germany) in 100 μl of culture medium for 2 h under standard culture conditions. MTT solution was carefully removed, and cells were lysed by addition of 100 μl of lysis solution (10% [wt/vol] SDS and 0.6% [vol/vol] acetic acid in dimethyl sulfoxide [DMSO]). The released MTT formazan crystals were dissolved by gentle agitation, and MTT formazan concentrations were determined by an ELISA plate reader (SmartSpec Plus; Bio-Rad, Muenchen, Germany) or Tecan Infinite M200 at a test wavelength of 570 nm and a reference wavelength of 630 nm. Values for treated HIV-infected cultures were related to those of untreated, HIV-infected cultures in the same plate. The Cell Titre Blue Assay measures converson of resazuin to resorufin by metablically active cells and was performed with the Promega CellTitre-Blue™ kit according to manufacturer's instructions. The Promega CellTox™ Green assay measures binding of a cell-membrane impermeable dye to free DNA released by dead or dying cells and was performed according to manufactuere's instruction.

Time-of-Addition (TOA) Assay.

TOA assays were performed in 96-well plates using a standard assay setup with some modifications. HIV-1IIIB virus preparations were added to LC5-RIC cultures at time point 0. Anti-HIV compounds were added to the cultures at different time points after addition of virus preparations. Inhibitor concentrations were ≥2× $EC_{50}$ in each well. At least 15 different time points were evaluated for each compound in at least three wells per time point. Cultures were incubated with virus for 48 h and subsequently analyzed for cellular reporter gene expression and/or infectious virus titers in culture supernatants.

Flow Cytometry.

Immunostaining of LC5-RIC cells for CD4 and chemokine receptor CXCR4 was carried out as described by Rothenaigner et al. (AIDS 21 (2007), 2271-2281). Allophycocyanin (APC)-conjugated CD4- and CXCR4-specific antibodies (BD Pharmingen) were used to detect surface receptors CD4 and CXCR4. Cells were analyzed by flow cytometry (FACSCalibur; Beckton Dickinson) using channels FL1 (FITC), FL3 (DsRed1), or FL4 (APC).

Calculation of Values and Curve Fits.

Curve fits and $EC_{50}$ calculations were done with Prism, version 4 (GraphPad Software, La Jolla, Calif.), using the equation for sigmoidal dose response with variable slope with the following set constraint parameters: fixed top of 100 and fixed bottom of 0. As internal acceptance criteria, $R^2$ values had to be ≥0.9.

The abbreviations used in the present invention have the following meanings:

h=hour
μm=micromolar
kg=kilogram
min=minute
nM=nanomolar
wt=weight
vol=volume

Example 1

To evaluate the inhibitory effects of the pyrone derivatives described herein, the EASY-HIT assay was used as disclosed in Kremp et al., supra. Briefly, a pyrone compound (or another test compound) was added to LC5-RIC cultures (or other uninfected cells, such as PBMCs) in microtiter plates, HIV preparations were added within 30 min of beginning treatment, and test cultures were incubated for 48 h after virus addition. Reference cultures were either exposed to the virus without test compound (maximum signal) or not exposed to the virus (minimum signal). Effects of test compounds on HIV infection of LC5-RIC cultures were determined in two steps. The first step quantified reporter expression by assaying fluorescent signal intensities of cells in test cultures. The second step quantified the infectious virus produced in test cultures by transferring aliquots of supernatants of test cultures to uninfected LC5-RIC cells (or other uninfected cells, such as PBMCs), followed by measurement of fluorescent signal intensities at 72 h after transfer. Cells evaluated for reporter expression were subjected to an MTT assay to detect deleterious effects of test compounds on cell viability under test conditions.

FIG. 1A shows the measured fluorescence signal intensities obtained in the first step, whereas FIG. 1B depicts the measured fluorescence signal intensities obtained in the second step. As can be seen from these data, the fluorescent signal intensities for both stages were greatly reduced when Compound 1 was present indicating a high inhibitory effect of Compound 1 ($EC_{50}$=0.6 nM) with respect to HIV replication. In contrast, Compound 1 did not exhibit any toxic effect at the wide concentration range tested (0 to 120 μM); cf. FIG. 1C. Similar results were obtained when PBMCs (instead of LC5-RIC cells) were used in the first step; cf. FIGS. 1D and E.

Example 2

While the basic EASY-HIT discovery assay distinguishes between inhibitors of early and late phases of HIV-1 replication, characterization of inhibitory activities would benefit from the means to discriminate different steps of HIV replication at higher resolution. Time-of-addition assays monitor the inhibitory efficacies of test compounds added to HIV target cells at different time points after exposure of the cells to the virus.

To further characterize the inhibitory effects of Compound 1, HIV preparations were added to LC5-RIC cells at the time point 0. Compound 1 was added to the cultures at different time points after virus addition (i.e., p.i.). Plates were incubated for a total period of 48 h after virus addition, and cultures were assayed for HIV reporter expression (step 1) or for amounts of infectious virus in culture supernatants (step 2). Fluorescent signal intensities of treated cultures were related to those of cultures infected without inhibitors (set at 100% infection).

As can be seen from FIG. 2, Compound 1 inhibited the HIV replication at a very early stage and was able to block the HIV replication even if the time between the addition of Compound 1 to the cells and the time of infection was 30 h.

Example 3

To further characterize the inhibitory effects of Compound 1, a further cell line (HNSCLatGFP1.1) was established into the genome of which the genome of a HIV-1-gfp reporter virus has been stably integrated. This cell line is transcriptionally inactive with respect to the expression of HIV-1, but said expression can be induced by activators (such as TNF or SAHA (suberoylanilide hydroxamic acid, also designated as vorinostat)) and measured using the GFP reported (FACS).

Reference cultures were either untreated (minimum signal; lane 1 of FIG. 3A) or exposed to TNF (maximum signal; lane 2 of FIG. 3A). HNSCLatGFP1.1 cells were exposed to different concentrations of Compound 1 either alone (lanes 3 to 5 of FIG. 3A) or together with TNF (lanes 6 to 8 of FIG. 3A). As can be seen from FIG. 3A, Compound 1 was able to inhibit virus production in HNSCLatGFP1.1 cells in a dose dependent manner. Similar results were obtained when using a combination of stimulators (TNF and SAHA; cf. FIG. 3B) or a different stimulator (cf. FIG. 3C).

Example 4

The human hepatoma cell line HepG2.2.15, stably expressing HBV particles, was seeded in a 48 well format at a density of $5 \times 10^4$ the day before starting the treatment. Next day the cells were treated with 1 μM, 100 nM, 10 nM and 1 nM of Compound 1 with 3 independent biological replicates each. The cells were cultured in differentiation medium containing 1.8% DMSO, to slow down cell growth and enhance viral replication. Three days after treatment, cell viability (FIG. 4A) was determined by cell titer blue assay, cell supernatants were analyzed for HBeAg and newly released viral particles (FIGS. 4B and C) and finally cells were harvested to analyze for intracellular HBV DNA (FIG. 4D). All of the analyzed viral replication markers were strongly reduced in a dose dependent fashion at an $IC_{50}$ between 2 and 20 nM of Compound 1, without affecting cell viability.

In conclusion, Compound 1 showed a strong anti-HBV effect in HepG2.2.15 cells through efficient inhibition of viral replication.

Example 5

To evaluate the HIV inhibitory effects of compounds 4 and 19, compared to a compound lacking the gamma-pyrone moiety, the EASY-HIT assay was used as disclosed in Kremp et al., supra, using the standard assay set-up (see Materials and Methods and description of Example 1). Briefly, the test compound) was added to LC5-RIC cultures in microtiter plates. HIV-1 virus preparations were added within 30 min of beginning treatment with the text compound and test cultures were incubated for 48 h after virus addition. Reference cultures were either exposed to the virus without test compound (maximum signal) or not exposed to the virus (minimum signal). Effects of test compounds on HIV infection of LC5-RIC cultures were determined in two steps. The first step quantified reporter expression by assaying fluorescent signal intensities of cells in test cultures. The second step quantified the infectious virus produced in test cultures by transferring aliquots of supernatants of test cultures to uninfected LC5-RIC cells, followed by measurement of fluorescent signal intensities at 72 h after transfer. Cells evaluated for reporter expression were subjected to the Cell Titre Blue Assay to detect deleterious effects of test compounds on cell viability under test conditions.

As can be seen from FIG. 5, compounds 4 and 19 both inhibit HIV-1 replication, while the compound lacking the gamma-pyrone moiety (structure of compound depicted) is inactive. Antiviral activity is stronger in step 2 than step 1, indicatingthat the compounds exhibit stronger antiviral effects in the late phase of virus replication than in the early phase. None of the compounds affected metabolic activity of the cells under test conditions.

Example 6

The anti-HIV-1 activites of compounds 20, 21, 22, 23, 24 and 26 were evaluated with EASY-HIT assay as disclosed in Kremp et al., supra, using the standard assay set-up (see Materials and Methods and description of Examples1 and 5). Cells evaluated for reporter expression were subjected to the Cell Titre Blue Assay to detect deleterious effects of test compounds on cell viability under test conditions.

As can be seen from FIG. 6, the compounds inhibit the late phase of HIV-1 replication with different efficacies. Compounds 21 and 22 showed highest activities and compound 23 lowest activity. None of the compounds affected metabolic activity of the cells under test conditions.

Example 7

The anti-HIV-1 activites of compounds 1, 2, 4, 6, 7, 9, 10, 11, 12, 13, 14, 19, 20, 21, 22, 23, 24, 26 and 28 were evaluated with EASY-HIT assay as disclosed in Kremp et al., supra, using the standard assay set-up (see Materials and Methods and description of Examples 1, 5 and 6).

As can be seen from FIG. 7, the compounds inhibit the late phase of HIV-1 replication with different efficacies.

Example 8

Effects of compounds 1, 4, 7, 10, 11 and 14 on the viability of LC5-RIC cells were evaluated by the Cell Titre Blue Assay and Cell Tox Green Assay, which measure metabolic activity of cells and cell viability (see also Materials and Methods).

As can be seen from FIG. 8, cells in cultures exposed to HIV and treated with the compounds retain over 85% metabolic activity and at least 100% viability, compared to untreated cultures.

The invention claimed is:
1. A method of treating a patient or preventing a patient from, suffering from a condition, disorder or disease that is mediated or caused by an animal pathogenic virus which uses cellular mechanisms in the animal host for its replication and/or transcription comprising administering an effective amount of a compound selected from the group consisting of a pyrone derivative having the general formula (I) or (II)

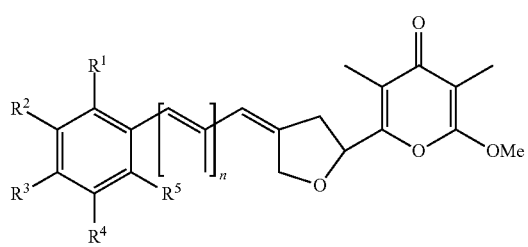

(I)

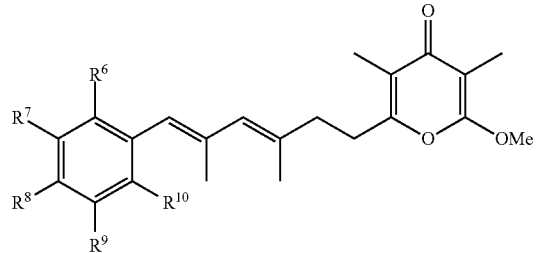

(II)

and hydrates, solvates, salts, complexes, racemic mixtures, diastereomers, enantiomers, and tautomers thereof and isotopically enriched forms of any of the foregoing,
wherein
$R^1$, $R^2$, $R^3$, $R^4$, and $R^5$ are independently selected from the group consisting of hydrogen, halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, cycloalkyl, heterocyclyl, aryl, and heteroaryl groups is substituted with from 0 to 3 substituents independently selected from the group consisting of $R^{30}$, phosphoryl, folic acid, and molecular probes; or either $R^1$ and $R^2$, or $R^2$ and $R^3$, or $R^3$ and $R^4$, or $R^4$ and $R^5$ may join together with the atoms to which they are attached to form a 5- to 8-membered ring that is substituted with from 0 to 3 substituents independently selected from the group consisting of $R^{30}$, phosphoryl, folic acid, and molecular probes;
$R^6$, $R^7$, $R^8$, $R^9$, and $R^{10}$ are independently selected from the group consisting of hydrogen, halogen, nitro, cyano, isocyano, cyanato, isocyanato, thiocyanato, isothiocyanato, azido, alkyl, alkenyl, alkynyl, cycloalkyl, heterocyclyl, aryl, heteroaryl, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, cycloalkyl, heterocyclyl, aryl, and heteroaryl groups is substituted with from 0 to 3 substituents independently selected from the group consisting of $R^{30}$, phosphoryl, folic acid, and molecular probes; or either $R^6$ and $R^7$, or $R^7$ and $R^8$, or $R^8$ and $R^9$, or $R^9$ and $R^{10}$ may join together with the atoms to which they are attached to form a 5- to 8-membered ring that is substituted with from 0 to 3 substituents independently selected from the group consisting of $R^{30}$, phosphoryl, folic acid, and molecular probes;
n is 1, 2, or 3,
X is independently selected from O, S, and $N(R^{14})$;
$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more independently selected $R^{30}$;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, —NC, —NCO, —CNO, —SCN, —NCS, —$N_3$, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$, if $R^{30}$ is alkyl, alkenyl, aryl, heteroaryl, cycloalkyl, heterocyclyl, —$OR^{71}$, —$N(R^{72})(^{73})$, —$OS(O)_{1-2}R^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, —NC, —NCO, —CNO, —SCN, —NCS, —$N_3$, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents, if selected from $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$ which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups being a $2^{nd}$ level substituent is optionally substituted with one or more $3^{rd}$ level substituents, wherein said $3^{rd}$ level substituent is, in each case, independently selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —$NHS(O)_2(C_{1-3}$ alkyl), —$S(O)_2NH_{2-z}(C_{1-3}$ alkyl)$_z$, —C(=O)($C_{1-3}$ alkyl), —C(=O)OH, —C(=O)O($C_{1-3}$ alkyl), —C(=O)$NH_{2-z}(C_{1-3}$ alkyl)$_z$, —OC(=O)($C_{1-3}$ alkyl), —OC(=O)O($C_{1-3}$ alkyl), —OC(=O)$NH_{2-z}(C_{1-3}$ alkyl)$_z$, —NHC(=O)($C_{1-3}$ alkyl), —NHC(=O)$NH_{2-z}(C_{1-3}$ alkyl)$_z$, —NHC(=NH)$NH_{2-z}(C_{1-3}$ alkyl)$_z$, and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents, if selected from $C_{1-3}$ alkyl, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —$NHS(O)_2(C_{1-3}$ alkyl), —$S(O)_2NH_{2-z}(C_{1-3}$ alkyl)$_z$, —C(=O)($C_{1-3}$ alkyl), —C(=O)OH, —C(=O)O($C_{1-3}$ alkyl), —C(=O)$NH_{2-z}(C_{1-3}$ alkyl)$_z$, —OC(=O)($C_{1-3}$ alkyl), —OC(=O)O($C_{1-3}$ alkyl), —OC(=O)$NH_{2-z}(C_{1-3}$ alkyl)$_z$, —NHC(=O)($C_{1-3}$ alkyl), —NHC(=O)$NH_{2-z}(C_{1-3}$ alkyl)$_z$, —NHC(=NH)$NH_{2-z}(C_{1-3}$ alkyl)$_z$, and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl, which are bound to the same carbon atom of a 3- to 14-membered cycloalkyl or heterocyclyl group being a $2^{nd}$ level substituent may join together to form =O, =S, =NH, or =N($C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —$NHS(O)_2(C_{1-3}$ alkyl), —$S(O)_2NH_{2-z}(C_{1-3}$ alkyl)$_z$, —C(=O)($C_{1-3}$ alkyl), —C(=O)OH, —C(=O)O($C_{1-3}$ alkyl), —C(=O)$NH_{2-z}(C_{1-3}$ alkyl)$_z$, —OC(=O)($C_{1-3}$ alkyl), —OC(=O)O($C_{1-3}$ alkyl), —OC(=O)$NH_{2-z}(C_{1-3}$ alkyl)$_z$, —NHC(=O)($C_{1-3}$ alkyl), —NHC(=NH)$NH_{z-2}(C_{1-3}$ alkyl)$_z$, and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl; $R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, —NC, —NCO, —CNO, —SCN, —NCS, —$N_3$, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —OC(=O)($C_{1-3}$ alkyl), —OC(=O)O($C_{1-3}$ alkyl), —OC(=O)NH$_{2-z}$($C_{1-3}$ alkyl)$_z$, —NHC(=O)($C_{1-3}$ alkyl), —NHC(=O)NH$_{2-z}$($C_{1-3}$ alkyl)$_z$, —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl; and wherein $R^3$ is not nitro when $R^1$, $R^2$, $R^4$ and $R^5$ are —H.

2. The method according to claim 1, wherein
(i) one of $R^1$ to $R^5$ is hydrogen and the rest of $R^1$ to $R^5$ is other than hydrogen; or
(ii) two of $R^1$ to $R^5$ are hydrogen and the rest of $R^1$ to $R^5$ is other than hydrogen; or
(iii) three of $R^1$ to $R^5$ are hydrogen and the rest of $R^1$ to $R^5$ is other than hydrogen; or
(iv) four of $R^1$ to $R^5$ are hydrogen and the rest of $R^1$ to $R^5$ is other than hydrogen; or
(v) $R^1$ to $R^5$ are hydrogen; or
(vi) one of $R^6$ to $R^{10}$ is hydrogen and the rest of $R^6$ to $R^{10}$ is other than hydrogen; or
(vii) two of $R^6$ to $R^{10}$ are hydrogen and the rest of $R^6$ to $R^{10}$ is other than hydrogen; or
(viii) three of $R^6$ to $R^{10}$ are hydrogen and the rest of $R^6$ to $R^{10}$ is other than hydrogen; or
(ix) four of $R^6$ to $R^{10}$ are hydrogen and the rest of $R^6$ to $R^{10}$ is other than hydrogen; or
(x) $R^6$ to $R^{10}$ are hydrogen.

3. The method according to claim 1, wherein
(i) $R^3$ and $R^8$ are nitro; or
(ii) $R^3$ is selected from the group consisting of hydrogen, halogen, methoxy, methyl, tert-butyl, —S(O)$_2$—$CH_3$, —NH—S(O)$_2$—$CH_3$ and trifluoromethyl; or
(iii) $R^8$ is selected from the group consisting of hydrogen, halogen, cyano, nitro, methoxy, and methyl; or
(iv) $R^2$ and $R^3$ are taken together to form a 6-membered cycloaliphatic ring; or
(v) $R^7$ and $R^8$ are taken together to form a 6-membered cycloaliphatic ring; or
(vi) $R^2$ and $R^3$ are taken together to form a 6-membered aromatic ring; or
(vii) $R^7$ and $R^8$ are taken together to form a 6-membered aromatic ring; or
(viii) $R^3$ and $R^8$ are selected from the group consisting of halogen, nitro, —$OR^{11}$, alkyl, —S(O)$_{0-2}R^{11}$, —N($R^{11}$)S(O)$_{1-2}R^{11}$, and —C(=X)$XR^{11}$, wherein the alkyl group is substituted with from 0 to 3 independently selected $R^{30}$; or
(ix) two of $R^1$ to $R^5$ are selected from halogen and —$OR^{11}$.

4. The method according to claim 1, wherein
(i) $R^1$, $R^2$, $R^4$, and $R^5$ are each hydrogen; and $R^3$ is nitro; or
(ii) $R^1$, $R^2$, $R^4$, and $R^5$ are each hydrogen; and $R^3$ is selected from the group consisting of hydrogen, halogen, methoxy, methyl, trifluoromethyl, tert-butyl, —C(O)$NH_2$, —S(O)$_2$—$CH_3$, and —NH—S(O)$_2$—$CH_3$; or (iii) $R^6$, $R^7$, $R^9$, and $R^{10}$ are each hydrogen; and $R^8$ is selected from the group consisting of hydrogen, halogen, cyano, methoxy, and methyl; or
(iv) $R^1$, $R^3$, $R^4$, and $R^5$ are each hydrogen; and $R^2$ is nitro; or
(v) $R^6$, $R^8$, $R^9$, and $R^{10}$ are each hydrogen; and $R^7$ is nitro; or
(vi) $R^2$, $R^3$, $R^4$, and $R^5$ are each hydrogen; and $R^1$ is halogen; or
(vii) $R^1$, $R^3$, $R^4$, and $R^5$ are each hydrogen; and $R^2$ is halogen; or
(viii) $R^2$, $R^4$, and $R^5$ are each hydrogen; and $R^1$ and $R^3$ are each halogen; or
(ix) $R^1$, $R^4$, and $R^5$ are each hydrogen; and $R^2$ and $R^3$ are each methoxy.

5. The method according to claim 1, wherein the compound has formula (I) and n is 1 or 3.

6. The method according to claim 1, wherein the pyrone derivative is selected from the group consisting of:
2-methoxy-3,5-dimethyl-6-{(2R,4Z)-4-[(2E)-2-methyl-3-(4-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(4-bromophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(4-iodophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(naphtalen-2-yl)prop-2-en-1-ylidene]tetra-hydrofuran-2-yl}-4H-pyran-4-one;
2-[(3E,5E)-6-(4-nitrophenyl)-3,5-dimethylhexa-3,5-dien-1-yl]-6-methoxy-3,5-dimethyl-4H-pyran-4-one;
4-[(1E,3E)-6-(6-methoxy-3,5-dimethyl-4-oxo-4H-pyran-2-yl)-2,4-dimethylhexa-1,3-dien-1-yl]benzo-nitrile;
2-[(3E,5E)-6-(4-fluorophenyl)-3,5-dimethylhexa-3,5-dien-1-yl]-6-methoxy-3,5-dimethyl-4H-pyran-4-one;
2-[(3E,5E)-6-(4-chlorophenyl)-3,5-dimethylhexa-3,5-dien-1-yl]-6-methoxy-3,5-dimethyl-4H-pyran-4-one;
2-[(3E,5E)-6-(4-bromophenyl)-3,5-dimethylhexa-3,5-dien-1-yl]-6-methoxy-3,5-dimethyl-4H-pyran-4-one;
2-[(3E,5E)-6-(4-iodophenyl)-3,5-dimethylhexa-3,5-dien-1-yl]-6-methoxy-3,5-dimethyl-4H-pyran-4-one;
2-[(3E,5E)-6-(naphthalen-2-yl)-3,5-dimethylhexa-3,5-dien-1-yl]-6-methoxy-3,5-dimethyl-4H-pyran-4-one;
2-methoxy-3,5-dimethyl-6-{(2R,4Z)-4-[(2E)-2-methyl-3-(3-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(2-chlorophenyl)prop-2-en-1-ylidene]tetra-hydrofuran-2-yl}-4H-pyran-4-one;
2-methoxy-3,5-dimethyl-6-{(2R,4Z)-4-[(2E)-2-methyl-3-(2,4-difluorophenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(4-trifluoromethylphenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(3,4-dimethoxyphenyl)prop-2-en-1-ylidene]tetrahydrofuran-2-yl}-4H-pyran-4-one;
2-methoxy-3,5-dimethyl-6-{(2R,4Z)-4-[(2E)-2-methyl-3-(4-tert-butylphenyl)prop-2-en-1-ylidene]tetrahydrofuran-2-yl}-4H-pyran-4-one;
4-{(1E,3Z)-3-[(5R)-5-(6-methoxy-3,5-dimethyl-4-oxo-4H-pyran-2-yl)dihydrofuran-3(2H)-ylidene]-2-methylprop-1-en-1-yl}benzamide;

2-methoxy-3,5-dimethyl-6-{(2R,4Z)-4-[(2E)-2-methyl-3-(4-(methylsulfonyl)phenyl)prop-2-en-1-ylidene]tetrahydrofuran-2-yl}-4H-pyran-4-one;

N-(4-{(E,3Z)-3-[(5R)-5-(6-methoxy-3,5-dimethyl-4-oxo-4H-pyran-2-yl)dihydrofuran-3(2H)-ylidene]-2-methyl-prop-1-en-1-yl})methanesulfonamide;

2-methoxy-3,5-dimethyl-6-{(2R,4Z)-4-[(2E)-2-methyl-3-(2-naphthalenyl)prop-2-en-1-ylidene]tetrahydrofuran-2-yl}-4H-pyran-4-one; and 2-[(3E,5E,7E,9E)-10-(4-nitrophenyl)-3,5,7,9-tetramethyldecan-3,5,7,9-tetraen-1-yl]-6-methoxy-3,5-dimethyl-4H-pyran-4-one.

7. The method according to claim 1, wherein the method comprises orally administering the compound in a concentration of at most 100 mg/kg body weight.

8. The method according to claim 1, wherein the animal pathogenic virus is a member of a family selected from the group consisting of Retroviridae, Herpesviridae, Hepadnaviridae, Orthomyxoviridae, Flaviviridae, and Papillomaviridae.

9. The method according to claim 1, wherein the animal pathogenic virus is selected from the group consisting of human deficiency virus (HIV), hepatitis B virus (HBV), herpes simplex virus (HSV), human herpesvirus 6 (HHV6), human herpesvirus 7 (HHV7), cytomegalovirus (CMV), Epstein-Barr virus (EBV), influenzavirus, hepatitis C virus (HCV), human papilloma viruses (HPV), and human T-cell lymphotropic virus (HTLV).

10. The method according to claim 9, wherein the animal pathogenic virus is selected from the group consisting of HIV-1, HIV-2, HBV-A, HSV-1, HSV-2, human CMV (HCMV), EBV type 1, EBV type 2, influenzavirus A, influenzavirus B, HHV6, HHV7, HCV, HPV-16, HPV-18, HTLV-1, and HTLV-2.

11. The method according to claim 1, wherein the condition, disorder or disease is mediated or caused by an animal pathogenic virus strain which is resistant to one or more antiviral drugs.

12. The method according to claim 11, wherein the antiviral drugs are selected from the group consisting of entry inhibitors, reverse transcriptase (RT) inhibitors, integrase inhibitors, protease inhibitors, inhibitors of DNA synthesis, uncoating inhibitors, assembly inhibitors, and release inhibitors.

13. The method according to claim 1, wherein the animal pathogenic virus causes a persistent infection.

14. The method according to claim 1, wherein the method further comprises administering at least one additional active compound.

15. The method according to claim 2, wherein
(i) $R^3$ and $R^8$ are nitro; or
(ii) $R^3$ is selected from the group consisting of hydrogen, halogen, methoxy, methyl, tert-butyl, —S(O)$_2$—CH$_3$, —NH—S(O)$_2$—CH$_3$ and trifluoromethyl; or
(iii) $R^8$ is selected from the group consisting of hydrogen, halogen, cyano, nitro, methoxy, and methyl; or
(iv) $R^2$ and $R^3$ are taken together to form a 6-membered cycloaliphatic ring; or
(v) $R^7$ and $R^8$ are taken together to form a 6-membered cycloaliphatic ring; or
(vi) $R^2$ and $R^3$ are taken together to form a 6-membered aromatic ring; or
(vii) $R^7$ and $R^8$ are taken together to form a 6-membered aromatic ring; or
(viii) $R^3$ and $R^8$ are selected from the group consisting of halogen, nitro, —OR$^{11}$, alkyl, —S(O)$_{0-2}$R$^{11}$, —N(R$^{11}$)S(O)$_{1-2}$R$^{11}$, and —C(=X)XR$^{11}$, wherein the alkyl group is substituted with from 0 to 3 independently selected R$^{30}$; or
(ix) two of $R^1$ to $R^5$ are selected from halogen and —OR$^{11}$.

16. The method according to claim 14, wherein the active compound is at least one antiviral agent.

* * * * *